United States Patent [19]

Bhagwat et al.

[11] Patent Number: 5,025,025

[45] Date of Patent: Jun. 18, 1991

[54] (ARYLSULFONAMIDO- AND PYRIDYL-)-SUBSTITUTED CARBOXYLIC ACIDS AND DERIVATIVES THEREOF AND USE FOR SUPPRESSING THROMBOXANE ACTIVITY

[75] Inventors: Shripad S. Bhagwat, Scotch Plains; Alan J. Main, Basking Ridge, both of N.J.; Herman R. Rodriguez, New York, N.Y.

[73] Assignee: Ciba-Geigy Corporation, Ardsley, N.Y.

[21] Appl. No.: 528,018

[22] Filed: May 23, 1990

Related U.S. Application Data

[63] Continuation-in-part of Ser. No. 373,125, Jun. 28, 1989.

[51] Int. Cl.$^5$ .................. C07D 401/06; C07D 401/12; C07D 213/28; A61K 31/41; A61K 31/44
[52] U.S. Cl. ..................................... 514/340; 514/347; 514/357; 546/276; 546/293; 546/335
[58] Field of Search ............ 546/337, 335, 276, 293; 514/340, 357, 347

[56] References Cited

U.S. PATENT DOCUMENTS

| | | | |
|---|---|---|---|
| 4,113,463 | 9/1978 | Oshio et al. | 71/76 |
| 4,163,855 | 8/1979 | Secor et al. | 546/329 |
| 4,258,058 | 3/1981 | Witte et al. | 514/562 |
| 4,443,477 | 4/1984 | Witte et al. | 514/562 |
| 4,610,981 | 9/1986 | Marsico et al. | 514/158 |
| 4,613,618 | 9/1986 | Choay et al. | 514/538 |
| 4,761,430 | 8/1988 | Choay et al. | 514/562 |
| 4,774,240 | 9/1988 | Böshagen et al. | 514/228.2 |
| 4,789,745 | 12/1988 | Lin | 546/301 |
| 4,843,091 | 6/1989 | Rosentreter et al. | 514/419 |
| 4,902,698 | 2/1990 | Cooper | 514/351 |

FOREIGN PATENT DOCUMENTS 304271 2/1989 European Pat. Off. .
353448 2/1990 European Pat. Off. .

OTHER PUBLICATIONS

European Patent Applic. 253,257 (Derwent Abstract 88-015637/03).
Australian 8,768,808 (Derwent Abstract 87-284485/41).
DE 3,622,865 (Derwent Abstract 88-022151/04).
European Patent Applic. Derwent Abstract 329,360, Aug. 23, 1989.
European Patent Applic. (Abstract) 315,009 (5/10/89).
J. Applied Biochemistry 2 495-509 (1980), G. Reinhardt.
J. Org. Chem. 44, 3136 (1979), H. Secor et al.
European J. Pharmacology, 85, 331 (1982), V. Bertele et al.
Thromb. Haemostas (Stuttgart) 52, 364 (1984), P. Gresele et al.

Primary Examiner—David B. Springer
Assistant Examiner—Lenora Miltenberger
Attorney, Agent, or Firm—Norbert Gruenfeld

[57] ABSTRACT

Disclosed are the compounds of formula

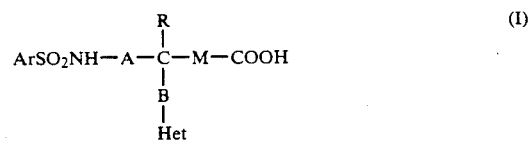

wherein A represents lower alkylene; B represents oxygen, sulfur, lower alkylene, lower alkylene interrupted by oxygen, sulfur, sulfinyl or sulfonyl, (oxy-, sulfinyl-, sulfonyl- or thio)-lower alkylene, lower alkenylene, phenylene or a direct bond; M represents lower alkylene, lower alkylene interrupted by oxygen, sulfur, sulfinyl or sulfonyl, (oxy-, sulfinyl, sulfonyl- or thio)-lower alkylene, lower alkenylene or a direct bond; or one of A, B and M represents lower alkylidenylene and the other two independently represent lower alkylene; R represents hydrogen unless A, B or M represents lower alkylidenylene in which case R represents the second bond to the adjacent aklylidenylene unsaturated carbon atom; Het represents 1-imidazolyl, 3-pyridyl, or 1-imidazolyl or 3-pyridyl substituted by lower alkyl; Ar represents carbocyclic or heterocyclic aryl; pharmaceutically acceptable ester and amide derivatives thereof; the N-oxides of said compounds wherein Het represents optionally substituted pyridyl; the said compounds of formula I wherein COOH is replaced by 5-tetrazolyl; and the pharmaceutically acceptable salts; which are useful as thromboxane synthetase inhibitors and thromboxane receptor antagonists.

60 Claims, No Drawings

(ARYLSULFONAMIDO- AND PYRIDYL-)-SUBSTITUTED CARBOXYLIC ACIDS AND DERIVATIVES THEREOF AND USE FOR SUPPRESSING THROMBOXANE ACTIVITY

CROSS REFERENCE TO RELATED APPLICATIONS

This application is a continuation-in-part of application Ser. No. 373,125 filed June 28, 1989.

SUMMARY OF THE INVENTION

The present invention is concerned with certain (arylsulfonamido- and 3-pyridyl- or 1-imidazolyl-)-substituted carboxylic acids and derivatives thereof which are useful as inhibitors of thromboxane synthetase, as well as thromboxane $A_2$ and prostaglandin $H_2$ receptor antagonists in mammals. The compounds of the invention are thus e.g. especially useful in suppressing the biological effects of endogenous thromboxane $A_2$, e.g. so as to inhibit vasoconstriction and platelet aggregation, in mammals.

The compounds of the invention by virtue of their inhibition of the enzyme thromboxane synthetase modulate the arachidonic acid cascade. They not only reduce the level of endogenous thromboxane $A_2$ synthesized and available to act as agonist at the thromboxane $A_2$ receptor, but can also cause an increase of the level of endogenous prostacyclin; such is beneficial, e.g. in certain cardiovascular conditions, by inhibiting platelet aggregation and also causing vasodilation. Furthermore, the thromboxane $A_2$ receptor blocking activity of the compounds of the invention inhibits the still available endogenous thromboxane $A_2$, as well as prostaglandin $H_2$, from exerting their biological effects, e.g. in causing platelet aggregation and vasoconstriction.

The compounds of the invention are thus particularly useful when administered alone or in combination to mammals for the treatment or prevention of conditions or syndromes in which the effect of endogenous thromboxane is implicated. Such comprise particularly cardiovascular disorders, primarily occlusive vascular conditions involving platelet aggregation such as peripheral vascular diseases, thrombosis, atherosclerosis, cerebral infarctions (strokes) and primary myocardial infarctions (heart attacks), as well as angina (stable and unstable) and hypertension, such as pregnancy induced hypertension. The compounds of the invention can also be used for prevention of reocclusion associated with angioplasty and coronary bypass surgery, and as adjuncts to prevent post-thrombolytic reocclusion from occuring after treatment with thrombolytic agents such as alteplase (also named TPA or tissue plasminogen activator), urokinase, streptokinase, anisoylated plasminogen streptokinase activator complex (APSAC, anistreplase), and related compounds, and to potentiate the thrombolytic effect of said thrombolytic agents. The compounds of the invention can further be used in the treatment of pulmonary disorders, such as bronchial asthma; in conjunction with transplants and immunosuppressive therapy, e.g. with cyclosporine to minimize cyclosporine-induced nephrotoxicity; to improve kidney function, e.g. in lupus nephritis and diabetic nephropathy; to prevent or reduce platelet loss during extracorporeal circulation; in conjunction with other cardiovascular agents, e.g. angiotensin-converting enzyme inhibitors, serotonin-2 inhibitors, calcium channel blockers, beta-blockers and anticoagulants (such as hirudin, desulfatohirudin and heparin) to enhance their cardiovascular effects; and to minimize side effects (e.g. anaphylactoid reaction) induced by protamine, e.g. when protamine is used for reversal of anticoagulant effect of heparin.

DETAILED DESCRIPTION OF THE INVENTION

More particularly the instant invention is concerned with compounds of formula I

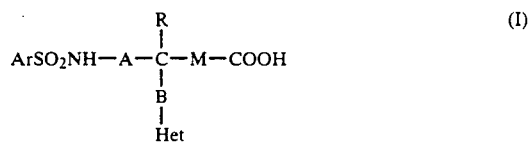

wherein A represents lower alkylene; B represents oxygen, sulfur, lower alkylene, lower alkylene interrupted by oxygen, sulfur, sulfinyl or sulfonyl, (oxy-, sulfinyl-, sulfonyl- or thio)-lower alkylene, lower alkenylene, phenylene or a direct bond; M represents lower alkylene, lower alkylene interrupted by oxygen, sulfur, sulfinyl or sulfonyl, (oxy-, sulfinyl, sulfonyl- or thio)-lower alkylene, lower alkenylene or a direct bond; or one of A, B and M represents lower alkylidenylene and the other two independently represent lower alkylene; R represents hydrogen unless A, B or M represents lower alkylidenylene in which case R represents the second bond to the adjacent alkylidenylene unsaturated carbon atom; Het represents 1-imidazolyl, 3-pyridyl, or 1-imidazolyl or 3-pyridyl substituted by lower alkyl; Ar represents carbocyclic or heterocyclic aryl; pharmaceutically acceptable ester and amide derivatives thereof; N-oxides of the said compounds wherein Het represents optionally substituted pyridyl; and pharmaceutically acceptable salts thereof.

A particular embodiment of the invention is concerned with compounds of formula Ia

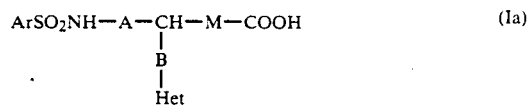

wherein A represents lower alkylene; B represents oxygen, sulfur, (oxy-, sulfinyl-, sulfonyl- or thio)-lower alkylene, lower alkylene, lower alkenylene, phenylene or a direct bond; M represents lower alkylene, lower alkylene interrupted by oxygen, sulfur, sulfinyl or sulfonyl, (oxy-, sulfinyl-, sulfonyl- or thio)-lower alkylene, lower alkenylene or a direct bond; Het represents 1-imidazolyl, 3-pyridyl, or 1-imidazolyl or 3-pyridyl substituted by lower alkyl; Ar represents carbocyclic or heterocyclic aryl; pharmaceutically acceptable ester and amide derivatives thereof; N-oxides of said compounds wherein Het represents optionally substituted pyridyl; and pharmaceutically acceptable salts thereof.

A further preferred embodiment of the invention relates to the compounds of formula II

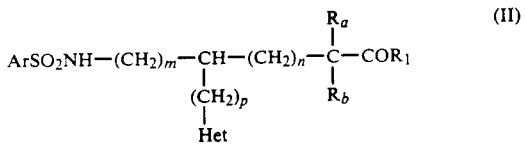

(II)

wherein Ar represents carbocyclic aryl; Het represents 1-imidazolyl, 3-pyridyl, or 1-imidazolyl or 3-pyridyl substituted by lower alkyl; m represents an integer from 1 to 5 inclusive; n represents zero or an integer from 1 to 4 inclusive; p represents zero or an integer from 1 to 5 inclusive; $COR_1$ represents carboxy or carboxy derivatized in the form of a pharmaceutically acceptable ester or amide; $R_a$ and $R_b$ independently represent hydrogen or lower alkyl; N-oxides of the said compounds wherein Het represents optionally substituted pyridyl; and pharmaceutically acceptable salts thereof.

Preferred in turn are said compounds of formula II wherein $R_a$, $R_b$, Ar and Het have meaning as defined above; m represents the integer 2, 3 or 4; n represents the integer 1, 2 or 3; p represents the integer 1, 2 or 3; $COR_1$ represents carboxy or carboxy derivatized in the form of a phamaceutically acceptable ester or amide; and pharmaceutically acceptable salts thereof.

Further preferred are any above-cited compounds wherein in formula II the sum of m and n (m+n) is 4, 5 or 6; and the sum of n and p (n+p) is 3, 4, 5 or 6. Most advantageously the sum of m and n is 5 and the sum of n and p is 4.

Illustrative embodiments relate to the above compounds wherein in formula II (a) m represents 1, n represents 4 and p represents zero;
(b) m represents 2, n represents 3 and p represents 1;
(c) m represents 3, n represents 2 and p represents 2;
(d) m represents 4, n represents 1 and p represents 3;
(e) m represents 5, n represents zero and p represents 4.

Preferred in turn are the compounds represented by groups (b), (c) and (d). Particularly preferred are those represented by group (d).

A further embodiment of the invention relates to the compounds of formula III $$ArSO_2NH-(CH_2)_m-CH-(CH_2)_q-CH=CH-COR_1 \quad (III)$$
$$| \atop (CH_2)_p \atop | \atop Het$$

wherein Ar represents carbocyclic aryl; Het represents 1-imidazolyl, 3-pyridyl, or 1-imidazolyl or 3-pyridyl substituted by lower alkyl; m represents an integer from 1 to 5 inclusive; q represents zero or an integer from 1 to 3 inclusive; p represents zero or an integer from 1 to 5 inclusive; $COR_1$ represents carboxy or carboxy derivatized in the form of a pharmaceutically acceptable ester or amide; N-oxides of the said compounds wherein Het represents optionally substituted pyridyl; and pharmaceutically acceptable salts thereof.

Another embodiment of the invention relates to the compounds of formula IIIa

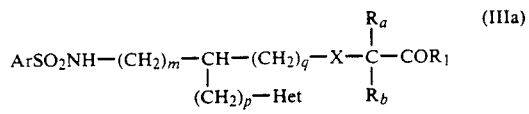

(IIIa)

wherein Ar represents carbocyclic aryl; Het represents 1-imidazolyl, 3-pyridyl or 1-imidazolyl or 3-pyridyl substituted by lower alkyl; X represents oxygen or sulfur; m represents an integer from 1 to 5; q represents zero or an integer from 1 to 3; p represents zero or an integer from 1 to 5; $COR_1$ represents carboxy or carboxy derivatized in the form of a pharmaceutically acceptable ester or amide; $R_a$ and $R_b$ represent independently hydrogen or lower alkyl; N-oxides of the said compounds wherein Het represents optionally substituted pyridyl; and pharmaceutically acceptable salts thereof.

Preferred in turn are the said compounds of formula III and IIIa wherein m represents the integer 2, 3 or 4; q represents zero or the integer 1; p represents the integer 1, 2 or 3; Ar, Het, X, $R_a$ and $R_b$ have meaning as defined above; $COR_1$ represents carboxy or carboxy derivatized in the form of a pharmaceutically acceptable ester or amide; and pharmaceutically acceptable salts thereof.

Further preferred are any above-cited compounds wherein in formula III and IIIa the sum of m and q (m+q) is 3, 4 or 5; and the sum of p and q (p+q) is 2, 3 or 4. Most advantageously the sum of m and q is 4 and the sum of p and q is 3.

Illustrative embodiments relate to the above compounds wherein in formula III and IIIa (a) m represents 1, q represents 3 and p represents zero;
(b) m represents 2, q represents 2 and p represents 1;
(c) m represents 3, q represents 1 and p represents 2;
(d) m represents 4, q represents zero and p represents 3;
(e) m represents 5, q represents zero and p represents 4.

Particularly preferred are those represented by group (d).

A further embodiment of the invention relates to the compounds of the formula IIIb

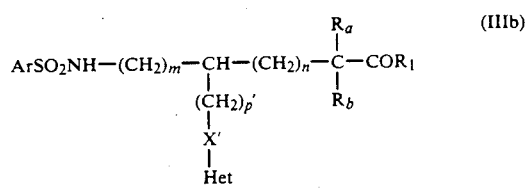

(IIIb)

wherein Ar represents carbocyclic aryl; Het represents 3-pyridyl, 1-imidazolyl, or 1-imidazolyl or 3-pyridyl substituted by lower alkyl; X' represents oxygen or sulfur; m represents an integer from 1 to 5; n represents zero or an integer from 1 to 4; p' represents zero or an integer from 1 to 4; $COR_1$ represents carboxy or carboxy derivatized in the form of a pharmaceutically acceptable ester or amide; $R_a$ and $R_b$ represent independently hydrogen or lower alkyl; N-oxides of said compounds wherein Het represents optionally substituted pyridyl; and pharmaceutically acceptable salts thereof.

Preferred in turn are the said compounds of formula IIIb wherein m represents the integer 2, 3 or 4; n represents the integer 1, 2 or 3; p' represents zero or the integer 1, 2 or 3; Ar, Het, X', $R_a$ and $R_b$ have meaning as defined above; $COR_1$ represents carboxy or carboxy derivatized in the form of a pharmaceutically acceptable ester or amide; and pharmaceutically acceptable salts thereof.

Further preferred are any above-cited compounds wherein in formula IIIb the sum of m and n (m+n) is 4, 5 or 6; and the sum of p' and n (p'+n) is 2, 3 or 4. Most advantageously the sum of m and n is 5 and the sum of p' and n is 3.

Illustrative embodiments relate to the above compounds wherein in formula IIIb, e.g.

(a) m represents 1, n represents 4 and p' represents zero;

(b) m represents 2, n represents 3 and p' represents zero;

(c) m represents 3, n represents 2 and p' represents 1;

(d) m represents 4, n represents 1 and p' represents 2;

(e) m represents 5, n represents zero and p' represents 3;

(f) m represents 3, n represents 2 and p' represents zero.

Particularly preferred are those represented by group (d).

In all the above types of compounds free carboxylic acids and esters, e.g. the compounds of formula II, III, IIIa and IIIb wherein $COR_1$ represents carboxy or carboxy esterified in form of a pharmaceutically acceptable ester, are preferred. Also preferred are compounds wherein $COR_1$ represents carbamoyl.

Furthermore compounds wherein Het represents pyridyl or pyridyl substituted by lower alkyl are preferred.

A particular embodiment of the compounds of formula II relates to the compounds of formula IV

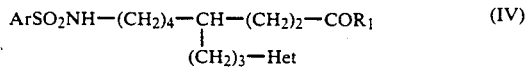
(IV)

wherein Ar represents carbocyclic aryl; $COR_1$ represents carboxy or carboxy derivatized in the form of a pharmaceutically acceptable ester or amide; Het represents 1-imidazolyl or 3-pyridyl, or 1-imidazolyl or 3-pyridyl substituted by lower alkyl, or the pyridyl-N-oxide thereof; and pharmaceutically acceptable salts thereof.

Preferred are the compounds of formula IV wherein Ar represents 1- or 2-naphthyl, phenyl or phenyl substituted by one or two substituents selected from halogen, trifluoromethyl, hydroxy, lower alkyl-(thio, sulfinyl or sulfonyl), lower alkoxy, lower alkyl, nitro, azido, amino, cyano, carboxy and lower alkoxycarbonyl; Het represents 3-pyridyl or 3-pyridyl substituted by lower alkyl, or the N-oxide thereof; $COR_1$ represents carboxy, carboxy esterified in the form of a pharmaceutically acceptable ester, or $COR_1$ represents carbamoyl; and pharmaceutically acceptable salts thereof.

Further preferred are said compounds of formula IV wherein Ar represents 2-naphthyl, phenyl or phenyl substituted by lower alkyl, halogen, cyano or trifluoromethyl; Het represents 3-pyridyl; $R_1$ represents hydroxy, lower alkoxy or amino; and pharmaceutically acceptable salts thereof.

Particularly preferred are the compounds of formula IV wherein Ar represents phenyl, chlorophenyl, fluorophenyl, tolyl or trifluoromethylphenyl; Het represents 3-pyridyl; $R_1$ represents hydroxy or lower alkoxy; and pharmaceutically acceptable salts thereof.

Another particular embodiment of the compounds of formula II relates to the compounds of formula IVa

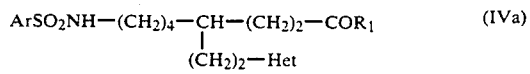
(IVa)

wherein Ar represents carbocyclic aryl; $COR_1$ represents carboxy or carboxy derivatized in the form of a pharmaceutically acceptable ester or amide; Het represents 1-imidazolyl or 3-pyridyl, or 1-imidazolyl or 3-pyridyl substituted by lower alkyl, or the pyridyl-N-oxide thereof; and pharmaceutically acceptable salts thereof.

Preferred are the compounds of formula IVa wherein Ar represents 1- or 2-naphthyl, phenyl or phenyl substituted by one or two substituents selected from halogen, trifluoromethyl, hydroxy, lower alkyl-(thio, sulfinyl or sulfonyl), lower alkoxy, lower alkyl, nitro, azido, amino, cyano, carboxy and lower alkoxycarbonyl; Het represents 3-pyridyl or 3-pyridyl-N-oxide; $COR_1$ represents carboxy, carboxy esterified in the form of a pharmaceutically acceptable ester, or carbamoyl; and pharmaceutically acceptable salts thereof.

Further preferred are said compounds of formula IVa wherein Ar represents 2-naphthyl, phenyl or phenyl substituted by lower alkyl, halogen, cyano or trifluoromethyl; Het represents 3-pyridyl; $R_1$ represents hydroxy, lower alkoxy or amino; and pharmaceutically acceptable salts thereof.

Particularly preferred are the compounds of formula IVa wherein Ar represents phenyl, chlorophenyl, fluoro-phenyl, tolyl or trifluoromethylphenyl; Het represents 3-pyridyl; $R_1$ represents hydroxy or lower alkoxy; and pharmaceutically acceptable salts thereof.

A further particular embodiment of the compounds of formula II relates to the compounds of formula V

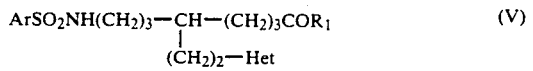
(V)

wherein Ar represents carbocyclic aryl; $COR_1$ represents carboxy or carboxy derivatized in the form of a pharmaceutically acceptable ester or amide; Het represents 1-imidazolyl or 3-pyridyl, or 1-imidazolyl or 3-pyridyl substituted by lower alkyl, or the pyridyl-N-oxide thereof; and pharmaceutically acceptable salts thereof.

Preferred are the compounds of formula V wherein Ar represents 1- or 2-naphthyl, phenyl or phenyl substituted by one or two substituents selected from halogen, trifluoromethyl, hydroxy, lower alkyl-(thio, sulfinyl or sulfonyl), lower alkoxy, lower alkyl, nitro, azido, amino, cyano, carboxy and lower alkoxycarbonyl; Het represents 3-pyridyl or 3-pyridyl-N-oxide; $COR_1$ represents carboxy, carboxy esterified in the form of a pharmaceutically acceptable ester, or carbamoyl; and pharmaceutically acceptable salts thereof.

Further preferred are said compounds of formula V wherein Ar represents 2-naphthyl, phenyl or phenyl substituted by lower alkyl, halogen, cyano or trifluoromethyl; Het represents 3-pyridyl; $R_1$ represents hydroxy, lower alkoxy or amino; and pharmaceutically acceptable salts thereof.

Particularly preferred are the compounds of formula V wherein Ar represents phenyl, chlorophenyl, fluorophenyl, tolyl or trifluoromethylphenyl; Het represents 3-pyridyl; $R_1$ represents hydroxy or lower alkoxy; and pharmaceutically acceptable salts thereof.

Another particular embodiment of the compounds of formula II relates to the compounds of formula VI

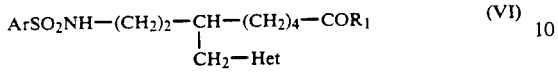

wherein Ar represents carbocyclic aryl; $COR_1$ represents carboxy or carboxy derivatized in the form of a pharmaceutically acceptable ester or amide; Het represents 1-imidazolyl or 3-pyridyl, or 1-imidazolyl or 3-pyridyl substituted by lower alkyl, or the pyridyl-N-oxide thereof; and pharmaceutically acceptable salts thereof.

Preferred are the compounds of formula VI wherein Ar represents 1- or 2-naphthyl, phenyl or phenyl substituted by one or two substituents selected from halogen, trifluoromethyl, hydroxy, lower alkyl-(thio, sulfinyl or sulfonyl), lower alkoxy, lower alkyl, nitro, azido, amino, cyano, carboxy and lower alkoxycarbonyl; Het represents 3-pyridyl or 3-pyridyl-N-oxide; $COR_1$ represents carboxy, carboxy esterified in the form of a pharmaceutically acceptable ester, or carbamoyl; and pharmaceutically acceptable salts thereof.

Further preferred are said compounds of formula VI wherein Ar represents 2-naphthyl, phenyl or phenyl substituted by lower alkyl, halogen, cyano or trifluoromethyl; Het represents 3-pyridyl; $R_1$ represents hydroxy, lower alkoxy or amino; and pharmaceutically acceptable salts thereof.

Particularly preferred are the compounds of formula VI wherein Ar represents phenyl, chlorophenyl, fluorophenyl, tolyl or trifluoromethylphenyl; Het represents 3-pyridyl; $R_1$ represents hydroxy or lower alkoxy; and pharmaceutically acceptable salts thereof.

A further particular embodiment of the compounds of formula II relates to the compounds of formula VII

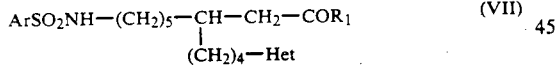

wherein Ar represents carbocyclic aryl; $COR_1$ represents carboxy or carboxy derivatized in the form of a pharmaceutically acceptable ester or amide; Het represents 1-imidazolyl or 3-pyridyl, or 1-imidazolyl or 3-pyridyl substituted by lower alkyl or the pyridyl-N-oxide thereof; and pharmaceutically acceptable salts thereof.

Preferred are the compounds of formula VII wherein Ar represents 1- or 2-naphthyl, phenyl or phenyl substituted by one or two substituents selected from halogen, trifluoromethyl, hydroxy, lower alkyl-(thio, sulfinyl or sulfonyl, lower alkoxy, lower alkyl, nitro, azido, amino, cyano, carboxy and lower alkoxycarbonyl; Het represents 3-pyridyl or 3-pyridyl-N-oxide; $COR_1$ represents carboxy, carboxy esterified in the form of a pharmaceutically acceptable ester, or carbamoyl; and pharmaceutically acceptable salts thereof.

Further preferred are said compounds of formula VII wherein Ar represents 2-naphthyl, phenyl or phenyl substituted by lower alkyl, halogen, cyano or trifluoromethyl; Het represents 3-pyridyl; $R_1$ represents hydroxy, lower alkoxy or amino; and pharmaceutically acceptable salts thereof.

Particularly preferred are the compounds of formula VII wherein Ar represents phenyl, chlorophenyl, fluorophenyl, tolyl or trifluoromethylphenyl; Het represents 3-pyridyl; $R_1$ represents hydroxy or lower alkoxy; and pharmaceutically acceptable salts thereof.

Another particular embodiment of the compounds of formula Ia relates to the compounds of formula VIII

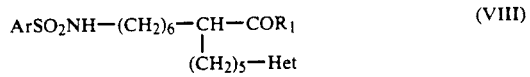

wherein Ar represents carbocyclic aryl; $COR_1$ represents carboxy or carboxy derivatized in the form of a pharmaceutically acceptable ester or amide; Het represents 1-imidazolyl, 3-pyridyl, or 1-imidazolyl or 3-pyridyl substituted by lower alkyl, or the pyridyl-N-oxide thereof; and pharmaceutically acceptable salts thereof.

Preferred are the compounds of formula VIII wherein Ar represents 1- or 2-naphthyl, phenyl or phenyl substituted by one or two substituents selected from halogen, trifluoromethyl, hydroxy, lower alkyl-(thio, sulfinyl or sulfonyl), lower alkoxy, lower alkyl, nitro, azido, amino, cyano, carboxy and lower alkoxycarbonyl; Het represents 3-pyridyl or 3-pyridyl-N-oxide; $COR_1$ represents carboxy, carboxy esterified in the form of a pharmaceutically acceptable ester, or carbamoyl; and pharmaceutically acceptable salts thereof.

Further preferred are said compounds of formula VIII wherein Ar represents 2-naphthyl, phenyl or phenyl substituted by lower alkyl, halogen, cyano or trifluoromethyl; Het represents 3-pyridyl; $R_1$ represents hydroxy, lower alkoxy or amino; and pharmaceutically acceptable salts thereof.

Particularly preferred are the compounds of formula VIII wherein Ar represents phenyl, chlorophenyl, fluoro-phenyl, tolyl or trifluoromethylphenyl; Het represents 3-pyridyl; $R_1$ represents hydroxy or lower alkoxy; and pharmaceutically acceptable salts thereof.

A further particular embodiment of the compounds of formula II relates to the compounds of formula IX

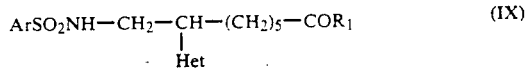

wherein Ar represents carbocyclic aryl; $COR_1$ represents carboxy or carboxy derivatized in the form of a pharmaceutically acceptable ester or amide; Het represents 1-imidazolyl, 3-pyridyl, or 1-imidazolyl or 3-pyridyl substituted by lower alkyl, or the pyridyl-N-oxide thereof; and pharmaceutically acceptable salts thereof.

Preferred are the compounds of formula IX wherein Ar represents 1- or 2-naphthyl, phenyl or phenyl substituted by one or two substituents selected from halogen, trifluoromethyl, hydroxy, lower alkyl-(thio, sulfinyl or sulfonyl), lower alkoxy, lower alkyl, nitro, azido, amino, cyano, carboxy and lower alkoxycarbonyl; Het represents 3-pyridyl or 3-pyridyl-N-oxide; $COR_1$ represents carboxy, carboxy esterified in the form of a pharmaceutically acceptable ester, or carbamoyl; and pharmaceutically acceptable salts thereof.

Further preferred are said compounds of formula IX wherein Ar represents 2-naphthyl, phenyl or phenyl substituted by lower alkyl, halogen, cyano or trifluoromethyl; Het represents 3-pyridyl; $R_1$ represents hydroxy, lower alkoxy or amino; and pharmaceutically acceptable salts thereof.

Particularly preferred are the compounds of formula IX wherein Ar represents phenyl, chlorophenyl, fluorophenyl, tolyl or trifluoromethylphenyl; Het represents 3-pyridyl; $R_1$ represents hydroxy or lower alkoxy; and pharmaceutically acceptable salts thereof.

A particular embodiment of the compounds of formula IIIa relates to the compounds of formula X

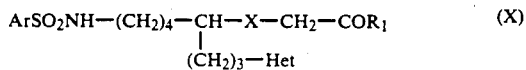

wherein Ar represents carbocyclic aryl; $COR_1$ represents carboxy or carboxy derivatized in the form of a pharmaceutically acceptable ester or amide; Het represents 1-imidazolyl, 3-pyridyl, or 1-imidazolyl or 3-pyridyl substituted by lower alkyl, or the pyridyl-N-oxide thereof; X represents oxygen or sulfur; and pharmaceutically acceptable salts thereof.

Preferred are the compounds of formula X wherein Ar represents 1- or 2-naphthyl, phenyl or phenyl substituted by one or two substituents selected from halogen, trifluoromethyl, hydroxy, lower alkyl-(thio, sulfinyl or sulfonyl), lower alkoxy, lower alkyl, nitro, azido, amino, cyano, carboxy and lower alkoxycarbonyl; Het represents 3-pyridyl or 3-pyridyl-N-oxide; X represents oxygen or sulfur; $COR_1$ represents carboxy, carboxy esterified in the form of a pharmaceutically acceptable ester, or carbamoyl; and pharmaceutically acceptable salts thereof.

Further preferred are said compounds of formula X wherein Ar represents 2-naphthyl, phenyl or phenyl substituted by lower alkyl, halogen, cyano or trifluoromethyl; Het represents 3-pyridyl; X represents oxygen or sulfur; $R_1$ represents hydroxy, lower alkoxy or amino; and pharmaceutically acceptable salts thereof.

Particularly preferred are the compounds of formula X wherein Ar represents phenyl, chlorophenyl, fluorophenyl, tolyl or trifluoromethylphenyl; Het represents 3-pyridyl; $R_1$ represents hydroxy or lower alkoxy; X represents oxygen or sulfur; and pharmaceutically acceptable salts thereof.

A specific embodiment thereof relates to the compounds of formula X wherein X represents oxygen.

Another specific embodiment relates to the compounds of formula X wherein X represents sulfur.

A particular embodiment of the compounds of formula IIIb relates to the compounds of formula Xa

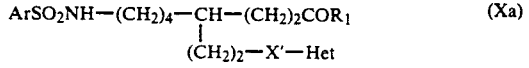

wherein Ar represents carbocyclic aryl; $COR_1$ represents carboxy or carboxy derivatized in the form of a pharmaceutically acceptable ester or amide; Het represents 3-pyridyl or 3-pyridyl substituted by lower alkyl, or the N-oxide thereof; X' represents oxygen or sulfur; and pharmaceutically acceptable salts thereof.

Preferred are the compounds of formula Xa wherein Ar represents 1- or 2-naphthyl, phenyl or phenyl substituted by one or two substituents selected from halogen, trifluoromethyl, hydroxy, lower alkyl-(thio, sulfinyl or sulfonyl), lower alkoxy, lower alkyl, nitro, azido, amino, cyano, carboxy and lower alkoxycarbonyl; Het represents 3-pyridyl or 3-pyridyl-N-oxide; X' represents oxygen or sulfur; $COR_1$ represents carboxy, carboxy esterified in the form of a pharmaceutically acceptable ester, or carbamoyl; and pharmaceutically acceptable salts thereof.

Further preferred are said compounds of formula Xa wherein Ar represents 2-naphthyl, phenyl or phenyl substituted by lower alkyl, halogen, cyano or trifluoromethyl; Het represents 3-pyridyl; X' represents oxygen or sulfur; $R_1$ represents hydroxy, lower alkoxy or amino; and pharmaceutically acceptable salts thereof.

Particularly preferred are the compounds of formula Xa wherein Ar represents phenyl, chlorophenyl, fluorophenyl, tolyl or trifluoromethylphenyl; Het represents to 3-pyridyl; $R_1$ represents hydroxy or lower alkoxy; X' represents oxygen or sulfur; and pharmaceutically acceptable salts thereof.

A specific embodiment thereof relates to the compounds for formula Xa wherein X' represents oxygen. Another specific embodiment relates to the compounds of formula Xa wherein X' represents sulfur.

A further particular embodiment of the invention relates to the compounds of formula

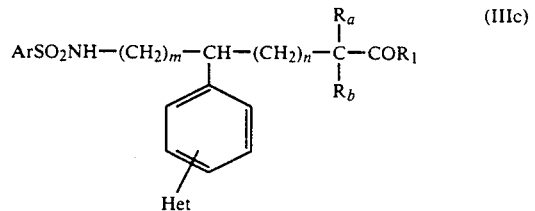

wherein Ar represents carbocyclic aryl; Het is located at the meta or para position and represents 3- pyridyl or 3-pyridyl substituted by lower alkyl; m represents an integer from 1 to 5; n represents zero or an integer from 1 to 4; $COR_1$ represents carboxy or carboxy derivatized in the form of a pharmaceutically acceptable ester or amide; $R_a$ and $R_b$ represent independently hydrogen or lower alkyl; and pharmaceutically acceptable salts thereof.

Preferred in turn are said compounds of the formula IIIc wherein m represents the integer 2, 3 or 4; n represents the integer 1, 2 or 3; Ar, Het, $COR_1$, $R_a$ and $R_b$ have meaning as defined above, and pharmaceutically acceptable salts thereof.

Particularly preferred are said compounds wherein the sum of m and n is 3, 4 or 5, advantageously 5.

Most preferred are compounds of formula IIIc wherein m represents 4; n represents 1; Ar represents 2-naphthyl, phenyl or phenyl substituted by lower alkyl, halogen, cyano, or trifluoromethyl; Het represents 3-pyridyl; $COR_1$ represents carboxy, lower alkoxycarbonyl or carbamoyl; $R_a$ and $R_b$ represent hydrogen; and pharmaceutically acceptable salts thereof. Particularly preferred are said compounds wherein Ar represents phenyl, chlorophenyl, fluorophenyl, tolyl or trifluoromethylphenyl.

Another particular embodiment of the invention relates to the compounds of formula I wherein one of A, B and M represents lower alkylidenylene and the other two represent lower alkylene; Ar represents carbocyclic aryl; Het represents 3-pyridyl or 3-pyridyl substituted by lower alkyl; R represents the second bond to the adjacent alkylidenylene unsaturated carbon atom; pharmaceutically acceptable ester and amide derivatives thereof; and pharmaceutically acceptable salts thereof.

Preferred are said compounds wherein the alkylidenylene or alkylene chain in A, B and M has 1 to 5 carbon atoms. Particularly preferred are said compounds wherein A has 4 carbon atoms in chain, B has 3 carbon atoms in chain and M has 2 carbon atoms in chain. Further preferred are said compounds wherein A represents alkylidenylene and B and M represent lower alkylene.

The present invention further relates to tetrazoles of the formula

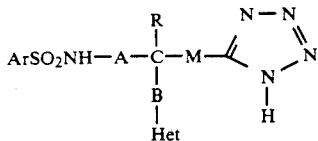

(Ib)

wherein Ar, A, R, B, M and Het have meaning as defined for formula I above; and pharmaceutically acceptable salts thereof.

Similarly the invention relates to the tetrazoles corresponding to compounds as further defined above by structural formulae hereinabove but wherein the terminal grouping (COOH or COR$_1$) is replaced by 5-tetrazolyl.

For example, a particular embodiment thereof relates to the compounds of formula IVb

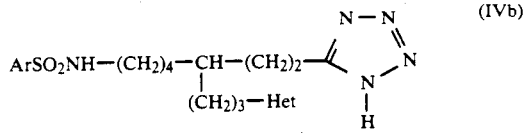

(IVb)

wherein Ar and Het have meaning as defined above for compounds of formula IV; and pharmaceutically acceptable salts thereof.

Particular embodiments of the invention relate to the compounds of the invention, e.g. of formula I, Ia, Ib, II, III, IIIa, IIIb and derivatives wherein Het represents optionally substituted 3-pyridyl and optionally substituted 1-imidazolyl, respectively.

Preferred are any said compounds wherein Het represents 3-pyridyl or 3-pyridyl substituted by lower alkyl.

The present invention thus also relates to the corresponding 1-imidazolyl compounds analogous to all the above pyridyl substituted embodiments of formula IV to Xb, but wherein Het represents 1-imidazolyl or 1-imidazolyl substituted by lower alkyl, with other groups having meaning as defined.

For example, a particular embodiment of the invention relates to compounds of formula IV

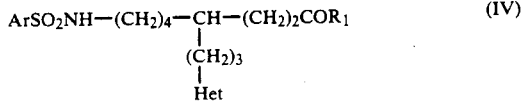

(IV)

wherein Ar represents carbocyclic aryl; COR$_1$ represents carboxy or carboxy derivatized in the form of a pharmaceutically acceptable ester or amide; Het represents 1-imidazolyl or 1-imidazolyl substituted by lower alkyl; and pharmaceutically acceptable salts thereof.

Preferred are the said compounds of formula IV wherein Ar represents 1- or 2-naphthyl, phenyl or phenyl substituted by one or two substituents selected from halogen, trifluoromethyl, hydroxy, lower alkyl-(thio, sulfinyl or sulfonyl), lower alkoxy, lower alkyl, nitro, azido, amino, cyano, carboxy and lower alkoxycarbonyl; Het represents 1-imidazolyl; COR$_1$ represents carboxy, carboxy esterified in the form of a pharmaceutically acceptable ester, or carbamoyl; and pharmaceutically acceptable salts thereof.

Further preferred are the said compounds of formula IV wherein Ar represents 2-naphthyl, phenyl or phenyl substituted by lower alkyl, halogen, cyano or trifluoromethyl; Het represents 1-imidazolyl; R$_1$ represents hydroxy, lower alkoxy or amino; and pharmaceutically acceptable salts thereof.

Particularly preferred are the said compounds of formula IV wherein Ar represents phenyl, chlorophenyl, fluorophenyl, tolyl or trifluoromethylphenyl; Het represents 1-imidazolyl; R$_1$ represents hydroxy or lower alkoxy; and pharmaceutically acceptable salts thereof.

The term "lower" when referred to above and hereinafter in connection with organic groups, radicals or compounds respectively defines such with up to and including 7, preferably up to and including 4 and advantageously one, two or three carbon atoms.

Lower alkyl preferably contains 1–4 carbon atoms and represents for example ethyl, propyl, butyl or advantageously methyl.

Lower alkoxy preferably contains 1–4 carbon atoms and represents for example, ethoxy, propoxy or advantageously methoxy.

Lower alkoxycarbonyl preferably contains 1–4 carbon atoms in the alkoxy portion and represents for example: methoxycarbonyl, propoxycarbonyl, isopropoxycarbonyl or advantageously ethoxycarbonyl.

Lower alkylene, which may be straight chain or branched represents $C_1$–$C_7$-alkylene, preferably $C_1$–$C_5$-alkylene, particularly methylene, ethylene, propylene, butylene or pentylene.

Oxy-, sulfinyl-, sulfonyl- or thio-lower alkylene for group M represents such wherein in formula I or Ia the oxygen or sulfur end is attached to central carbon; for group B said term represents such wherein the oxygen or sulfur end is attached to central carbon or group Het, advantageously the oxygen or sulfur end being attached to group Het.

Lower alkenylene which may be straight chain or branched represents $C_2$–$C_7$-alkenylene, preferably ethenylene, propenylene, 1- or 2-butenylene or 1- or 2-pentenylene.

Lower alkylidenylene represents straight chain or branched $C_1$–$C_7$-alkylidenylene, preferably straight chain ethylidenylene, propylidenylene, butylidenylene in which the double bond is attached to the central carbon atom in formula I (and R represents a bond to the terminal carbon atom of alkylidenylene grouping).

Phenylene represents ortho-, meta- or para-phenylene, preferably meta- or para-phenylene.

Halogen is preferably fluorine, chlorine, but may also represent bromine or iodine.

Carbocyclic aryl represents preferably 1- or 2-naphthyl naphthyl or phenyl, or said 1- or 2-naphthyl or phenyl substituted by one to three, preferably 1 or 2 substituents selected from halogen, trifluoromethyl, hydroxy, lower alkyl-(thio, sulfinyl or sulfonyl), lower alkoxy, lower alkyl, nitro, azido, amino, cyano, carboxy or carboxy derivatized in the form of a pharmaceutically acceptable ester or amide. Further preferred is phenyl or phenyl substituted, advantageously at the para position, by lower alkyl, halogen, cyano or trifluoromethyl.

Heterocyclic aryl represents preferably thienyl, pyridyl, quinolinyl or isoquinolinyl optionally substituted (on a ring carbon atom) by e.g. lower alkyl, lower alkoxy or halogen. Thienyl represents preferably 2- or 3-thienyl. Pyridyl represents preferably 3-pyridyl. Isoquinolinyl represents preferably 5-isoquinolinyl. Quinolinyl represents preferably 8-quinolinyl.

Imidazolyl or pyridyl substituted by lower alkyl represents a said radical substituted on a ring carbon atom preferably by $C_1$-$C_3$-alkyl, advantageously methyl.

Carboxy esterified in form of a pharmaceutically acceptable ester represents advantageously a prodrug ester that may be convertible by solvolysis or under physiological conditions to the free carboxylic acid, e.g. lower alkoxycarbonyl; (amino, mono- or di-lower alkylamino) substituted lower alkoxycarbonyl; carboxy-substituted lower alkoxycarbonyl, e.g. alpha-carboxy-substituted lower alkoxycarbonyl; lower alkoxycarbonyl-substituted lower alkoxycarbonyl, e.g. alpha-lower alkoxycarbonyl-substituted lower alkoxycarbonyl; aryl-substituted lower alkoxycarbonyl, e.g. optionally substituted benzyloxycarbonyl or pyridylmethoxycarbonyl; (hydroxy, lower alkanoyloxy or lower alkoxy)-substituted lower alkoxy carbonyl, e.g. pivaloyloxymethoxycarbonyl; (hydroxy, lower alkanoyloxy or lower alkoxy)-substituted lower alkoxymethoxycarbonyl; bicycloalkoxycarbonyl-substituted lower alkoxycarbonyl, e.g. bicyclo[2,2,1]-heptyloxycarbonyl-substituted lower alkoxycarbonyl, especially bicyclo[2,2,1]-heptyloxycarbonyl-substituted methoxycarbonyl such as bornyloxycarbonylmethoxycarbony; 3-phthalidoxycarbonyl; (lower alkyl, lower alkoxy, halo)-substituted 3-phthalidoxycarbonyl; lower alkoxycarbonyloxy-lower alkoxycarbonyl, e.g. 1-(methoxy- or ethoxycarbonyloxy)-ethoxycarbonyl; aryloxycarbonyl, e.g. phenoxycarbonyl or 3-pyridyloxycarbonyl.

Preferred as prodrug esters are e.g. the lower alkyl, pivaloyloxymethyl, 2-diethylaminoethyl, bornyloxycarbonylmethyl esters. Lower alkyl esters are for example the methyl, ethyl, propyl, isopropyl, isobutyl and neopentyl esters.

Carboxy derivatized in the form of a pharmaceutically acceptable amide represents preferably simple primary, secondary and tertiary amides and amides derived from amino acids such as glycine, alanine and the like.

Secondary and tertiary amides are those wherein carboxy derivatized in the form of a pharmaceutical amide represents preferably mono- and di-lower alkylcarbamoyl, for example N-methyl-, N-ethyl-, N,N-dimethyl- and N,N-diethyl-carbamoyl.

Preferred amides are those wherein carboxy derivatized as an amide represents carbamoyl and mono-lower alkylcarbamoyl.

An N-oxide represents pyridyl N-oxide or lower alkyl-substituted pyridyl N-oxide.

Pharmaceutically acceptable salts are preferably metal or ammonium salts of said compounds of formula I having a free carboxy group, more particularly alkali or alkaline earth metal salts, e.g., the sodium, potassium, magnesium or calcium salt; or advantageously easily crystallizing ammonium salts derived from ammonia or organic amines, such as mono-, di- or tri-lower (alkyl, cycloalkyl or hydroxyalkyl)-amines, lower alkylenediamines or mono-, di- or tri-hydroxy-lower alkyl amines, e.g., methylamine, diethylamine, triethylamine, dicyclohexylamine, triethanolamine, ethylenediamine, or tris-(hydroxymethyl)methylamine. Said compounds of Formula I form acid addition salts of preferably the pharmaceutically acceptable inorganic or organic acids, such as of strong mineral acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycolic, lactic, malic, tartaric, gluconic, citric, ascorbic, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic or cyclohexylsulfamic acid.

The compounds of the invention exhibit valuable pharmacological properties, e.g. by selectively inhibiting thromboxane synthetase activity and blocking thromboxane receptor activity in mammals. The compounds are thus useful for treating disorders responsive to thromboxane synthetase inhibition and to thromboxane receptor antagonist activity in mammals, primarily cardiovascular disorders such as thrombosis, atherosclerosis, cerebral infarctions (strokes), myocardial infarctions (heart attacks), and other occlusive vascular conditions.

The novel compounds of the invention are active in state of the art in vitro and in vivo test systems, indicative of thromboxane receptor antagonist activity and thromboxane synthetase inhibitory activity.

The above-cited properties are demonstrable in vitro and in vivo tests, using advantageously mammals, e.g. guinea pigs, rats, dogs, monkeys, rabbits or isolated organs, tissues and blood preparations thereof, as well as with human blood (e.g. platelet) preparations. Said compounds can be applied in vitro in the form of solutions, e.g. preferably aqueous solutions, and in vivo either enterally or parenterally advantageously orally or intravenously, e.g. within gelatin capsules, as starch suspensions or in aqueous solutions. The dosage in vitro may range between about $10^{-5}$ molar and $10^{-9}$ molar concentrations, preferably between about $10^{-7}$ and $10^{-9}$ molar concentrations. The dosage in vivo may range between about 0.01 and 100 mg/kg/day, preferably between about 0.1 and 50 mg/kg/day, advantageously between about 1 and 30 mg/kg/day, depending on the compound and the route of administration.

The in vitro inhibition of the thromboxane synthetase enzyme can be demonstrated, analogous to the method of Sun, Biochem. Biophys. Res. Comm. 74, 1432 (1977); the testing procedure is as follows:

$^{14}$C-Arachidonic acid is incubated with an enzyme consisting of solubilized and partially purified prostaglandin cyclo-oxygenase from sheep seminal vesicles and a crude microsomal preparation of thromboxane synthetase from lysed human platelets. The test compound (dissolved in buffer, or if necessary, in a small amount of ethanol) is added to the incubation medium. At the end of the incubation period (30 minutes), Prostaglandin E2 ($PGE_2$) is reduced to a mixture of Prostaglandin F2alpha and F2beta ($PGF_2$alpha+beta) by addition of sodium borohydride. The radioactive products and excess substrate are extracted into ethyl acetate; the extract is evaporated to dryness; the residue is dissolved in acetone, spotted on thin-layer plates and chromatographed in the solvent system toluene: acetone: glacial acetic acid (100 volumes: 100 volumes: 3 volumes). The radioactive zones are located; those corresponding to Thromboxane $B_2(T \times B_2)$ and PGF$_2$alpha+beta are transferred to liquid scintillation vials and counted. The ratio of counts for $T \times B_2$/PGF$_2$alpha+beta is calculated for each concentration of test compound and IC$_{50}$ values are determined graphically as the concentration of test compound at which the ratio of $T \times B_2$/PGF$_2$alpha+beta is reduced to 50% of the control value.

Illustrative of the invention, the compounds of examples 5a and 31 inhibit thromboxane synthesis in vitro with an IC$_{50}$ of about $2 \times 10^{-9}$M and $2.6 \times 10^{-9}$M, respectively.

The in vitro antagonism of thromboxane receptor activity can be demonstrated e.g. as described by Le Breton et al in Proc. Nat. Acad. Sci. 76, 4097 (1979).

The inhibition of thromboxane-A$_2$ receptor activity can be determined by measuring the inhibition of U-46619 induced platelet aggregation of aspirinated human washed platelets and in human platelet rich plasma. U-46619 is (15S)-hydroxy-11-alpha,9-alpha(epoxymethano)-prosta- (5Z,13E)-dienoic acid, a thromboxane-A$_2$ receptor agonist, as described by Di Minno et al, Thromb. Haemost. 45, 103 (1981).

Illustrative of the invention the compound of example 5a inhibits thromboxane-A$_2$ receptor activity in vitro with an IC$_{50}$ of about $9 \times 10^{-9}$ M as determined by inhibition of U-46619-induced aggregation of washed platelets; IC$_{50}$ for the compound of example 31 is about $20 \times 10^{-9}$M.

Further illustrative of the invention, the in vitro IC$_{50}$ for inhibition of U-46619 induced aggregation in platelet rich plasma is about $2 \times 10^{-7}$M for the compound of example 5a and about $5 \times 10^{-7}$M for the compound of example 31.

Indicative of the beneficial effects, e.g. in occlusive cardiovascular disorders, the compounds of the invention inhibit variously experimentally induced platelet aggregation, e.g. platelet aggregation induced by collagen or U-46619. Such inhibition of platelet aggregation is determined using methodology known in the art, e.g. in vitro in the presence of a compound of the invention in human platelet rich plasma, or by measuring the inhibition of aggregation seen in plasma obtained from a mammal previously administered a compound of the invention, e.g. orally or intravenously when compared to controls. Platelet aggregation is measured in a Born aggregometer and platelet rich plasma is prepared from venous blood e.g. as described in Br. J. Haematol. 43, 637 (1979). Suitable test animals are anesthesized rats or guinea pigs and unanesthesized rabbits or cyanomolgus monkeys.

For example, the effect of the compounds of the invention in inhibiting platelet aggregation and reducing plasma levels of thromboxane can be determined as follows:

Anesthetized rats or guinea pigs are administered either the test compound or vehicle orally as a suspension in corn starch. Blood is withdrawn after 15 minutes to 1 hour, a small portion of which is incubated at 37° C. followed by radio-immunoassay to determine the serum level of thromboxane B$_2$. The major portion of the blood is processed to separate the plasma which is subjected to U-46619 or collagen-induced platelet aggregation assays as mentioned before.

Illustrative of the invention, the compound of example 5a when given orally to rats at a dose of 30 mg/kg inhibits thromboxane B$_2$ production by 90% (1 hour post dose) and inhibits collagen-induced platelet aggregation; in the guinea pig, the compound of Example 31 inhibits U-46619 induced platelet aggregation at 10 mg/Kg p.o.; also in conscious cyanomolgus monkeys, the compound of Example 5a at 30 mg/Kg p.o., and the compound of example 31 at 10 mg/kg p.o., inhibit thromboxane B2 production and inhibit U-46619 induced platelet aggregation.

The effect on plasma levels of thromboxane and prostacyclin can also be determined in vivo on administration to rats in the following manner (as adapted from the procedures described by Tai et al. in Anal. Biochem. 87:343, 1978 and by Salmon in Prostaglandins 15:383, 1978):

Rats are dosed with vehicle or test drug and injected intravenously with ionophore A23187 (0.5 mg/kg) two hours later. Blood is collected for analysis 2 minutes after the ionophore injection. A single aliquot of each plasma sample is assayed for thromboxane B$_2$ and another aliquot for 6-keto-PGFlalpha, the stable metabolites of thromboxane A$_2$ and prostacyclin (PGI$_2$) respectively, by radioimmunoassay.

The effect of the compounds of the invention on potentiating thrombolytic agents such as TPA and in preventing post-thrombolytic reocclusion can be demonstrated in anesthetized open-chest dogs in which intracoronary thrombi are produced in the circumflex coronary artery by electrically-induced injury to the intimal surface, and lysed 60 minutes later with tissue plasminogen activator (TPA, 10 ug/kg/min for 30 or 60 minutes). Dogs are treated 15 minutes prior to TPA by i.v. injection or i.v. infusion of the test compound. The decrease in the time required for reperfusion compared to TPA alone and the reduction in the incidence of reocclusion compared to TPA alone are also observed. A reduction in the effective dose of TPA is also observed. Illustrative of the invention the compound of example 5a, at a dose of about 0.5 mg/Kg i.v. administered as a bolus followed by infusion of 0.2 mg/Kg/hr for 2 hours, is effective in potentiating the effect of TPA and reducing the incidence of reocclusion.

The pulmonary effects of the compounds of the invention can be demonstrated e.g. by measuring the inhibition of bronchoconstriction induced by arachidonic acid in the anesthetized guinea pig model as described in Br J. Pharmcol. 30, 283-307 (1967).

Illustrative of the invention, the compounds of example 5a and 31 inhibit bronchoconstriction caused by prior administration of arachidonic acid (250 mcg/Kg i.v. followed by $2 \times 500$ mcg/Kg i.v.) with an ED$_{50}$ of about 6 mcg/Kg i.v. and 4.6 mcg/Kg i.v., respectively.

The aforementioned thromboxane receptor antagonist and thromboxane synthesis inhibitory properties and resulting effects render the compounds of the invention particularly useful as therapeutic agents in mammals, e.g. for the treatment of occlusive vascular conditions and conditions of bronchoconstriction.

The compounds and derivatives thereof according to the invention can be prepared by the following processes:

(a) condensing a reactive functional derivative of a sulfonic acid of the formula $$Ar-SO_3H \qquad (XI)$$

wherein Ar has meaning as defined above, with an amine of the formula

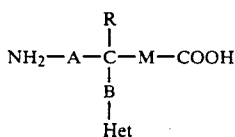

(XII)

wherein A, B, M, Het and R have meaning as defined above and the carboxy group is in protected form; or (b) condensing a compound of the formula

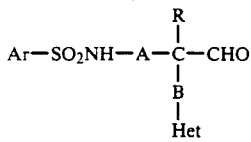

(XIII)

wherein Ar, R, A, B and Het have meaning as defined above, with a Wittig reagent to a corresponding compound of formula I wherein M represents lower alkenylene; or (c) for compounds of formula I wherein M represents a direct bond and R represents hydrogen, hydrolyzing and decarboxylating a diester of a compound of the formula

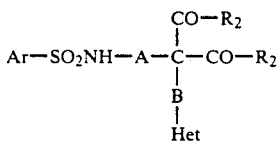

(XIV)

wherein Ar, A, B and Het have meaning as defined above, and $COR_2$ represents esterified carboxy; or (d) for compounds of formula I, e.g. wherein B represents lower alkylene and wherein Het represents 1-imidazolyl optionally substituted by lower alkyl, e.g. of the formula II, condensing a compound of the formula XV

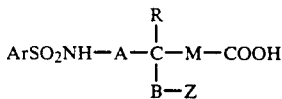

(XV)

wherein Ar, A, R, M, have meaning as defined above, B represents lower alkylene, carboxy is in protected form, $ArSO_2NH$ may be in protected form, and Z represents reactive esterified hydroxy, with imidazole or lower alkyl-substituted imidazole; or (e) for compounds of formula I wherein Het represents 3-pyridyl optionally substituted by lower alkyl and B represents O, S, oxy-lower alkylene or thio-lower alkylene, e.g. those of formula IIIb, condensing a compound of the formula XV wherein Z represents hydroxy or reactive esterified hydroxy, carboxy is preferably protected and $ArSO_2NH$ may be in protected form, with either 3-hydroxypyridine or 3-mercapto-pyridine optionally substituted by lower alkyl; or (f) for compounds of formula I wherein Het represents 3-pyridyl optionally substituted by lower alkyl and B represents lower alkenylene, condensing an aldehyde wherein in formula XV, B-Z combined represents formyl-lower alkylene, with a Wittig reagent derived from a reactive derivative of 3-hydroxymethylpyridine optionally substituted by lower alkyl; or (g) for compounds of formula I wherein Het represents 3-pyridyl optionally substituted by lower alkyl and B represents lower alkenylene, condensing an alkene wherein in formula XV, B-Z combined represents terminal lower alkenyl, with a reactive derivative of 3-hydroxypyridine or of 3-hydroxypyridine substituted by lower alkyl under conditions of a Heck reaction; or h) converting into a compound of the invention a compound of the formula XVI

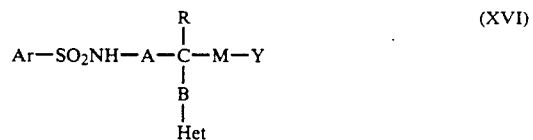

(XVI)

wherein Ar, R, A, B, Het, M have meaning as defined above, and Y is a group differing from carboxy or derivatized carboxy and convertible into such; or (i) for compounds of the invention wherein e.g. in formula I COOH is replaced by 5-tetrazolyl, condensing a compound of formula XVI, wherein Ar, R, A, B and M have meaning as defined above and Y represents cyano, with hydrazoic acid or a compound which serves as a source of hydrazoic acid, e.g. an organometallic derivative or salt thereof;

and if necessary, carrying out any of the above processes with starting materials in protected form and then removing protective groups from the resulting product; and if necessary, converting a compound of the invention obtained by any of the above processes into another compound of the invention; and if desired, converting any resulting compound of the invention into a salt thereof, or liberating a free compound from such salt; and, if desired, separating and isolating a substantially pure optical or geometric isomer from a mixture of isomeric forms of a resulting compound of the invention.

The preparation according to process (a) is carried out using well-known methodology for the preparation of a sulfonamide from an amine, by reacting preferably the appropriate arylsulfonyl halide, advantageously the chloride, in the presence of a base, such as a tertiary amine, e.g. triethylamine, 4-dimethylaminopyridine, pyridine and the like, with an amine of formula XII.

The arylsulfonyl halides are either known in the art or can be prepared according to methods well-known in the art.

The starting materials of formula XII, in particular wherein Het represents optionally substituted 3-pyridyl, e.g. as esters thereof, are prepared according to sequences appropriate to the particular type of the compound involved The following are illustrative of such procedures and can be adapted to other compounds of the invention having e.g different chain lengths.

An illustrative starting ester of a compound of formula XII suitable for the preparation of a compound of formula IV can be prepared as follows:

A di-lower alkyl ester of malonic acid, e.g. diethyl malonate, is condensed with a 3-(3-pyridyl)-propyl halide such as the bromide to obtain e.g. the di-lower alkyl [3-(3-pyridyl)-propyl]-malonate diester This is condensed under basic conditions, e.g. in the presence of a strong base such as sodium hydride with e.g. 1-bromo-4-chlorobutane to obtain the corresponding 4-chlorobutyl-substituted malonate diester which is in turn treated with sodium azide (advantageously in the presence of sodium iodide and a crown ether to obtain e.g. diethyl (4-azidobutyl)-[3-(3-pyridyl)-propyl]-malonate Reduction of the azide with e.g. triphenyl phosphine yields the di-lower alkyl (4-aminobutyl)-[3-(3-pyridyl)-propyl]-malonate diester. The malonate ester is then hydrolyzed and decarboxylated with e.g. hydrochloric acid to obtain a compound of formula XII wherein A represents 1,4-butylene, B represents 1,3-propylene, M represents a direct bond, and Het represents 3-pyridyl. The above amine is then protected e.g. as the t-Boc derivative according to standard procedures, converted to an ester, e.g. a lower alkyl ester, and reduced to the corresponding carboxaldehyde with e.g. diisobutylaluminum hydride. Wittig type condensation e.g. with a lower alkyl triphenylphosphoranylidene-acetate or with triethyl phosphonoacetate followed by hydrolysis yields the corresponding starting material of formula XII wherein A represents 1,4-butylene, B represents 1,3-propylene, Het represents 3-pyridyl and M represents 1,2-ethenylene, e.g. as the methyl ester thereof (which can be used as starting material for the preparation of a compound of formula III wherein m=4, p=3 and q=zero, or a derivative thereof).

Reduction of the alpha,beta-unsaturated ester according to known methods, e.g. with sodium borohydride in the presence of cobalt (II) chloride yields the starting amine of formula XII wherein A represents 1,4-butylene, B represents 1,3-propylene, Het represents 3-pyridyl and M represents 1,2-ethylene, e.g. as the methyl ester, which can serve as the starting material for the preparation of a compound of formula IV.

An illustrative starting ester of a compound of formula XII in racemic or in optically active form suitable for the preparation of a compound of formula IV can also be prepared as follows:

Epsilon-caprolactone is hydrolyzed to the 6-hydroxyhexanoic acid which is protected e.g. as a tri-lower alkyl silyl ether and the resulting acid (as a reactive derivative) is converted to an optically active amide by treatment with e.g. optically active 4-benzyl-2-oxazolidinone in the presence of a strong base (such as n-butyl lithium). Alkylation of the oxazolidinone derivative with allyl bromide yields after purification and reduction with lithium borohydride e.g. optically active 2-allyl-6-(trilower alkylsilyloxy)-hexanol which is converted to the corresponding iodide. The iodide is condensed with e.g. t-butyl acetate in the presence of a strong base such as lithium diisopropylamide to obtain the optically active 8-(tri-lower alkylsilyloxy)-4-allyloctanoic acid t-butyl ester. Condensation with 3-bromopyridine under conditions of the Heck reaction and deprotection yields the optically active 8-hydroxy-4-[3-(3-pyridyl)-prop-2-enyl]-octanoic acid t-butyl ester which can be converted to the 8-amino-4-[3-(3-pyridyl)-prop-2-enyl]-octanoic acid t-butyl ester (to prepare the corresponding compound of formula Ia wherein B represents 1,3-prop-2-enylene according to methodology known in the art and illustrated herein. Alternately the alcohol is first hydrogenated and then converted to 8-amino-4-[3-(3-pyridyl)-propyl]-octanoic acid t-butyl ester.

Alternately an illustrative starting ester of formula XII suitable for the preparation of a compound of formula IV can also be prepared as follows:

A lower alkyl ester of 2-oxocyclopentanecarboxylic acid is alkylated with allyl bromide to yield the lower alkyl ester of 1-(2-propenyl)-2-oxocyclopentanecarboxylic acid. Treatment with anhydrous ammonia yields the ester of 5-carboxy-oct-7-enoic acid amide. Treatment with thionyl chloride yields the ester of 5-carboxy-oct-7-enenitrile. The ester is reduced, e.g. with sodium borohydride to the corresponding alcohol. A reactive ester thereof, e.g. the methanesulfonyl ester is reacted with a diester of malonic acid and the resulting malonate ester is decarboxylated to yield the ester of 4-(3-cyanopropyl)-6-heptenoic acid which is then reacted with 3-bromopyridine under conditions of the Heck reaction to obtain the ester of 4-(3-cyanopropyl)-7-(3-pyridyl)-6-heptenoic acid which is hydrogenated under conditions known in the art, e.g. in ethanolic ammonia with rhodium on carbon catalyst, to the ester of 8-amino-4-[3-(3-pyridyl)-propyl]-octanoic acid.

Alternatively, a lower alkyl ester of 2-oxocyclopentanecarboxylic acid can be condensed with e.g. propargyl bromide to yield the lower alkyl ester of 1-(2-propynyl)-2-oxocyclopentanecarboxylic acid which is then reacted as described above to yield the corresponding ester of 4-(3-cyanopropyl)-6-heptynoic acid which is then reacted with 3-bromopyridine under conditions of the modified Heck reaction as described by D.E. Ames et al., Synthesis 1981, 364 to yield the ester of 4-(3-cyanopropyl)-7-(3-pyridyl)-6-heptynoic acid which is hydrogenated under conditions known in the art, e.g. in the presence of palladium on charcoal, to the lower alkyl ester of 8-amino-4-[3-(3- pyridyl)-propyl]-octanoic acid.

A starting material of formula XII wherein B represents oxygen or oxy-lower alkylene and Het represents 3-pyridyl can be prepared by condensation of an alcohol intermediate with 3-hydroxypyridine in the presence of triphenylphosphine and diethyl azodicarboxylate. For example, ethyl 7-cyano-5-hydroxy-heptanoate is condensed with 3-hydroxpyridine in the presence of triphenylphosphine and diethyl azodicarboxylate to obtain 7-cyano-5-(3-pyridyloxy)-heptanoate which is reduced to the corresponding amine of formula XII wherein A and M represent $(CH_2)_3$, B represents oxygen and Het represents 3-pyridyl.

An illustrative starting ester of a compound of formula XII suitable for the preparation of a compound of formula V can be prepared as follows:

5,6-Dihydro-2H-pyran-2-one is treated with vinyllithium in the presence of a cuprous salt to obtain 4-ethenyl-tetrahydro-2H-pyran-2-one which is reacted with 3-bromopyridine under conditions of a Heck condensation (J. Org. Chem. 43, 2952 (1978), e.g. in the presence of $Pd(OAc)_2$ and tri-o-tolylphosphine) to obtain 4-[2-(3-pyridyl)-ethenyl]-tetrahydro-2H-pyran-2-one. The lactone is reduced to the corresponding lactol, e.g. with diisobutyl aluminum hydride, which is condensed under Wittig conditions with e.g. methyl (triphenylphosphoranylidene)-acetate to obtain methyl 7-hydroxy-5-[2-(3-pyridyl)-ethenyl]-hept- 2-enoate. The two double bonds are then saturated using e.g. hydrogen in the presence of palladium on charcoal catalyst to obtain methyl 7-hydroxy-5-[2-(3-pyridyl)-ethyl]-heptanoate. The alcohol is converted to a reactive intermediate, e.g. the mesylate derivative, treated with e.g. sodium cyanide to obtain the nitrile which is then reduced to the methyl ester of the amine of formula XII wherein Het represents 3-pyridyl, A and M represent 1,3-propylene and B represents 1,2-ethylene.

An illustrative starting ester of a compound of formula XII suitable for the preparation of a compound of formula VI can be prepared as follows:

Wittig condensation of 3-pyridinecarboxaldehyde with e.g. 5-carboxypentyl-triphenylphosphonium bromide yields 7-(3-pyridyl)-hept-6-enoic acid which is converted to e.g. the methyl ester. Treatment with N-bromosuccinimide followed by sodium hydride yields the epoxide 2-(3-pyridyl)-3-(4-methoxycarbonylbutyl)-oxirane. Rearrangement with a Lewis or protonic acid, e.g. zinc iodide or p-toluenesulfonic acid yields the ketone, methyl 7-(3-pyridyl)-6-oxoheptanoate. Wittig type condensation, e.g. with diethyl cyanomethylphosphonate, and hydrogenation yields the methyl ester of the amine of formula XII wherein Het represents 3-pyridyl, A represents 1,2-ethylene, B represents methylene and M represents 1,4-butylene.

An illustrative starting ester of a compound of formula XII suitable for the preparation of a compound of formula VII can be prepared as follows:

Methyl 3-oxo-hept-6-enoate is prepared e.g. by condensation of methyl acetoacetate with allyl bromide in the presence of sodium hydride. Condensation with 3-bromopyridine under conditions of a Heck condensation yields methyl 7-(3-pyridyl)-3-oxo-hept-6-enoate. Condensation thereof with e.g. 4-iodobutyronitrile in the presence of sodium hydride leads to methyl 2-(3-cyanopropyl)-7-(3-pyridyl)-3-oxo-hept-6-enoate. Decarboxylation thereof e.g. with sodium chloride in dimethylsulfoxide/water yields 10-(3-pyridyl)-6-oxo-dec-9-enenitrile. This is subjected to Wittig type condensation with triethyl phosphonoacetate followed by hydrogenation e.g. with Raney nickel catalyst in e.g. methanol/ammonia to yield ethyl 7-(3-pyridyl)-3-(5-aminopentyl)-hept-2-enoate. Further hydrogenation with Pd/C catalyst yields the amine of formula XII wherein Het represents 3-pyridyl, A represents 1,5-pentylene, B represents 1,4-butylene and M represents methylene, as the ethyl ester.

An illustrative starting ester of a compound of formula XII suitable for the preparation of a compound of formula VIII can be prepared as follows:

Diethyl malonate is alkylated with e.g. 5-bromopent-1-ene to yield diethyl pent-4-enylmalonate. Such is reacted with 3-bromopyridine under conditions of the Heck condensation to yield diethyl [5-(3-pyridyl)-pent-4-enyl]malonate. The olefin is hydrogenated in the presence of e.g. palladium catalyst and the resulting substituted malonate is again alkylated with e.g. 6-bromocapronitrile to yield diethyl [5-(3-pyridyl)-pentyl]-(5-cyanopentyl)-malonate. The nitrile is reduced to the amine, with e.g. hydrogen in the presence of Raney nickel and ammonia, to yield diethyl [5-(3-pyridyl)-pentyl]-(6-aminohexyl)-malonate which is hydrolyzed and decarboxylated e.g. with hydrochloric acid, to yield the amine of formula XII wherein Het represents 3-pyridyl, A represents 1,6-hexylene, B represents 1,5-pentylene and M represents a direct bond, which can be converted to e.g. the ethyl ester with ethanolic hydrochloric acid.

An illustrative starting ester of a compound of formula XII suitable for the preparation of a compound of formula IX can be prepared as follows:

3-Pyridylacetonitrile is alkylated with e.g. methyl 6-bromohexanoate. The resulting nitrile is reduced e.g. by hydrogenation to the methyl ester of the amine of formula XII wherein Het represents 3-pyridyl, A represents methylene, B represents a direct bond and M represents 1,5-pentylene.

An illustrative starting ester of a compound of formula XII suitable for the preparation of a compound of formula III can be prepared as already described above from the appropriate aldehyde by condensation with e.g. methyl triphenylphosphoranylidene-acetate or with triethyl phosphonoacetate. For example, the omega-amino acid obtained by reduction, hydrolysis and decarboxylation of diethyl (4-azidobutyl)-[3-(3-pyridyl)-propyl]-malonate, protected e.g. as the N-t-butoxycarbonyl derivative, is converted to the ethyl ester and reduced with e.g. diisobutylaluminum hydride to the aldehyde. The aldehyde is then condensed with e.g. ethyl triphenylphosphoranylidene-acetate and selectively N-deprotected with acid to yield an intermediate of formula XII wherein Het represents 3-pyridyl, A represents 1,4-butylene, B represents 1,3-propylene and M represents 1,2-ethenylene, as the ethyl ester.

An illustrative starting ester of a compound of formula XII suitable for the preparation of a compound of formula IIIa can be prepared as follows:

Protected Hex-5-enol, e.g. as a tetrahydropyranyl ether, is converted to the epoxide by treatment with m-chloroperbenzoic acid. The epoxide is opened with lithium acetylide to obtain 1-tetrahydropyranyloxy-5-hydroxy-oct-7-yne. Treatment with 3-bromopyridine under conditions of a modified Heck reaction yields 1-tetrahydropyranyl-oxy-5-hydroxy-8-(3-pyridyl)-oct-7-yne which is hydrogenated, e.g. in the presence of palladium on charcoal, to 1-tetrahydropyranyloxy-5-hydroxy-8-(3-pyridyl)-octane, which is in turn converted to the 5-0-tosyl derivative, which is condensed with e.g. ethyl thioacetate in the presence of base to obtain 1-tetrahydropyranyloxy-5-(ethoxycarbonylmethylthio)-8-(3-pyridyl)-octane. The tetrahydropyranyl protecting group is removed under standard conditions and the alcohol is converted under standard conditions, e.g. via a mesylate, to the amine of formula XII wherein Het represents 3-pyridyl, A represents 1,4-butylene, B represents 1,3-propylene, and M represents thiomethylene. Similarly prepared are the intermediates wherein M represents e.g. oxymethylene, using ethyl hydroxyacetate instead of ethyl thioacetate.

A starting material, as an ester of the acid of formula XII wherein A and M represent lower alkylene and B represents phenylene, suitable for the preparation of e.g. an illustrative compound of the formula IIIc wherein m represents 4, n represents 2, $R_a$ and $R_b$ represent hydrogen and Het represents m-(3-pyridyl), can be prepared as follows:

3-(Trifluoromethylsulfonyloxy)-pyridine is condensed with ethyl m-(trifluoromethanesulfonyloxy)-phenylacetate in the presence of hexamethylditin, lithium chloride and tetrakis-(triphenylphosphine)-palladium to obtain ethyl m-(3-pyridyl)-phenylacetate. The product is alkylated with 1-bromo-4-chlorobutane to obtain the alpha-(4-chlorobutyl)-substituted phenylacetic acid ester. The ester is then reduced to the aldehyde which is condensed with e.g. methyl(triphenylphosphoranylidene)-acetate. The resulting alpha,beta-unsaturated ester is saturated to methyl 8-chloro-4-[m-(3-pyridyl)-phenyl]-octanoate which is converted to methyl 8-amino-4-[m-(3-pyridyl)-phenyl]octanoate according to methodology described herein.

An illustrative starting ester of a compound of formula XII suitable for the preparation of a compound of formula IIIb wherein m represents 3, n represents 2, p' represents zero, Ra and Rb represent hydrogen and Het represents 3-pyridyl may be prepared as follows:

Hex-5-enoic acid is first converted to the corresponding epoxide with e.g. m-chloroperbenzoic acid and esterified with diazomethane to the methyl ester which is then condensed with acetonitrile in the presence of lithium diisopropylamide (LDA) to yield methyl 7- cyano-5-hydroxyheptanoate. Alternatively, 5-oxohexanoic acid is condensed with bromoacetonitrile in the presence of e.g. the potassium salt of hexamethyl disilazane, followed by esterification with e.g. diazomethane and reduction with sodium borohydride to yield methyl 7-cyano-5-hydroxyheptanoate. Condensation with 3-hydroxypyridine in the presence of triphenylphosphine and reduction of the nitrile yields methyl 8-amino-5-(3-pyridyloxy)-octanoate.

The preparation according to process (b) is carried out according to methods known in the art for extending the carbon chain, for example by condensing the aldehyde of formula XIII in a Wittig type reaction with a terminal triphenylphosphoranylidene or di-lower alkylphosphono derivative of a lower alkanoic acid ester, e.g. with a trilower alkyl phosphono-lower alkylcarboxylate or a lower alkyl (triphenylphosphoranylidene)-lower alkylcarboxylate to give a corresponding compound of formula I or derivative thereof wherein M represents lower alkenylene.

In a more particular embodiment of the invention, a carboxaldehyde of the formula XVII

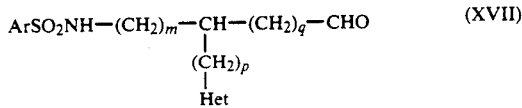
(XVII)

wherein Ar, m, p, q have meaning as defined in e.g. formula III is condensed in a Wittig type condensation with a trilower alkyl ester of phosphonoacetic acid or a lower alkyl ester of (triphenylphosphoranylidene)-acetic acid to yield a corresponding compound of formula III wherein $COR_1$ represents carboxy derivatized in the form of an ester, and converting a compound so obtained into another compound of the invention, e.g. by hydrogenation, to obtain e.g. the corresponding compound of the invention wherein in formula I, M represents lower alkylene, in particular of formula II.

The starting carboxaldehydes can be prepared e.g. by reduction of the respective carboxylic acid derivative, e.g. an ester, lactone or acid chloride under conditions known in the art and as illustrated herein.

For example, for the preparation of a compound of formula III wherein m represents 4, q represents zero and p represents 3, the corresponding starting aldehyde of formula XV is prepared as follows:

Diethyl (4-aminobutyl)-[3-(3-pyridyl)-propyl]-malonate, the preparation of which is described above under process (a) for the preparation of a compound of formula IV, is treated with a reactive functional derivative of a sulfonic acid of formula XI, e.g. the arylsulfonyl halide in the presence of a base e.g. as described under process (a). The resulting malonate ester is then hydrolyzed and decarboxylated e.g. with hydrochloric acid to obtain 6-(arylsulfonamido)-2-[3-(3-pyridyl)-propyl]-hexanoic acid which is in turn treated e.g. with thionyl chloride in the presence of a lower alkanol to obtain the corresponding lower alkyl ester. Treatment thereof with a reducing agent, e.g. diisobutylaluminum hydride at low temperature yields the corresponding 6-(arylsulfonamido)-2-[3-(3-pyridyl)-propyl]-hexaldehyde.

The chain lengthening process (b) is particularly suitable for the preparation of compounds of formula IV and IVa.

The decarboxylation according to process (c) is carried out according to methods well-known in the art for the decarboxylation of malonates, e.g. by treatment with a strong acid, e.g. hydrochloric acid, advantageously in acetic acid at elevated temperature, or as further illustrated herein.

The starting materials, being disubstituted malonate derivatives, are generally prepared by consecutive double alkylation of a diester of malonic acid followed by further appropriate transformations according to methods known in the art and illustrated herein.

An illustrative starting material of formula XIV, e.g. suitable for the preparation of a compound of formula VIII can be prepared as follows:

An amine, e.g. diethyl [5-(3-pyridyl)-pentyl]-(6-aminohexyl)-malonate, the preparation of which is outlined under process (a), is treated with the appropriate derivative of a sulfonic acid of formula XI, e.g. the arylsulfonyl halide, under standard conditions, in the presence of a base to obtain the corresponding arylsulfonamide-substituted malonate ester.

The condensation according to process (d) with optionally substituted imidazole can be carried out according to N-alkylation procedures well-known in the art, either as such, or in the presence of a base, e.g. triethylamine or pyridine, in an inert solvent such as acetonitrile or dimethylformamide at a temperature ranging from room temperature to near the boiling point of the solvent used.

A reactive esterified hydroxy group as mentioned herein represents a leaving group, particularly hydroxy esterified by a strong acid, especially hydrochloric, hydrobromic or hydriodic acid, or sulphuric acid, or by a strong organic acid, especially a strong organic sulfonic acid, such as an aliphatic or aromatic sulfonic acid, for example methanesulfonic acid, 4-methylphenylsulfonic acid or 4-bromophenylsulfonic acid. Said reactive esterified hydroxy group is especially halo, for example chloro, bromo or iodo, or aliphatically or aromatically substituted sulfonyloxy, for example methanesulfonyloxy, phenylsulfonyloxy or 4-methylphenylsulfonyloxy (tosyloxy).

The starting materials of formula XV wherein $COR_1$ represents esterified carboxy are prepared from the corresponding alcohol (Z represents hydroxy) by conversion to a reactive esterified derivative, e.g. wherein Z represents halo (e.g. bromo or iodo), arylsulfonyloxy or alkylsulfonyloxy under conditions known in the art. The hydroxy ester precursors can in turn be prepared e.g. by ring opening of suitably substituted lactones.

A representative starting material of formula XVa

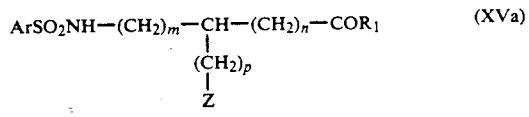
(XVa)

wherein $COR_1$ represents esterified carcoxy, Z represents methanesulfonyloxy, m represents 4, n represents 2, p represents 2, which is suitable for preparing a corresponding compound of formula IVa wherein Het represents 1-imidazolyl can be prepared as follows:

4-(p-Methoxyphenyl)-butanol is converted by reduction with sodium and liquid ammonia followed by acid hydrolysis to 4-(4-hydroxybutyl)-cyclohex-3-enone. The double bond is reduced by hydrogenation and the ketone is oxidized under Baeyer-Villiger oxidation conditions for lactone formation, e.g. with m-chloroperbenzoic acid to the epsilon caprolactone derivative 4-(4-hydroxybutyl)-6- hexanolactone. The alcohol is then converted according to standard procedures, e.g. via the mesylate derivative, to the azide which is reduced, e.g. by hydrogenation, to the corresponding amine which can then be condensed with an arylsulfonyl halide (as described in process a) to obtain the corresponding 4-[4-(arylsulfonamido)-butyl]-6-hexano-lactone. The lactone ring is opened with aqueous base to the hydroxy acid which is in turn esterified with an alcohol, e.g. in the presence of thionyl chloride, and the resulting hydroxy ester is then converted to the above-cited methanesulfonyloxy derivative of formula XVa. Alternatively, the lactone is directly opened with trimethylsilyl iodide in ethanol to the iodo ester of formula XVa wherein $R_1$ represents ethoxy and Z represents iodo.

A further representative starting material of formula XVa wherein $COR_1$ represents esterified carboxy, Z represents iodo, m represents 4, n represents 2, p represents 3 which is suitable for preparing a compound of formula IV wherein Het represents 1-imidazolyl (a compound of formula IVc) can for example be prepared as follows:

2-Ethoxycarbonylcyclopentanone is alkylated in the presence of a base (e.g. potassium carbonate) with 3-tetrahydropyranyloxy-1-bromopropane to yield 2-ethoxycarbonyl-2-[3-(tetrahydropyranyloxy)propyl]-cyclopentanone. Opening of the cyclopentanone ring with ammonia gas yields 5-ethoxycarbonyl-5-[3-tetrahydropyranyloxy)-propyl]valeramide. The ester and amide functions are then reduced with e.g. lithium aluminum hydride to yield 6-amino-2-[3-(tetrahydropyranyloxy)propyl]-hexanol which is treated with an arylsulfonyl halide to obtain the corresponding 6-arylsulfonamido-2-[3-(tetrahydropyranyloxy)propyl]-hexanol. The hydroxy function is converted to a reactive derivative, e.g. the iodo derivative, and such is condensed with e.g. t-butyl acetate in the presence of a strong base such as LDA so as to obtain the t-butyl ester of 8-aryl- sulfonamido-4-(3-tetrahydropyranyloxy)-propyl]-octanoic acid. Removal of tetrahydropyranyl protecting group and conversion of the alcohol to iodo (via methanesulfonyl ester) yields the corresponding ester intermediate of formula XVa wherein Z represents iodo, m represents 4, n represents 2 and p represents 3.

The imidazoles used as starting materials for condensation with a compound of formula XV are known in the art or are prepared according to methods known in the art.

In the intermediates e.g. of formula XVa, the —SO$_2$NH— grouping may be protected in form of an N-acyl derivative, e.g. the t-butoxycarbonyl derivative, prior to condensation with the imidazole.

The condensation according to process (e) is carried out e.g. by reacting a compound of formula XV, wherein Z represents hydroxy and the carboxy group is esterified, with 3-hydroxypyridine optionally substituted by lower alkyl, in the presence of triphenylphosphine and diethyl azodicarboxylate in an inert solvent such as methylene chloride.

Alternatively the condensation according to process (e) can be carried out e.g. by reacting a compound of formula XV or XVa wherein Z represents reactive esterified hydroxy, the carboxy group is esterified and —SO$_2$NH— may be protected, with e.g. an alkali metal salt of optionally substituted 3-hydroxypyridine or 3-mercaptopyridine in an inert polar solvent.

The starting materials including compounds of formula XV and XVa, and protected forms thereof, are prepared according to methods described herein, e.g. under process (d), or as known in the art.

The condensation according to process (f) is carried out according to methods known in the art for a Wittig condensation, e.g. by condensing an aldehyde as defined in terms of formula XV with e.g. (3-pyridylmethylene)-triphenylphosphorane prepared by treating 3-pyridylmethyltriphenylphosphonium halide with a strong anhydrous base such as n-butyl lithium or potassium t-butoxide.

The starting aldehyde can be prepared by Swern oxidation of the corresponding alcohol of formula XV (e.g. with dimethylsulfoxide/oxalyl chloride).

The process according to process (g) can be carried out under conditions known in the art for a Heck condensation of an alkene with an aryl halide, and as described herein.

An illustrative starting material can be prepared as follows:

The ethyl ester of cyclopentanone-2-carboxylic acid is alkylated with allyl bromide to obtain 2-allyl-2-ethoxycarbonyl-cyclopentanone which is in turn treated with ammonia to obtain 5-ethoxycarbonyl-oct-7-enoic acid amide. Reduction with lithium aluminum hydride yields 5-hydroxymethyl-oct-7-enylamine. Condensation with the appropriate arylsulfonyl halide yields N-arylsulfonyl-5-hydroxymethyloct-7-enylamine which is oxidized to the corresponding aldehyde. The aldehyde is then condensed in a Wittig type reaction e.g. with methyl (triphenylphosphoranylidene)-acetate to obtain a compound of the formula

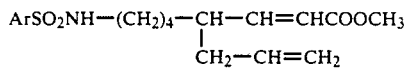

which is then condensed with 3-bromopyridine under the conditions of the Heck reaction to obtain a compound of the formula

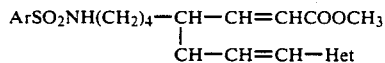

wherein Ar has meaning as previously defined and Het represents 3-pyridyl optionally substituted by lower alkyl. Hydrogenation of double bonds yields corresponding compound of formula III wherein m represents 4, q represents zero and p represents 3, and/or corresponding compound of formula IV.

Process (h) invovles the conversion of group Y to carboxy or carboxy derivatized in the form of a pharmaceutically acceptable estser or amide and is carried out according to methods well known in the art. Examples of convertible group Y are hydroxymethyl, formyl, cyano or halomethyl.

Process (i) is carried out according to methodology well-known in the art for the preparation of tetrazoles, e.g. as described in Barton et al, Comprehensive Organic Chemistry Vol. 4, pp. 407–409 (1979) preferably in an inert solvent such as dimethylformamide or tetrahydrofuran, and at an elevated temperature ranging from about 50° to 200°, optionally in the presence of acid.

Sources of hydrazoic acid are e.g. a metal or ammonium salt thereof or an organometallic derivative, e.g. tributyltin azide.

The nitrile starting material is preferably prepared from the corresponding primary amide of a compound of formula I by treatment with a dehydrating agent such as trifluoroacetic anhydride in the presence of pyridine, or thionyl chloride in dimethylformamide.

The amides of compounds of formula I can be prepared e.g. by conversion of the corresponding carboxylic acid to the acid halide and subsequent treatment with the appropriate amine, e.g. with ammonia to yield the primary amide. Alternately amides can be prepared by aminolysis of the corresponding lower alkyl esters.

A reactive esterified hydroxy group in any of the above mentioned processes is hydroxy esterified by a strong acid, especially a strong inorganic acid, such as a hydrohalic acid, especially hydrochloric, hydrobromic or hydriodic acid, or sulphuric acid, or by a strong organic acid, especially a strong organic sulfonic acid, such as an aliphatic or aromatic sulfonic acid, for example methanesulfonic acid, 4-methylphenylsulfonic acid or 4-bromophenylsulfonic acid. Said reactive esterified hydroxy group is especially halo, for example chloro, bromo or iodo, or aliphatically or aromatically substituted sulfonyloxy, for example phenylsulfonyloxy or 4-methylphenylsulfonyloxy (tosyloxy).

In starting compounds and intermediates which are converted to the compounds of the invention in a manner described herein, functional groups present, such as carbonyl (formyl or keto), carboxy, amino, hydroxy and sulfhydryl groups, are optionally protected by conventional protecting groups that are common in preparative organic chemistry. Protected carbonyl, carboxy, amino, hydroxy and sulfhydryl groups are those that can be converted under mild conditions into free carbonyl, carboxy, amino, hydroxy and sulfhydryl groups without the molecular framework being destroyed or other undesired side reactions taking place.

Well-known protecting groups that meet these conditions and their introduction and removal are described, for example, in J. F. McOmie, "Protective Groups in Organic Chemistry", Plenum Press, London, New York 1973, T. W. Greene, "Protective Groups in Organic Synthesis", Wiley, New York 1984, and also in "The Peptides", Vol. I, Schroeder and Luebke, Academic Press, London, New York 1965.

The compounds of the invention obtained can be converted into each other according to conventional methods. Thus, for example, resulting esters may be hydrolyzed with aqueous alkalies, such as alkali metal carbonates or hydroxides. Resulting free acids may be esterified with e.g. said unsubstituted or substituted alkanols or reactive esterified derivatives thereof such as alkyl halides, or diazoalkanes. The compounds of the invention, when free acids, are also converted into metal or ammonium salts in conventional manner. The basic compounds of the invention are also converted to acid addition salts in conventional manner.

Any resulting free acid or base can be converted into a corresponding metal, ammonium or acid addition salt respectively, by reacting it with an equivalent amount of the corresponding base, basic salt, acid or ion exchange preparation.

In view of the close relationship between the free compounds and the salts thereof, whenever a compound of the invention, or intermediate, is referred to in this context, a corresponding salt is also intended, provided such is possible or appropriate under the circumstances.

The compounds, including their salts, may also be obtained in the form of their hydrates, or include other solvents used for the crystallization.

The compounds of the invention which contain one or more double bonds may be converted to the corresponding saturated compounds of the invention. Such conversion is carried out e.g. by catalytic hydrogenation in the presence of a catalyst such as rhodium, nickel or platinum in a polar medium using procedures well-known in the art and as illustrated in the examples.

Depending on the choice of starting materials and methods, the new compounds may be in the form of one of the possible isomers or mixtures thereof, for example, as substantially pure geometric (Z or E, cis or trans) isomers, optical isomers (antipodes), racemates, or mixtures thereof. The aforesaid possible isomers or mixtures thereof are within the purview of this invention.

In case mixtures of geometrical or optical isomers of the above compounds are obtained, these can be separated into the single isomers by methods in themselves known, e.g., by fractional distillation, crystallization and/or chromatography. Racemic products can likewise be resolved into the optical antipodes, for example, by separation of diastereomeric salts thereof, e.g., for basic compounds by the fractional crystallization of d- or l-(tartrate, mandelate or camphorsulfonate) salts, or for acidic compounds by fractional crystallization of d- or l-(alphamethylbenzylamine, cinchonidine, cinchonine, quinine, quinidine, ephedrine, dehydroabietylamine, brucine or strychnine)-salts.

The above-mentioned reactions are carried out according to standard methods, in the presence or absence of diluents, preferably such as are inert to the reagents and are solvents thereof, of catalysts, alkaline or acidic condensing or said other agents respectively and/or inert atmospheres, at low temperatures, room temperature or elevated temperatures, preferably near the boiling point of the solvents used, at atmospheric or superatmospheric pressure.

The invention further includes any varient of said processes, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes.

The present invention also relates to the use of the compounds of the invention for the preparation of pharmaceutical compositions especially pharmaceutical compositions having thromboxane suppressing, i.e. thromboxane synthetase inhibitory and thromboxane receptor blocking activity useful for the treatment or prevention of thromboxane dependent conditions or syndromes in mammals.

The pharmaceutical compositions according to the invention are those suitable for enteral, such as oral or rectal, transdermal and parenteral administration (including infusion) to mammals, including man, for the treatment or prevention of conditions or syndromes responsive to suppression of thromboxane activity, such as occlusive vascular conditions, comprising an effective thromboxane activity suppressing amount of a compound of the invention in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salts and/or polyethyleneglycol; for tablets also c) binders, e.g. magnesium aluminum silicate, starch paste, gelatin, tragacanth, methylcellulose, sodium carboxymethylcellulose and/or polyvinylpyrrolidone; if desired, d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

The dosage of active compound administered is dependent on the species of warm-blooded animal (mammal), the body weight, age and individual condition, and on the form of administration.

The active ingredient is administered at an effective thromboxane activity suppressing dose, e.g. between about 0.01 to 25 mg/Kg/day, preferably between about 0.5 to 10 mg/Kg/day orally, between about 0.1 to 5 mg/Kg/hour by infusion, and between about 0.01 to 1 mg/Kg intravenously.

A unit dosage for oral administration to a mammal of about 50 to 70 Kg may advantageously contain between about 25 and 250 mg of the active ingredient.

The pharmaceutical formulations contain an effective thromboxane activity suppressing amount of a compound of the invention as defined above either alone or in combination with another therapeutic agent selected from e.g. a thrombolytic agent, an angiotensin converting enzyme inhibitor, a calcium channel blocker, an anticoagulant, a serotonin-2-antagonist, or an immunosuppressive agent at an effective therapeutic dose. Such therapeutic agents are well-known in the art as well as their effective doses.

Illustrative thrombolytic agents are e.g. TPA, urokinase, streptokinase, APSAC; illustrative angiotensin converting enzyme inhibitors are e.g. captopril, enalapril, enalaprilat, quinapril, ramipril, cilazapril, delapril, fosenopril, zofenopril, indolapril, lisinopril, moveltipril, perindopril, spirapril, pentopril, pivopril, benazepril, benazeprilat and libenzapril; illustrative calcium channel blockers are e.g. diltiazem, nifedipine, nisoldipine, verapamil and isradipine; illustrative serotonin-2 antagonists are e.g. ketanserin, cinanserin, irindalone; illustrative anticoagulants are heparin, hirudin and derivatives thereof such as desulfatohirudin; and illustrative immunosuppressive agents are e.g. cyclosporine and related compounds.

The invention also further relates to the treatment of mammals, including man, using a compound of the invention, preferably in the form of a pharmaceutical composition, either alone or in combination with other therapeutic agents as illustrated herein.

More particularly the invention relates to:

(a) a method of suppressing thromboxane activity in mammals which comprises administering to a mammal in need thereof an effective thromboxane suppressing amount of a compound of the invention;

(b) a method of inhibiting thromboxane synthesis in mammals which comprises administering to a mammal in need thereof an effective thromboxane synthetase inhibiting amount of a compound of the invention;

(c) a method of blocking thromboxane receptor activity in mammals which comprises administering to a mammal in need thereof an effective thromboxane receptor blocking amount of a compound of the invention;

(d) a method of inhibiting platelet aggregation in mammals which comprises administering to a mammal in need thereof an effective platelet aggregation inhibiting amount of a compound of the invention.

(e) a method of treating or preventing thromboxane dependent conditions or syndromes in mammals which comprises administering to a mammal in need thereof an effective thromboxane activity suppressing amount of a compound of the invention.

Thromboxane dependent conditions or syndromes involved are e.g. myocardial infarctions (heart attacks); cerebral infarctions (strokes); angina (stable or unstable); hypertension such as pregnancy induced hypertension (e.g. toxemia, preeclampsia); renal disorders (e.g. lupus nephritis, diabetic nephropathy and cyclosporine-induced nephrotoxicity); peripheral vascular disorders (e.g. peripheral venous or arterial occlusive conditions); vascular e.g. coronary reocclusion after thrombolytic therapy, bypass surgery or angioplasty; allograft rejection as in heart transplantation; pulmonary disorders such as bronchoconstriction as in bronchial asthma; or platelet loss during extracorporeal circulation.

A particular aspect involves a method of treating or preventing occlusive vascular conditions comprising peripheral vascular disorders, thrombosis, atherosclerosis, cerebral and myocardial infarction, and coronary reocclusion occurring after angioplasty, after coronary bypass surgery or after thrombolytic therapy, which comprises administering to a mammal in need thereof an effective amount of a compound of the invention.

A further aspect of the invention relates to the treatment of disorders and syndromes described herein which comprises administering the compounds of the invention in conjunction with other therapeutic agents to mammals in order to enhance the therapeutic effectiveness of such other therapeutic agents.

For instance, the compounds of the invention can be administered to mammals to enhance the effect of thrombolytic agents (e.g. TPA, urokinase, streptokinase, anistreplase and the like), e.g. by reducing their required dose and the required time to achieve reperfusion in myocardial infarction, and also to prevent or reduce the incidence of reocclusion after treatment with said thrombolytic agents.

Thus the present invention provides a method for the treatment of myocardial infarction and coronary occlusion in mammals comprising the administration, in combination with a said thrombolytic agent, of a compound of the invention which serves to reduce the dose of thrombolytic agent needed to lyse clots, to reduce the time required for lysis of clots, to prevent reocclusion following thrombolysis with the thrombolytic agent, and to keep blood vessels unobstructed for a longer period of time.

The compounds of the invention can also be administered to mammals at doses which are essentially devoid of antihypertensive activity to enhance the antihypertensive effect of angiotensin converting enzyme inhibitors, e.g. those cited hereinabove.

Similarly the compounds of the invention can also be administered to mammals to enhance the cardiovascular effects, e.g. antianginal effects, of calcium channel blockers (e.g. diltiazem, nifedipine, nisoldipine, verapamil, isradipine) in the treatment of myocardial infarctions.

Further illustrative of the invention, the compounds of the invention can also be administered to mammals to enhance the effect of anticoagulants, e.g. heparin, hirudin, desulfatohirudin, and derivatives thereof, to improve perfusion in occlusive vascular disorders.

Illustrative of the invention, the compounds of the invention can further be administered to mammals to enhance the antiplatelet effects of serotonin-2 receptor antagonists (e.g. ketanserin, cinanserin, irindalone) in the treatment of occlusive vascular disorders.

A further aspect of the invention comprises a method of alleviating cyclosporin-induced naphrotoxicity by administering to a mammal undergoing cyclosporine therapy an effective thromboxane suppressing amount of a compound of the invention.

In the above-cited methods of treatment in conjunction with another active ingredient, a compound of the invention may be administered either simultaneously, before or after the other active ingredient, either separately by the same or different route of administration or together in the same pharmaceutical formulation, in an amount effective at suppressing thromboxane activity.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by standard analytical methods, e.g. microanalysis and spectroscopic characteristics (e.g. MS, IR, NMR). Unless otherwise specified, chromatography is carried out using silica gel. Flash chromatography refers to medium pressure column chromatography according to Still et al, J. Org. Chem. 43, 2928 (1978).

EXAMPLE 1

A solution of 23.0 g (43.8 mmol) of diethyl [4-(p-chlorophenylsulfonamido)butyl][3-(3-pyridyl)propyl]-malonate, 400 mL acetic acid and 400 mL 6N hydrochloric acid is refluxed for 36 hours. The solvent is evaporated and the residue taken up in water and adjusted to pH 5. The aqueous layer is extracted with chloroform (4×100 mL). Combined organic layer is evaporated to dryness. The oil is taken up in hot ethanol and treated with charcoal. The solution is concentrated to about 100 mL, and heated to reflux; water is added slowly until first signs of cloudiness appear. Then the solution is allowed to cool slowly to crystallize 6-(p-chlorophenylsulfonamido)-2-[3-(3-pyridyl)propyl]-hexanoic acid, m.p. 139–141°.

The starting material is prepared as follows:

A solution of 32.53 g (0.24 mole) of 3-(3-pyridyl)-propan-1-ol in 176 mL of 48% hydrobromic acid is refluxed for 24 hours. The reaction mixture is evaporated and the residue is taken up in 500 mL isopropanol and subjected to evaporation again. The evaporation procedure is repeated one more time. The resulting product is then taken up in hot isopropanol and treated with charcoal and filtered. The filtrate is cooled slowly to give 3-(3-pyridyl)propyl bromide hydrobromide, m.p. 103–105°.

To a solution of 48 mL (0.37 mole) of diethyl malonate in 960 mL ethanol is added 14.03 g (0.61 mole) sodium metal and the mixture is stirred until all of the metal dissolved. The solution is heated to reflux and a solution of 80.04 g (0.28 mole) of 3-(3-pyridyl)-propyl bromide hydrobromide in 960 mL ethanol is added rapidly and the mixture is maintained at reflux for 10 hours. The reaction mixture is evaporated and the residue is taken up in 400 mL of 1N aqueous hydrochloric acid and washed with 400 mL hexane. The aqueous phase is adjusted to pH 8 using solid sodium bicarbonate. The mixture is then extracted with methylene chloride (3×200 mL). Combined organic extracts are dried (MgSO$_4$), filtered and evaporated to dryness to give diethyl [3-(3-pyridyl)-propyl]-malonate as an oil.

To a solution of 63.34g (0.23 mole) of diethyl [3-(3-pyridyl)-propyl]malonate in 1.1L dimethylformamide is in small portions 9.91 g (0.25 mole) of sodium hydride as a 60% dispension in oil. After stirring at room temperature for 0.5 hours, 28 mL (0.23 mole) of 1-bromo-4-chlorobutane is added and then heated to 60° for 10 hours. Then 68.26 g (0.46 mole) sodium iodide is added followed by 44.44 g (0.68 mole) sodium azide and 9.0 g crown ether 18-Crown-6. The reaction mixture is heated for 15 hours at 60°, is then cooled and poured on ice. The mixture is then extracted with ether (4×500 mL). Combined organic extracts are extracted with 1N aqueous hydrochloric acid (1×200, 2×100 mL). Combined aqueous extract is adjusted to pH 8 by addition of solid sodium bicarbonate and then extracted with ether (3×300 mL). Combined organic extracts are washed with water (3×100 mL), brine (1×300 mL), dried (MgSO$_4$), filtered and then evaporated to dryness to give diethyl [4-azidobutyl][3-(3-pyridyl)-propyl]-malonate as an oil.

To a solution of 42.59 g (0.11 mole) of diethyl [4-azidobutyl][3-(3-pyridyl)-propyl]-malonate in 270 mL THF and 3.1 mL water is added 29 g (0.11 mole) of triphenyl phosphine and the solution is stirred well for 48 hours. Solvent is evaporated and the residue subjected to flash chromatography to give diethyl [4-aminobutyl][3-(3-pyridyl)- propyl]malonate as an oil.

A solution of 15.0g (42.8 mmol) of diethyl [4-aminobutyl][3-(3-pyridyl)propyl] malonate in 115 mL methylene chloride is cooled to 0° and 0.1 g 4-dimethylaminopyridine is added followed by 8.4 mL (60 mmol) triethylamine and 10.12 g (46.5 mmol) p-chlorophenylsulfonyl chloride. The solution is stirred at room temperature for 48 hours and then washed with saturated aqueous sodium bicarbonate solution. The organic phase is dried (MgSO$_4$), filtered and evaporated to give diethyl [4-(p-chlorophenylsulfonamido)butyl][3-(3-pyridyl)propyl] malonate as an oil.

EXAMPLE 2

To a solution of 2.53 g (5.9 mmol) of 6-(p-chlorophenylsulfonamido)-2-[3-(3-pyridyl)propyl]-hexanoic acid in 150 mL ethanol is slowly added 1.5 mL (20.5 mmol) thionyl chloride and the reaction mixture is subjected to reflux for 8 hours. The solvent is evaporated and the residue is adjusted to pH 8 using 1N aqueous sodium hydroxide solution. The mixture is then extracted with methylene chloride (2×50 mL). Combined organic extracts are dried (MgSO$_4$) and evaporated to give an oil which is then purified by flash chromatography using ether as the eluent to obtain ethyl 6-(p-chlorophenylsulfonamido)-2-[3-(3pyridyl)propyl]-hexanoate as an oil.

EXAMPLE 3

To a solution of 3.08 g (7.5 mmol) of 6-(p-chlorophenylsulfonamido)-2-[3-(3-pyridyl)propyl]-hexanal in 40 mL chloroform is added 2.88 g (8.4 mmol) of methyl (triphenylphosphoranylidene)-acetate and then subjected to reflux for 3 hours. The solvent is evaporated and the residue taken up in ether and extracted with 0.5N HCl (3×20 mL). The aqueous extracts are combined and washed with ether. The aqueous phase is adjusted to pH 8 and then extracted with methylene chloride (3×50 mL). Combined organic extracts are dried (MgSO$_4$), filtered and then evaporated to give an amber oil. This is purified by flash chromatography using 7:3 EtOAc: hexane as the eluent to give methyl 8-(p-chlorophenylsulfonamido)-4-[3-(3-pyridyl)propyl]-oct-2-enoate as an oil.

The starting material is prepared as follows:

A solution of 3.5 g (7.7 mmol) of ethyl 6-(p-chlorophenylsulfonamido)-2-[3-(3-pyridyl)propyl]-hexanoate (example 2) in 105 mL methylene chloride is cooled to −78° and to it is added slowly 15.2 mL (23.6 mmol) of 1.53M solution of diisobutylaluminum hydride in toluene. The solution is stirred at −78° for 10 minutes and then quenched by slow addition of 10.8 mL methanol. The solution is then allowed to warm to 0° by the removal of the cold bath, and then 350 mL of ether is added followed by 10.8 mL of saturated brine and 7.7 g finely powdered anhydrous sodium sulfate. The cloudy suspension is stirred vigorously at room temperature overnight. The salts are filtered off and washed with methylene chloride (10×20 mL). The filtrate is evaporated to give 6-(p-chlorophenylsulfonamido)-2-[3-(3-pyridyl)propyl]hexanal.

EXAMPLE 4 a) To a solution of 3.27 g (7 mmol) of methyl 8-(p-chlorophenylsulfonamido)-4-[3-(3-pyridyl)propyl]-oct-2-enoate in 32 mL methanol, 0.446 g (1.87 mmol) cobalt (II) chloride hexahydrate is added. The solution is cooled in an ice bath and 0.573 g (15 mmol) sodium borohydride is added in small portions. Vigorous gas evolution and formation of a black precipitate is observed during the addition of sodium borohydride. After completion of the addition, the ice bath is removed and the mixture stirred at room temperature for 1 hour. The black precipitate is filtered off and washed with methanol. The combined filtrate is evaporated and the residue suspended in a mixture of 30 mL methylene chloride and 150 mL ether. The organic layer is washed with water. The aqueous phase is extracted with ether (2×50 mL). The combined organic extract is dried (MgSO$_4$), filtered and the solvent evaporated. The residue is subjected to flash chromatography on silica using 3:2 EtOAc, hexane as the eluent to give methyl 8-(p-chlorophenylsulfonamido)-4-[3-(3-pyridyl)propyl]-octanoate, m.p. 81–82°.

b) Similarly prepared is ethyl 8-(p-chlorophenylsulfonamido)-4-[3-(3-pyridyl)-propyl]-octanoate.

EXAMPLE 5 a) To a solution of 2.62 g (5.6 mmol) of methyl 8-(p-chlorophenylsulfonamido)-4-[3-(3-pyridyl)propyl]-octanoate. in 14 mL dioxane is added 11.6 mL of 1N NaOH (11.6 mmol) and the mixture is heated at 60° for 2 hours. The solvent is evaporated and the residue dissolved in water. The pH of the aqueous solution is adjusted to 5.0 using 2N aqueous HCl. The resulting mixture is extracted with methylene chloride (3×20 mL). The combined organic extract is dried (MgSO$_4$), filtered and subjected to evaporation to give an oil. Crystallization from ether yields 8-(p-chlorophenylsulfonamido)-4-[3-(3-pyridyl)propyl]-octanoic acid, m.p. 114–116°.

b) Similarly prepared is 8-(p-chlorophenylsulfonamido)-4-[3-(3-pyridyl)-propyl]-oct-2-enoic acid, m.p. ca. 75°, by hydrolysis of methyl 8-(p-chlorophenylsulfonamido)-4-[3-(3-pyridyl)-propyl]-oct-2-enoate of example 3.

EXAMPLE 6

Prepared substantially according to procedures described in the previous examples are:

(a) 8-(beta-naphthylsulfonamido)-4-[3-(3-pyridyl)-propyl]-octanoic acid, m.p. 103–104°;

(b) 8-(p-trifluoromethylphenylsulfonamido)-4-[3-(3-pyridyl)-propyl]-octanoic acid, m.p. 138–140°;

(c) 8-(phenylsulfonamido)-4-[3-(3-pyridyl)-propyl]-octanoic acid;

(d) 8-(3,4-dichlorophenylsulfonamido)-4-[3-(3-pyridyl)-propyl]-octanoic acid;

(e) 8-(p-methoxyphenylsulfonamido)-4-[3-(3-pyridyl)-propyl]-octanoic acid;

(f) 8-(p-methylphenylsulfonamido)-4-[3-(3-pyridyl)-propyl]-octanoic acid, m.p. 94–96°;

(g) 8-(p-carboxyphenylsulfonamido)-4-[3-(3-pyridyl)-propyl]-octanoic acid;

(h) 8-(p-chlorophenylsulfonamido)-4-[3-(4-methyl-3-pyridyl)-propyl]-octanoic acid, m.p. 61–71°;

(i) 8-(p-fluorophenylsulfonamido)-4-[3-(3-pyridyl)-propyl]-octanoic acid, m.p. 90–92°.

(j) 8-(p-methylsulfonylphenylsulfonamido)-4-[3-(3-pyridyl)-propyl]-octanoic acid, m.p. 109–112°.

(k) 8-(p-cyanophenylsulfonamido)-4-[3-(3-pyridyl)-propyl]-octanoic acid.

EXAMPLE 7

To a solution of 0.1 g (0.22 mmol) of 8-(p-chlorophenylsulfonamido)-4-[3-(3-pyridyl)-propyl]-octanoic acid in 10 mL methylene chloride is added 50 mg (0.23 mmol) of m-chloroperbenzoic acid and the resulting solution is stirred at room temperature for 18 hours. The solvent is evaporated and the residue is purified by flash chromatography to give a clear oil. Crystallization from ether gives 8-(p-chlorophenylsulfonamido)-4-[3-(3-pyridyl- N-oxide)-propyl]-octanoic acid, m.p. 55–57°.

EXAMPLE 8

To a solution of 0.127 g (9.045 mmol) of methyl 8-amino-5-[2-(3-pyridyl)ethyl]-octanoate in 5 mL methylene chloride are added a few crystals of 4-dimethylaminopyridine followed by 0.1 mL (0.7 mmol) triethylamine and 0.112 g p-chlorophenylsulfonyl chloride, and the solution is stirred at room temperature for 16 hours. The reaction is diluted with 10 mL methylene chloride and washed with saturated aqueous sodium bicarbonate solution. The organic phase is dried ($MgSO_4$), filtered and evaporated to obtain an oil which is purified by preparative thin layer chromatography to give methyl 8-(p-chlorophenylsulfonamido)-5-[2-(3-pyridyl)ethyl]-octanoate as an oil.

The starting material is prepared as follows:

A stream of nitrogen gas is passed through a mixture of 19.6 mL (41.2 mmol) of 2.1M vinyllithium in tetrahydrofuran and 21 mL toluene to evaporate tetrahydrofuran. The resulting pale yellow suspension is diluted with 21 mL ether and cooled to −78°. To this solution is added 1.87 g (20.9 mmol) cuprous cyanide and the reaction mixture is then warmed to 0° for 2 minutes. The resulting gray suspension is cooled to −78° and 0.9 mL (10.4 mmol) of 5,6-dihydro-2H-pyran-2-one is added. The reaction mixture is stirred at −78° for 30 minutes and at −20° for 15 minutes. The reaction is quenched by the addition of saturated aqueous ammonium chloride and stirred for 1 hour at room temperature. The insoluble salts are filtered off and washed with water (1×20 mL) and ether (2×20 mL). The layers are separated and the aqueous phase is extracted with ether (2×30 mL). Combined organic extracts are dried ($MgSO_4$), filtered and evaporated to give yellow oil which is purified by flash chromatography to obtain 4-ethenyltetrahydro-2H-pyran-2-one as a pale yellow oil.

To a solution of 0.879 g (7 mmol) of 4-ethenyltetrahydro-2H-pyran-2-one in 5 mL triethylamine and 5 mL acetonitrile is added 0.081 g (0.36 mmol) Palladium-(II)-acetate followed by 0.659 g (2.5 mmol) tri-o-tolylphosphine and 0.76 mL (7.9 mmol) 3-bromopyridine and the mixture is heated at 125° C. for 20 hours in a sealed tube. It is then cooled, diluted with methylene chloride and washed with water. The organic phase is dried ($MgSO_4$), filtered and evaporated to give a reddish oil which is flash chromatographed using ethyl acetate as eluent to obtain 4-[2-(3-pyridyl)ethenyl]tetrahydro-2H-pyran-2-one as an oil.

A solution of 1.01 g (5 mmol) of 4-[2-(3-pyridyl)-ethenyl]-tetrahydro-2H-pyran-2-one in 23 mL methylene chloride is cooled to −78° and 3.3 mL (5 mmol) of 1.53M solution of diisobutylaluminum hydride in toluene is added. The solution is warmed to 0° and stirred for 2 hours. The reaction is quenched with 2.5 mL methanol and the mixture filtered through a short plug of silica gel and eluted with methanol (10×10 mL). The filtrate is evaporated to give 4-[2-(3-pyridyl)]ethenyl]-2-hydroxytetrahydro-2H-pyran.

To a solution of 0.993 g (4.8 mmol) of 4-[2-(3-pyridyl)]-ethenyl-2-hydroxytetrahydro-2H-pyran in 12 mL methylene chloride is added 1.86 g (5.4 mmol) methyl (triphenylphosphoranylidene)-acetate and the mixture is then stirred at room temperature for 16 hours. The solvent is evaporated, the residue taken up in ether and the mixture is filtered to remove the precipitated triphenylphosphine oxide. The filtrate is extracted with 1N aqueous hydrochloric acid (1×10 mL, 2×5 mL). Combined aqueous extract is washed with ether, adjusted to pH 8 and extracted with methylene chloride (3×20 mL). Combined organic extracts are dried ($MgSO_4$), filtered and evaporated to give methyl 7-hydroxy-5-[2-(3-pyridyl)-ethenyl]-hept-2-enoate.

A solution of 1.75 g of methyl 7-hydroxy-5-[2-(3pyridyl)ethenyl]-hept-2-enoate in 50 mL ethanol is hydrogenated with 0.35 g 10% palladium on charcoal at 3 atmospheres pressure of hydrogen and room temperature for 21 hours. The catalyst is filtered off and washed with ethanol (4×10 mL). The filtrate is evaporated to give a yellow oil which is chromatographed to yield methyl 7-hydroxy-5-[2-(3-pyridyl)ethyl]-heptanoate.

A solution of 0.8 g (3.0 mmol) of methyl 7-hydroxy-5-[2-(3-pyridyl)ethyl]-heptanoate in 3 ml methylene chloride is cooled to 0° and 0.52 mL (3.7 mmol) triethylamine is added followed by 0.26 mL (3.3 mL) methanesulfonyl chloride. The reaction mixture is stirred at 0° for 30 minutes and then 1.65 g (25 mmol) finely powdered potassium cyanide is added followed by 15 mL dimethyl sulfoxide. After stirring for 30 minutes the cold bath is removed and the mixture is stirred at room temperature for 18 hours. The reaction mixture is poured on to saturated aqueous ammonium chloride solution and then extracted with ethyl acetate (3×70 mL). Combined organic phase is washed with water (4×60 mL), brine (60 mL) and dried ($MgSO_4$), filtered and evaporated to give an oil which is purified by flash chromatography to give both the desired methyl 7-cyano-5-[2-(3-pyridyl)ethyl]-heptanoate and the mesylate of the starting alcohol. The mesylate is subjected to the cyanide displacement conditions described above to yield additional methyl 7-cyano-5-[2-(3-pyridyl)-ethyl]-heptanoate.

To a solution of 0.1 g (0.37 mmol) of methyl 7-cyano-5-[2-(3-(pyridyl)ethyl]-heptanoate in 20 mL of methanol saturated with ammonia is added 0.15 mL Raney Nickel and the mixture is hydrogenated at 3 atmospheres pressure of hydrogen and room temperature for 4 hours. The catalyst is filtered off and washed with methanol (4×20 mL). The filtrate is evaporated to give methyl 8-amino-5-[2-(3-pyridyl)ethyl]-octanoate.

EXAMPLE 9

A mixture of 0.083 g (0.18 mmol) of methyl 8-(p-chlorophenylsulfonamido)-5-[2-(3-pyridyl)ethyl]-octanoate, 2 mL dioxane and 0.4 mL (0.4 mmol) 1N aqueous sodium hydroxide is stirred for 16 hours at room temperature. The solvent is evaporated and the residue taken up in water and the pH is adjusted to 5. The aqueous mixture is then extracted with methylene chloride (4×10 mL). Combined organic extract is dried ($MgSO_4$), filtered and evaporated to give an oil which is crystallized from ether to give 8-(p-chlorophenylsulfonamido)-5-[2-(3-pyridyl)ethyl]-octanoic acid, m.p. 83−85°.

EXAMPLE 10

Prepared substantially according to procedures described in examples 8 and 9 are:
(a) 8-beta-naphthylsulfonamido-5-[2-(3-pyridyl)-ethyl]-octanoic acid;
(b) 8-(p-trifluoromethylphenylsulfonamido)-5-[2-(3-pyridyl)ethyl]-octanoic acid;
(c) 8-phenylsulfonamido-5-[2-(3-pyridyl)ethyl]-octanoic acid;
(d) 8-(p-fluorophenylsulfonamido)-5-[2-(3-pyridyl)-ethyl]-octanoic acid.

EXAMPLE 11

Methyl 8-amino-6-(3-pyridylmethyl)-octanoate (0.5 g) is dissolved in 50 mL of methylene chloride and 3 mL of triethylamine is added. To this solution is added dropwise a solution of 0.5g of p-chlorobenzenesulfonyl chloride in 10 mL of methylene chloride. The reaction is stirred at room temperature for 1 hour, the solvent is evaporated and the residue thus obtained purified by chromatography over silica gel, using methylene chloride as eluent to obtain methyl 8-(p-chlorophenylsulfonamido)-6-(3-pyridylmethyl)-octanoate as an oil.

The starting material is prepared as follows:

To a suspension of 69g of 5-carboxypentyl-triphenylphosphonium bromide in a mixture of 125 mL of DMSO and 250 mL THF cooled to 20° is added 130 mL of a 2.4M solution of n-butyllithium dropwise over a period of 30 minutes. After stirring for 45 minutes a solution of 10.7g 3-pyridine-carboxaldehyde in 25 mL of THF is added dropwise, then the solution is stirred for 1 hour before adding water and ethyl acetate. The aqueous layer is separated, acidified to pH 6 and extracted with ethyl acetate. The ethyl acetate extract is dried over magnesium sulfate, filtered and concentrated to give 7-(3-pyridyl)-hept-6-enoic acid which is converted to methyl 7-(3-pyridyl)-hept-6-enoate by refluxing in methanolic hydrochloric acid.

11 g of methyl 7-(3-pyridyl)-hept-6-enoate is dissolved in a mixture of 100 mL of acetone and 50 mL of water, the solution is cooled to 0° and 13.5 g of N-bromosuccinimide added. The reaction is allowed to warm up to room temperature and stirred for 2 hours. The reaction mixture is diluted with 250 mL of water, extracted with ethyl acetate and then with 1N aqueous HCl. The aqueous layer is made basic with aqueous ammonium hydroxide and extracted with ethyl acetate. The ethyl acetate extract is dried over MgSO4, filtered and concentrated to give methyl 6-bromo-7-hydroxy-7-(3-pyridyl)-heptanoate.

16.3 g of methyl 6-bromo-7-hydroxy-7-(3-pyridyl)-heptanoate is dissolved in 200 mL of THF and 4.5 g of 50% sodium hydride added in portions. After stirring at room temperature for 3 hours, the reaction is diluted with ethyl acetate, filtered and concentrated to give crude product which is further purified by column chromatography on silica gel using ethyl acetate as eluent to yield 2-(3-pyridyl)-3-(4-methoxycarbonylbutyl)-oxirane.

The above compound (5 g) is dissolved in 100 mL of toluene, 200 mg of p-toluenesulphonic acid monohydrate is added and the reaction is heated to reflux for 8 hours. The reaction is cooled to room temperature, water is added, and the mixture is neutralized with sodium bicarbonate. The product is then extracted with ethyl acetate, the extract is dried over magnesium sulfate, filtered and concentrated to give the crude product which is further purified by column chromatography over silica gel using ethyl acetate as eluent to obtain methyl 7-(3-pyridyl)-6-oxoheptanoate.

A solution of the above compound (0.7 g) in 5 ml of toluene is added dropwise to a solution of a reagent prepared by adding 0.2 g of 50% sodium hydride in mineral oil to 0.7 g of diethyl cyanomethylphosphonate in 50 ml of toluene. After stirring at room temperature for 3 hours the reaction is poured into water and extracted with ethyl acetate. The ethyl acetate solution is dried over magnesium sulfate, filtered and concentrated to give crude product which is further purified by chromatography over silica gel using ethyl acetate as eluent to yield methyl 7-(3-pyridyl)-6-(cyanomethylidene)-heptanoate.

The above compound (0.6 g) is dissolved in 70 mL methanol saturated with ammonia gas, activated Raney-Nickel catalyst is added and the mixture hydrogenated for 6 hours at 3 atmospheres pressure. The catalyst is then filtered off and the methanol evaporated to give crude product which is directly dissolved in 50 mL of methanol, treated with 0.7 g of 10% palladium on charcoal catalyst and further hydrogenated at 3 atmospheres pressure for 8 hours. The catalyst is filtered off and the solvent concentrated to give methyl 8-amino-6-(3-pyridylmethyl)-octanoate as an oil.

EXAMPLE 12

Methyl 8-(p-chlorophenylsulfonamido)-6-(3-pyridylmethyl)-octanoate (0.3 g) is dissolved in 10 mL of methanol, 20 mL of 1N aqueous NaOH added and the reaction is stirred at room temperature overnight. The methanol is evaporated off, water added and the mixture extracted with ethyl acetate. The aqueous layer is acidified to pH 6.1 and extracted with ethyl acetate. The ethyl acetate extract is dried over magnesium sulfate, filtered and concentrated to give 8-(p-chlorophenylsulfonamido)-6-(3-pyridylmethyl)-octanoic acid, NMR (CDCl$_3$): delta 7.7 (d,2H), 7.4 (d,2H), 2.9 (m,2H).

EXAMPLE 13

Prepared substantially according to the procedures described in examples 11 and 12 are:
(a) 8-(beta-naphthylsulfonamido)-6-(3-pyridylmethyl)-octanoic acid;
(b) 8-(p-trifluoromethylphenylsulfonamido)-6-(3-pyridylmethyl)-octanoic acid;
(c) 8-(phenylsulfonamido)-6-(3-pyridylmethyl)-octanoic acid;
(d) 8-(p-fluorophenylsulfonamido)-6-(3-pyridylmethyl)-octanoic acid.

EXAMPLE 14

To a solution of 1.0 g of ethyl 8-amino-3-[4-(3-pyridyl)-butyl]-octanoate in 100 mL of methylene chloride is added 3 g of triethylamine followed by the dropwise addition of a solution of 1.5 g of p-chlorobenzenesulfonyl chloride in 15 mL of methylene chloride. The reaction mixture is concentrated then directly purified by chromatography on silica gel using 25% ethyl acetate in methylene chloride as eluent to yield ethyl 8-(p-chlorophenylsulfonamido)-3-[4-(3-pyridyl)-butyl]-octanoate.

The starting material is prepared as follows:

Methyl acetoacetate (34.8 g) is added dropwise to a suspension of 16.2 g of 50% sodium hydride in 750 mL of anhydrous tetrahydrofuran cooled to 0°. To this solution is added dropwise 141 mL of a 2.3M solution of n-butyllithium in hexane over 40 minutes keeping the temperature of the THF solution at 0°. To this solution is then added 36 g of a solution of allyl bromide in 150 mL of THF. After 10 minutes the reaction is worked up by pouring into a mixture of 60 mL of aqueous concentrated HCl, 150 mL of water and 500 mL of ether. The ether layer is separated, washed with water, dried over magnesium sulphate, filtered and evaporated to give methyl 3-oxo-hept-6-enoate.

The above compound (36 g) is combined with 40 g of 3-bromopyridine, 1.8 g of tri-o-tolyl-phosphine, 0.67 g of palladium acetate, 150 mL of triethylamine and 300 mL of acetonitrile and the mixture heated to reflux for 20 hours. The reaction is allowed to cool to room temperature, evaporated and the residue thus obtained partitioned between ethyl acetate and water. The ethyl acetate solution is dried over magnesium sulfate, filtered and evaporated to give crude product which is further purified by chromatography on silica gel using ether as eluent to obtain methyl 7-(3-pyridyl)-3-oxo-hept-6-enoate.

A solution of the above compound (23.3 g) in 50 mL of dimethylformamide (DMF) is added dropwise to a mixture of 5.5 g of 50% sodium hydride in 500 mL of DMF kept below 25°. After 30 minutes 19.4 g of 4-iodobutyronitrile in 50 mL of DMF is added and the reaction stirred at room temperature for 18 hours. The mixture is poured into 2000 mL of cold dilute brine solution and extracted with ethyl acetate. The ethyl acetate solution is dried over magnesium sulfate, filtered and concentrated to give crude product which is further purified by chromatography on 500 g of silica gel using ether as eluent to yield methyl 2-(3-cyanopropyl)-7-(3-pyridyl)-3-oxo-hept-6-enoate.

The above compound (8.1 g) is dissolved in a mixture of 75 mL of dimethylsulfoxide and 2.5 mL of water to which 5 g of sodium chloride is added. The solution is heated to reflux for 14 hours, is allowed to cool to room temperature, water (200 mL) is added and the mixture is extracted with ethyl acetate. The ethyl acetate solution is dried over $MgSO_4$, filtered and concentrated to give crude product which is further purified by chromatography over silica gel using a mixture of ethyl acetate/hexane (7:3) as eluent to yield the decarboxylated product, 10-(3-pyridyl)-6-oxo-dec-9-enenitrile.

A solution of 6.05 g of the above compound in 30 mL of toluene is added to the reagent prepared by treating a solution of 6.7 g of triethyl phosphonoacetate with 1.5 g of 50% sodium hydride in 130 mL of toluene. The reaction mixture is stirred at room temperature for 72 hours, then poured into water, adjusted to pH 6 with acetic acid then extracted with ethyl acetate. The ethyl acetate solution is dried over magnesium sulfate, filtered and concentrated to give crude product which is further purified by chromatography over silica gel using ether as eluent to yield 10-(3-pyridyl)-6-(ethoxycarbonylmethylidene)-dec-9-enenitrile.

To a solution of the above product (5.2 g) in 150 mL of ethyl acetate, 0.8 g of 10% palladium on charcoal catalyst is added and the mixture is hydrogenated at atmospheric pressure and room temperature for 4 hours. The catalyst is filtered off and the ethyl acetate solution evaporated to dryness to yield 10-(3-pyridyl)-6-(ethoxy- carbonylmethylidene)-decanenitrile.

A solution of the above compound (5.0 g) in 150 mL of methanol is saturated with ammonia gas and hydrogenated at 3 atmospheres pressure of hydrogen using Raney Nickel as the catalyst. The catalyst is filtered off and the methanol solution evaporated to dryness to yield ethyl 7-(3-pyridyl)-3-(5-aminopentyl)-hept-2-enoate, also called ethyl 8-amino-3-[4-(3-pyridyl)-butyl]-oct-2-enoate.

To a solution of 2.0 g of the above compound in 50 mL of methanol is added 2 g of 10% palladium on charcoal and the mixture is hydrogenated at 3 atmospheres pressure of hydrogen for 120 hours. The catalyst is filtered off and the methanol solution evaporated to give ethyl 7-(3-pyridyl)-3-(5-aminopentyl)-heptanoate, also called ethyl 8-amino-3-[4-(3-pyridyl)-butyl]-octanoate.

EXAMPLE 15

A solution of 0.7 g of ethyl 8-(p-chlorophenyl- sulfonamido)-3-[4-(3-pyridyl)-butyl]-octanoate, in a mixture of 50 mL of methanol and 100 mL of 1N aqueous NaOH is stirred at room temperature for 18 hours. The reaction mixture is then concentrated to remove the methanol. The product is neutralized with dilute aqueous hydrochloric acid, and the aqueous solution extracted with ethyl acetate. The ethyl acetate extract is dried over magnesium sulfate, filtered and concentrated to give 8-(p-chlorophenylsulfonamido)-3-[4-(3-pyridyl)-butyl]-octanoic acid, NMR ($CDCl_3$): delta 7.77 (d,2H), 7.43 (d,2H), 2.9 (t,2H), 2.6 (t,2H).

EXAMPLE 16

Prepared substantially according to procedures described in examples 14 and 15 are:
(a) 8-(beta-naphthylsulfonamido)-3-[4-(3-pyridyl)-butyl]-octanoic acid;
(b) 8-(p-trifluoromethylphenylsulfonamido)-3-[4-(3-pyridyl)-butyl]-octanoic acid;
(c) 8-phenylsulfonamido-3-[4-(3-pyridyl)-butyl]-octanoic acid.
(d) 8-(p-fluorophenylsulfonamido)-3-[4-(3-pyridyl)-butyl]-octanoic acid.

EXAMPLE 17

Methyl 7-amino-6-(3-pyridyl)-heptanoate hydrochloride (8.0 g) is suspended in 200 mL of ethyl acetate, 15 mL of triethylamine is added, and then a solution of 10 g of 4-chlorophenylsulfonyl chloride in 100 mL of ethyl acetate is added dropwise over a period of 0.5 hour. The reaction is then stirred for 2 hours and is extracted with 1N aqueous sodium hydroxide, washed with saturated aqueous sodium chloride, dried over magnesium sulfate and evaporated. The residue is chromatographed over activated magnesium silicate (Florisil) and eluted with ethyl acetate to yield methyl 7-(p-chlorophenylsulfonamido)-6-(3-pyridyl)-heptanoate as an oil.

The starting material is prepared as follows:

To a suspension of 8.6 g of sodium hydride (50% dispersion in mineral oil) in 200 mL of dimethylformamide is added in a solution of 17.7 g of 3-pyridylacetonitrile in 15 mL of dimethylformamide over a period of 0.5 hour. The reaction is stirred for a further 0.5 hour at room temperature, then cooled to −20° before adding 30 g of methyl 5-bromovalerate. The reaction is then allowed to warm up to room temperature over a period of several hours and left to stand for 18 hours. The reaction is then poured into 300 mL of ice water and extracted with 300 mL of ethyl acetate. The extract is washed with 3 portions of 75 mL of 1N hydrochloric acid and the aqueous solution neutralized with ammonium hydroxide and extracted with ethyl acetate. The extract is dried over magnesium sulfate, filtered and evaporated to yield methyl 6-cyano-6-(3-pyridyl)-hexanoate.

A solution of 17.0 g thereof in 100 mL of methanol and 30 mL of ethyl acetate saturated with HCl gas is hydrogenated over 1.5 g of 10% palladium on charcoal at 3 atmospheres pressure and room temperature until hydrogen uptake ceases. The reaction mixture is then filtered and evaporated and the residue triturated with ethyl acetate to yield methyl 7-amino-6-(3-pyridyl)-heptanoate hydrochloride.

EXAMPLE 18

A solution of 8 g of methyl 7-(p-chlorophenylsulfonamido)-6-(3-pyridyl)-heptanoate in 100 mL of methanol and 100 mL of 1N aqueous sodium hydroxide is stirred at room temperature for 24 hours, then evaporated to remove the methanol and acidified with 1N hydrochloric acid. The mixture is then extracted with ethyl acetate, the extract is dried over magnesium sulfate, filtered and evaporated, and the residue is treated with a saturated solution of HCl gas in ethyl acetate to yield 7-(p-chlorophenylsulfonamido-6-(3-pyridyl)-heptanoic acid hydrochloride, m.p. 169–172°.

EXAMPLE 19

Prepared substantially according to the procedures described in examples 17 and 18, starting from appropriate starting materials, are:

(a) 8-(phenylsulfonamido)-7-(3-pyridyl)-octanoic acid, m.p. 158–160°;
(b) 8-(p-chlorophenylsulfonamido)-7-(3-pyridyl)-octanoic acid hydrochloride, m.p. 107–110°;
(c) 8-(1-naphthylsulfonamido)-7-(3-pyridyl)-octanoic acid hydrochloride, m.p. 186–189°;
(d) 9-(p-chlorophenylsulfonamido)-8-(3-pyridyl)-nonanoic acid hydrochloride, m.p. 98–102°;
(e) 8-(2-naphthylsulfonamido)-7-(3-pyridyl)octanoic acid hydrochloride, m.p. 157–160°;
(f) 8-(3,4-dichlorophenylsulfonamido)-7-(3-pyridyl)octanoic acid hydrochloride, m.p. 152–154°;
(g) 7-(2-naphthylsulfonamido)-6-(3-pyridyl)-heptanoic acid hydrochloride, m.p. 124–127°;
(h) 7-(5-isoquinolinylsulfonamido)-6-(3-pyridyl)-heptanoic acid, m.p. 167° dec;
(i) 8-(p-methoxyphenylsulfonamido)-7-(3-pyridyl)octanoic acid hydrochloride, m.p. 144–146°;
(j) 6-(2-naphthylsulfonamido)-5-(3-pyridyl)-hexanoic acid hydrochloride, m.p. 88–91°;
(k) 6-(p-chlorophenylsulfonamido)-5-(3-pyridyl)-hexanoic acid hydrochloride, m.p. 100–103°;
(l) 8-(p-methylphenylsulfonamido)-7-(3-pyridyl)-octanoic acid hydrochloride, m.p. 152–154°;
(m) 8-(p-nitrophenylsulfonamido-7-(3-pyridyl)-octanoic acid hydrochloride, m.p. 155–158°;
(n) 8-(3-pyridylsulfonamido)-7-(3-pyridyl)-octanoic acid, m.p. 105–107°;
(o) 8-(p-aminophenylsulfonamido)-7-(3-pyridyl)-octanoic acid, m.p. 134–137°;
(p) 8-(p-carboxyphenylsulfonamido)-7-(3-pyridyl)-octanoic acid, m.p. 154–156°;
(q) 8-(p-trifluoromethylphenylsulfonamido)-7-(3-pyridyl)-octanoic acid hydrochloride m.p., 110–113°;
(r) 8-(o-methylphenylsulfonamido)-7-(3-pyridyl)-octanoic acid hydrochloride, m.p. 135–139°;
(s) 8-(phenylsulfonamido)-7-(3-pyridyl)-octanoic acid amide, m.p. 106–108°; from methyl ester by treatment with ammonia in methanol under pressure;
(t) methyl 8-(phenylsulfonamido)-7-(3-pyridyl)-octanoate hydrochloride, m.p. 110–112°;
(u) 8-(p-fluorophenylsulfonamido)-7-(3-pyridyl)-octanoic acid;
(v) 7-(8-quinolinylsulfonamido)-6-(3-pyridyl)-heptanoic acid, m.p. 193–196°.

EXAMPLE 20

A solution of 1.4 g of ethyl 8-(p-chlorophenyl-sulfonamido)-2-[5-(3-pyridyl)-pentyl]-2-(ethoxycarbonyl)-octanoate in 50 mL of 6N HCl and 10 mL of acetic acid is heated to reflux for 23 hours after which time it is evaporated to give an oil. This is treated with water, the solution is neutralized with solid sodium bicarbonate to a pH of 6.4 and extracted with ethyl acetate. The ethyl acetate extract is dried over magnesium sulfate, filtered and concentrated to give crude product which is first purified by column chromatography over silica gel using ethyl acetate as eluent, and then further purified by preparative TLC chromatography using ethyl acetate, acetic acid (99.5:0.5) as eluent to give 8-(p-chlorophenylsulfonamido)-2-[5-(3-pyridyl)pentyl]-octanoic acid as an oil, NMR (CDCl$_3$): delta 7.77 (d,2H), 7.4 (d,2H), 2.85 (t,2H), 2.55 (t,2H).

The starting material is prepared as follows:

To 300 mL of ethanol are added 5 g of sodium spheres and after a clear solution is obtained, 32.1 g of diethyl malonate is added in one portion. After 1 hour at room temperature, 15 g of 5-bromopent-1-ene is added and the reaction mixture is stirred at room temperature for 16 hours. The reaction mixture is evaporated to dryness and the residue is distilled under high vacuum to obtain diethyl pent-4-enylmalonate.

The above compound (16.0 g) is mixed with 15.8 g of 3-bromopyridine, 0.6 g of tri-o-tolylphosphine, 0.45 g of palladium acetate, 50 mL of triethylamine and 75 mL of acetonitrile, and the mixture is heated to reflux for 24 hours. The reaction mixture is allowed to cool, is evaporated to dryness and the residue is extracted with ether/water. The ether layer is separated, dried over magnesium sulfate, filtered and concentrated to give crude product which is further purified by chromatography on silica gel using ether as eluent to obtain ethyl 7-(3-pyridyl)-2-ethoxycarbonyl-hept-6-enoate.

The above compound (14 g) is dissolved in 100 mL of ethyl acetate, 0.8 g of 10% palladium on charcoal is added and the mixture is hydrogenated at 3 atmospheres pressure for 6 hours. The catalyst is removed by filtration and the ethyl acetate solution evaporated to dryness to give ethyl 7-(3-pyridyl)-2-ethoxycarbonyl-heptanoate.

The above compound (6 g) is added dropwise to a suspension of 1 g sodium hydride in 200 mL in DMF. After the addition is complete, the reaction is stirred at room temperature for 45 minutes and 3.6 g of 6-bromocapronitrile is added. The reaction mixture is stirred for 16 hours at room temperature, poured into ice-water, extracted with ethyl acetate. The ethyl acetate extract is dried over magnesium sulfate, filtered and concentrated to give ethyl 7-(3-pyridyl)-2-ethoxycarbonyl-2-(5-cyanopentyl)-heptanoate.

The above compound (4 g) is dissolved in 75 mL of methanol saturated with ammonia gas, activated Raney Nickel is added and the mixture hydrogenated in an atmosphere of hydrogen at 3 atmospheres pressure for 20 hours. The catalyst is filtered off and the methanol solution evaporated to give a residue which is taken up in ethyl acetate. The solution of the resulting amine is treated with 5 mL of triethylamine and 3 g of 4-chlorobenzenesulfonyl chloride. The reaction mixture is evaporated to give a residue which is purified by chromatography over silica gel using a mixture of ether/hexane (7:3) as eluent to yield ethyl 7-(3-pyridyl)-2-ethoxycarbonyl-2-[6-(p-chloro- phenylsulfonamido)-hexyl]-heptanoate, also named ethyl 8-(p-chlorophenyl-sulfonamido)-2-[5-(3-pyridyl)-pentyl]-2-(ethoxycarbonyl)-octanoate.

EXAMPLE 21

Prepared substantially as described in example 20, using 5-bromovaleronitrile instead of 6-bromocapronitrile, are:

(a) 7-(p-chlorophenylsulfonamido)-2-[5-(3-pyridyl)-pentyl]-heptanoic acid; NMR (CDCl$_3$) delta 7.75 (d,2H), 7.43 (d,2H), 2.88 (t,2H), 2.57 (t,2H);

(b) 7-(2-naphthylsulfonamido)-2-[5-(3-pyridyl)-pentyl]heptanoic acid; NMR (CDCl$_3$) delta 7.53 (m,3H), 2.9 (t,3H), 2.55 (t,2H).

EXAMPLE 22

(a) To a solution of 0.15 g of crude t-butyl (+)-4(R)-8-amino-4[3-(3-pyridyl)propyl]octanoate in 1 mL methylene chloride is added 0.15 mL triethylamine followed by 0.106 g (0.5 mmol) of p-chlorophenylsulfonyl chloride and a catalytic amount of 4-dimethylaminopyridine. The reaction is stirred at room temperature for 48 hours and then diluted with 50 mL ether. The organic solution is washed twice with 15 mL water, 15 mL brine, dried, filtered and evaporated to give an oil which is flash chromatographed using 4:6 ethylacetate and petroleum ether to obtain t-butyl (+)-4(R)-8-(p-chlorophenylsulfonamido)-4-[3-(3-pyridyl)propyl]-octanoate; NMR (CDCl$_3$): delta 7.9 (d,2H), 7.52 (d,2H), 1.45 (s,9H).

The starting material is prepared as follows:

To a solution of 20 mL (0.18 mmol) epsilon-caprolactone in 100 mL methanol is added 36 mL of 5N sodium hydroxide and the resulting mixture is heated at reflux for 8 hours. The solvent is evaporated and the residue is taken up in 200 mL ethanol. The precipitate is collected and the filtrate is evaporated. The residue is suspended in 50 mL ethanol and 300 mL ether is added. The precipitate is filtered off and combined with the earlier precipitate to obtain 6-hydroxyhexanoic acid sodium salt.

The sodium salt prepared above is suspended in 200 mL dimethylformamide and 14.1 g (0.21 mmol) imidazole is added followed by 56.5 g (0.37mmol) t-butyldimethylsilyl chloride. The mixture is stirred at room temperature for 52 hours. The mixture is then poured into 100 mL water and the resulting mixture is extracted thrice with 300 mL ether each. The combined organic extracts are washed thrice with 500 mL water, 300 mL brine, dried, filtered and evaporated to give a pale tan oil identified as t-butyldimethylsilyl 6-t-butyldimethylsilyloxyhexanoate.

The above silyl ester is dissolved in 600 mL methanol and 200 mL tetrahydrofuran and to the solution is added a solution of 77.65 g (0.56 mmol) potassium carbonate in 200 mL water. A two phase system is obtained which is made homogenous by adding 750 mL of a 3:1:1 mixture of methanol, tetrahydrofuran and water, respectively. After 1 hour of stirring, the mixture is concentrated to about a quarter of the total volume and then poured onto ice and adjusted to a pH of 6.3 by addition of aqueous sodium dihydrogen phosphate. The aqueous phase is extracted thrice with 500 mL ethyl acetate and the combined organic phase is washed with 500 mL brine. It is then dried, filtered and evaporated to give a pale yellow oil identified as 6-t-butyldimethylsilyloxyhexanoic acid. IR (CH$_2$Cl$_2$) 1709, 1096 cm$^{-1}$.

To a solution of 2.71 g (11 mmol) of 6-t-butyldimethylsilyloxyhexanoic acid in 20 mL toluene is added 2.0 mL of oxalyl chloride. The mixture is stirred at room temperature for 1 hour and then subjected to evaporation under vacuum to give the acid chloride as a pale yellow oil.

To a solution of 1.95 g (11 mmol) (−)-(S)-4-benzyl-2-oxazolidinone in 20 mL dry tetrahydrofuran at −78° C. is added dropwise 4.4 mL (11 mmol) of a 2.5 M solution of n-butyl lithium in hexane and the resulting mixture is stirred at −78° C. for 15 minutes. Then the acid chloride prepared above is added to the reaction mixture as a solution in 5 mL dry tetrahydrofuran. The 178° C. cooling bath is removed, the reaction mixture is stirred at room temperature for 1 hour and is then quenched using 50 mL saturated aqueous ammonium chloride. The reaction mixture is extracted with 200 mL ether and the resulting organic layer is washed with 50 mL water, 50 mL brine, dried, filtered and evaporated to give a pale yellow oil. Column chromatography using 15:85 ethyl acetate and petroleum ether yields a thick, clear, colorless oil which is identified as (+)-(4S)-3-[1'-oxo-6'-(t-butyldimethylsilyloxy)hexyl]-4-benzyl-2-oxazolidinone, [alpha]$_D^{25}$ +48.13° (12 mg/ml in methylene chloride).

To a solution of 1.2 mL (8.5 mmol) of diisopropyl amine in 25 mL dry tetrahydrofuran at 0° C. is added dropwise 2.8 mL (7.1 mmol) of a 2.5 M solution of n-butyllithium in hexane. The mixture is stirred at 0° C. and then cooled down to −78° C. A solution of 2.88 g (7.1 mmol) of (+)-(4S)-3- [1'-oxo-6'-(t-butyldimethylsilyloxy)hexyl]-4-benzyl-2-oxazolidinone in 5 mL dry tetrahydrofuran is added to the reaction mixture which is then stirred at −78° C. for 30 minutes. At this time 3.1 mL (36.15 mmol) of allyl bromide is added quickly and the mixture is placed in a bath at −10° C. and stirred for 2 hours. The reaction is quenched using saturated aqueous ammonium chloride and then extracted with 200 mL ether. The organic layer is washed with 50 mL of water, 50 mL brine, dried, filtered and evaporated to get a pale yellow oil which is purified by chromatography to give (+)-3-[1'-oxo-2'(R)-allyl-6'- (t-butyldimethylsilyloxy)-hexyl]-4-(S)-benzyl-2-oxazolidinone, as a clear colorless oil, [alpha]$_D^{25}$ +52.37° (8.98 mg/mL in methylene chloride).

To a solution of 0.1 g (0.225 mmol) (+)-3-[1'-oxo-2'-(R)-allyl-6'-(t-butyldimethylsilyloxy)hexyl]-4-(S)-benzyl-2-oxazolidinone in 1 mL dry tetrahydrofuran at 0° C. is added 0.16 mL of a 2M solution of lithium borohydride in tetrahydrofuran and then the mixture is stirred at room temperature for 6 hours. The reaction mixture is quenched by slow addition of saturated aqueous ammonium chloride. The pH of the mixture is adjusted to 6.0 using 1N hydrochloric acid and then the mixture is extracted with 100 mL ether. The organic layer is washed with 25 mL water, 25 mL brine and then dried, filtered and evaporated to give an oil which is purified by flash chromatography using 1:9 ethyl acetate petroleum ether to obtain (−)-2(R)-allyl-6-t-butyldimethylsilyloxyhexan-1-ol; [alpha]$_D^{25}$ −2.38° (7.5 mg/ml in methylene chloride).

A solution of 0.59 g (2.16 mmol) of (−)-2(R)-allyl-6-t-butyldimethylsilyloxyhexan-1-ol in 10 mL dry methylene chloride is cooled to 0° C. and 2 mL triethylamine is added followed by dropwise addition of 0.25 mL methanesulfonyl chloride. The cooling bath is removed and the reaction mixture is allowed to stir for 2 hours at which time it is diluted with 100 mL ether, washed twice with 50 mL water and 50 mL brine. The organic layer is dried, filtered and evaporated to an amber oil, which is the mesylate derivative.

The crude mesylate is dissolved in 10 mL acetone under nitrogen and 4 drops of pyridine are added, followed by 2 g of sodium iodide. The mixture is refluxed for 2 hours and then the reaction mixture is diluted with 100 mL ether, washed with 50 mL water, 50 mL 10% aqueous sodium thiosulfate and 50 mL brine. The organic layer is then dried, filtered and evaporated to get a light amber oil which is chromatographed using 3:97 ethyl acetate and petroleum ether to obtain (+)-5(S)-allyl-6-iodo-1-t-butyldimethylsilyloxyhexane as a clear colorless oil; [alpha]$_D^{25}$ +2.34° (9.8 mg/ml in $CH_2Cl_2$).

To a solution of 0.66 mL (4.0 mmol) of isopropylcyclohexylamine in 2.5 mL dry tetrahydrofuran at 0° C. is added dropwise 1.2 mL (3.0 mmol) of 2.5 M solution of n-butyl-lithium in hexane. The mixture is stirred at 0° C. for 15 minutes and then cooled down to −78° C.; 0.4 mL (3.0 mmol) of t-butyl acetate is added and the mixture is stirred at −78° C. for 30 minutes. Then a solution of 0.58 g (1.5 mmol) of (+)-5(S)-allyl-6-iodo-1-t-butyldimethylsilyloxyhexane in 2.5 mL hexamethylphosphoric triamide (HMPA) and 1 mL dry tetrahydrofuran is added and the reaction flask is placed in a bath at −25° C. The reaction is allowed to warm up to 0° C. in the bath at which time the reaction is quenched using 15 mL saturated aqueous ammonium chloride. The mixture is extracted with 150 mL ether and the organic layer is washed twice with 50 mL water and 50 mL brine. The organic layer is then dried, filtered and evaporated to give an oil which is chromatographed using 3:97 ethyl acetate/petroleum ether to obtain t-butyl (+)-4(S)-8-t-butyldimethylsilyloxy-4-allyloctanoate; ms: 371, 315.

To a solution of 0.37 g (1.0 mmol) t-butyl (+)-8-t-butyldimethylsilyloxy-4-allyloctanoate in 1 mL triethylamine and 1 mL acetonitrile is added 0.014 g of palladium (II) acetate followed by 0.105 g (0.35 mmol) of tri-o-tolylphosphine and 0.12 mL (1.25 mmol) of 3-bromopyridine. The mixture is then heated at 125° for 36 hours. The reaction mixture is diluted with 100 mL ether and washed with 15 mL water and 15 mL brine. The organic layer is dried, filtered and evaporated to give an amber oil which is chromatographed using 3:7 ether and hexane to obtain t-butyl (+)-4(S)-8-t-butyldimethylsilyloxy-4- 3-(3-pyridyl)prop-2-enyl]octanoate; NMR ($CDCl_3$) delta 6.27 (m,2H), 3.5 (t,2H).

To a solution of 0.381 g of t-butyl (+)-4(S)-8-t- butyldimethylsilyloxy-4-[3-(3-pyridyl)prop-2-enyl]octanoate in 15 mL ethyl acetate is added 50 mg of 10% palladium on charcoal. The mixture is hydrogenated at room temperature and 3 atmospheres pressure for 18 hours. Then the mixture is filtered, evaporated and chromatographed using 4:6 ether and hexane to give t-butyl (+)-4(R)-8-t-butyldimethylsilyloxy-4-[3-(3-pyridyl)-propyl]-octanoate, as a colorless oil; IR ($CH_2Cl_2$) 1722, 1461 cm$^{-1}$.

To a round bottom flask containing 0.32 g (0.7 mmol) t-butyl (+)-4(R)-8-t-butyldimethylsilyloxy-4-[3-(3-pyridyl)propyl]octanoate is added 4 mL of a 1M solution of tetra-n-butylammonium fluoride in tetrahydrofuran and the resulting solution is stirred at room temperature for 3 hours. The reaction is quenched using 10 mL saturated aqueous ammonium chloride and then extracted with 75 mL ethyl acetate. The organic layer is washed with 10 mL water, 10 mL brine, filtered and evaporated to give a pale yellow oil which is chromatographed using 8:2 ethyl acetate and petroleum ether to give t-butyl (+)-4(R)-8-hydroxy-4- [3-(3-pyridyl)-propyl]-octanoate as a clear colorless oil, [alpha]$_D^{25}$ +2.2° (15 mg/ml in methylene chloride).

To a solution of 0.225 g (0.67 mmol) t-butyl (+)-4(R)-8-hydroxy-4-[3-(3-pyridyl)propyl]octanoate in 1 ml dry methylene chloride is added 0.5 mL triethyl amine. The solution is cooled to 0° C. and 0.077 mL (1.0 mmol) methanesulfonyl chloride is added. The mixture is stirred for 2 hours. The reaction mixture is diluted with 75 mL ether and washed twice with 5 mL water and 5 mL brine. The organic layer is dried, filtered and evaporated to give a yellow oil which is identified as the 8-mesylate derivative and is used as is.

To a solution of the above mesylate in 1 mL dry dimethylformamide is added 0.13 g (2.0 mmol) sodium azide and the mixture is stirred at room temperature for 15 hours and at 60° for 3 hours. The reaction mixture is diluted with 100 mL ether and washed twice with 10 mL water and 10 mL brine. The organic layer is dried, filtered and evaporated to get 0.2 g of an oil which is chromatographed using 3:7 ethyl acetate and petroleum ether to give t-butyl (+)-4(R)-8-azido-4-[3-(3-pyridyl)-propyl]octanoate as a clear colorless oil; IR ($CH_2Cl_2$) 2099, 1722 cm$^{-1}$.

To a solution of 0.169 g (0.469 mmol) t-butyl (+)-4(R)-8-azido-4-[3-(3-pyridyl)propyl]octanoate in 1.2 mL tetrahydrofuran is added 0.135 g triphenylphosphine and 0.020 mL water. The reaction mixture is stirred for 18 hours at room temperature. An additional 0.01 g triphenylphosphine and 1 drop of water are added and the mixture is further stirred for 6 hours. The solvent is evaporated and the residue is chromatographed using ethyl acetate to remove triphenylphosphine and triphenylphosphine oxide. The product is then eluted using 10:1 methanol and triethylamine to obtain t-butyl (+)-4(R)-8-amino-4-[3-(3-pyridyl)-propyl]octanoate.

(b) Similarly prepared is t-butyl (−)-4(S)-8-(p- chlorophenyl-sulfonamido)-4-[3-(3-pyridyl)propyl]-octanoate.

(c) Similarly prepared is methyl 6-(p-chlorophenyl-sulfonamido)-2-[3-(3-pyridyl)propyl]-hexanoate.

The starting material for compound of example 22(c) is also prepared as follows:

Dry powdered potassium carbonate (1944 g) is added to 11.54 L of acetone followed by 1.0 Kg methyl 2-oxocyclopentane-1-carboxylate. Allyl bromide (936.2 g) is added over 10 minutes. The reaction mixture is stirred and heated under reflux for 5 hours. The reaction mixture is evaporated to dryness and the residue is distilled under reduced pressure to yield methyl 1-allyl-2-oxocyclopentane-1-carboxylate, b.p. 66–68°/0.45 mm.

Methyl 1-allyl-2-oxocyclopentane-1-carboxylate (1.1 Kg) is added to 1,100 mL of methanol previously saturated with ammonia gas at ice bath temperature. The reaction mixture is stirred first at ice bath temperature and then at room temperature overnight with constant introduction of ammonia. The reaction mixture is evaporated to dryness to yield starting material and a mixture of 5-carbomethoxyoct-7-enoic acid amide and methyl 5-carbomethoxy-oct-7enoate. The residue is distilled under reduced pressure to yield a mixture of the diester and ester amide. A portion (25 g) is added dropwise over 40 minutes to 23.6 g of thionyl chloride and the mixture is heated at 80° for 30 minutes. The reaction mixture is evaporated to dryness under water vacuum and then distilled under high vacuum to yield 5-carbomethoxy-oct-7-enenitrile.

A mixture of 23.5 g of 5-carbomethoxy-oct-7-enenitrile, 20.07 g of 3-bromopyridine and 0.79 g of tri-o-tolylphosphine in 200 mL of 2:1 acetonitrile and triethylamine is stirred at room temperature under nitrogen for one half hour. Palladium acetate (0.27 g) is added and the mixture is stirred under reflux for 40 hours. An additional 0.13 g of palladium acetate is added and the reaction mixture is further heated under reflux for 20 hours. The reaction mixture is evaporated to dryness and the residue is taken up in ethyl acetate. The ethyl acetate solution is washed with water, and then with 3N hydrochloric acid. The acid extract is washed with ethyl acetate, made basic to pH 8–9 with ammonium hydroxide solution and reextracted with ethyl acetate. The ethyl acetate extract is dried and evaporated to dryness to yield 5-carbomethoxy-8-(3-pyridyl)-oct-7-enenitrile.

A mixture of 8.7 g of 5-carbomethoxy-8-(3-pyridyl)-oct-7-enenitrile and 4.35 g of 5% rhodium on alumina in 87 mL of methanol saturated with ammonia (7.4N) is hydrogenated at room temperature for about 6 hours. Additional catalyst is added if required. The reaction mixture is then worked up to yield methyl 6-amino-2-[3-(3-pyridyl)propyl]hexanoate.

EXAMPLE 23

(a) To a solution of 0.136 g (0.26 mmol) of t-butyl (+)-4(R)-8-(p-chlorophenylsulfonamido)-4-[3-(3-pyridyl)-propyl]octanoate in 1 mL methanol is added 0.6 mL of 1N sodium hydroxide and then the solution is heated at 60° for 52 hours. The reaction mixture is then diluted with 15 mL water and washed with 10 mL ether. The aqueous layer is acidified to pH=5.5 using 0.6 mL 1N hydrochloric acid. The white precipitate is extracted with 3×50 mL ethyl acetate and the combined organic phase is washed with brine, dried, filtered and evaporated to give an oil which is triturated with 15 mL ether. The resulting colorless solid is dried under vacuum to give, (+)-4(R)-8-(p-chlorophenylsulfonamido)-4-[3-(3-pyridyl)propyl]octanoic acid, m.p. 106–109° C., $[alpha]_D^{25}$ + 0.59° (10 mg/ml in methylene chloride).

b) Similarly prepared is (−)-4(S)-8-(p-chlorophenylsulfonamido)-4-[3-(3-pyridyl)-propyl]-octanoic acid; NMR (CDCl$_3$) delta 7.83 (d,2H), 7.43 (d,2H), 2.3 (t,2H).

c) Similarly prepared is racemic 8-(p-chlorophenylsulfonamido)-4-[3-(3-pyridyl)-propyl]-octanoic acid, m.p. 114–116° (of example 5a).

EXAMPLE 24

A mixture of 0.313 g 8-(p-chlorophenylsulfonamido)-4-[3-(3-pyridyl)-propyl]-octanoic acid and 10 mL thionyl chloride is refluxed for 1 hour, and excess thionyl chloride is evaporated. The residue is taken up in 20 mL methylene chloride and the solution is cooled in an ice bath and ammonia is bubbled into the solution for 1 hour. The suspension is stirred under ammonia for 2 hours. The reaction mixture is washed with water, dried, filtered and evaporated to give an amber oil. Flash column chromatography using ethyl acetate and methanol (9:1) as the eluent gives an oil which is crystallized from ether to yield 8-(p-chlorophenylsulfonamido)-4-[3-(3-pyridyl)-propyl]-octanamide, m.p. 100–102° C.

EXAMPLE 25

To a solution of 0.312 g methyl 8-(p-chlorophenylsulfonamido)-4-[3-(3-pyridyl)-propyl]-octanoate in 5 mL isopropanol is added a solution of a catalytic amount of sodium hydride in 1 mL isopropanol. The mixture is refluxed for 18 hours and the solvent is evaporated. The residue is dissolved in methylene chloride and the solution is washed with saturated ammonium chloride solution. The organic phase is dried, filtered, evaporated to give a clear oil which is purified by flash column chromatography using ethyl acetate and hexane (2:3) as the eluent to give as a clear oil isopropyl 8-(p-chlorophenylsulfonamido)-4-[3-(3-pyridyl)-propyl]-octanoate.

EXAMPLE 26

To a solution of 0.378 g of 2,2-dimethyl propanol in 3 mL tetrahydrofuran is added 0.003 mL of 2.5 M n-butyllithium in hexane. To this solution is added 0.332 g methyl 8-(p-chlorophenylsulfonamido)-4-[3-(3-pyridyl)-propyl]-octanoate and the mixture is refluxed for 20 hours. The reaction is quenched by addition of 3 mL of saturated ammonium chloride solution. It is then extracted with methylene chloride (3×10 mL). The combined organic extracts are dried, filtered and evaporated to dryness to give a clear oil which is purified by preparative thin layer chromatography to obtain 2,2-dimethylpropyl 8-(p-chlorophenyl-sulfonamido)-4-[3-(3-pyridyl)-propyl]-octanoate as a pale yellow oil.

EXAMPLE 27 a) Treatment of ethyl 8-amino-3-[4-(3-pyridyl)-butyl]-oct-2-enoate (see Example 14) with p-chlorobenzenesulfonyl chloride according to procedure of example 14 yields ethyl 8-(p-chlorophenylsulfonamido)-3-[4-(3-pyridyl)-butyl]-oct-2-enoate.

b) Hydrolysis of ethyl 8-(p-chlorophenyl-sulfonamido)-3-[4-(3-pyridyl)-butyl]-oct-2-enoate according to example 5 yields 8-(p-chlorophenylsulfonamido)-3-[4-(3- pyridyl)-butyl]-oct-2-enoic acid; NMR (CDCl$_3$): delta 7.77 (d,2H), 7.43 (d,2H), 2.9 (t,2H), 2.6 (t,2H), 2.2 (d, 2H).

EXAMPLE 28

To a solution of 0.218 g methyl 8-(p-chlorophenylsulfonamido)-4-(2-methanesulfonyloxyethyl)octanoate in 2 mL dimethylformamide is added 0.101 g imidazole and then the solution is heated at 100° for 8 hours. The mixture is poured into water and extracted with ethyl acetate. The organic phase is washed with water (2×20 mL), dried, filtered and evaporated to give 0.184 g of an amber oil which is purified by preparative thin layer chromatography using ethyl acetate as eluent to give methyl 8-(p-chlorophenylsulfonamido)-4-[2-(1-imidazolyl)ethyl]-octanoate as a yellow oil.

The starting material is prepared as follows:

Ammonia (75 mL) is liquified in a flask at −40° and a solution of 5 g (28 mmol) of p-(4-hydroxybutyl)anisole in 25 mL ethanol is added. 2.76 g (0.12 mmol) of sodium is added in small pieces over 1 hour. The blue solution is then stirred at −40° for 10 minutes during which time the solution decolorizes with the formation of a white precipitate. The reaction is quenched using 5.88 g solid ammonium chloride followed by 25 mL water. The solvent is evaporated under a stream of nitrogen and then poured into brine and extracted with ether (4×100 mL). The organic extracts are combined, dried, filtered and subjected to evaporation to give 1-methoxy-4-(4-hydroxybutyl)cyclohexa1,4-diene as an oil.

A suspension of 4.76 g of 1-methoxy-4-(4-hydroxybutyl)cyclohexa-1,4-diene in 75 mL 1N sulfuric acid is stirred at room temperature for 1½ hours and extracted with methylene chloride (2×40 mL). The combined organic extracts are washed with saturated sodium bicarbonate, dried (MgSO$_4$), filtered and subjected to evaporation to obtain 4-(4-hydroxybutyl)cyclohex-3-ene-1-one as an oil.

To a solution of 4.63 g of 4-(4-hydroxybutyl)-cyclohex-3-ene-1-one in 130 mL acetone is added 0.46 of 10% palladium on carbon and the suspension is then hydrogenated at 3 atmospheres pressure for 3 hours. The catalyst is evaporated to dryness to give 4-(4-hydroxybutyl)cyclohexanone as an oil.

To a solution of 4.47 g of 4-(4-hydroxybutyl) cyclohexanone in 80 mL methylene chloride is added 6.81 g of 80-85% m-chloroperbenzoic acid and the mixture is stirred at room temperature for 3 hours. The reaction is quenched by addition of saturated aqueous sodium sulfite solution. The mixture is then poured onto a 10% solution of sodium bicarbonate and the layers are separated. The organic phase is dried, filtered and evaporated to dryness to yield 4-(4-hydroxybutyl)-epsilon-caprolactone as a clear oil.

To a solution of 3.53 g of 4-(4-hydroxybutyl)-epsilon-caprolactone in 14 mL methylene chloride and 14 mL tetrahydrofuran is added 4.24 g p-chlorophenylsulfonamide followed by 7.44 g triphenylphosphine. The reaction mixture is stirred at room temperature for one half hour and then 6.1 mL diethyl azodicarboxylate is added slowly with cooling. After the addition, the cooling bath is removed and the solution is stirred at room temperature overnight. The reaction mixture is evaporated to dryness to yield 4-[4-(p-chlorophenylsulfonamido)-butyl]-epsilon-caprolactone.

The above residue is dissolved in 100 mL methanol and 60 mL of 2N sodium hydroxide is added. After stirring overnight at room temperature, the solvent is evaporated and the residue taken up in water. The white precipitate is filtered off and washed with water (3×10 mL). The combined aqueous layer is washed with ether and ethyl acetate (1:1, 3×50 mL). Then the aqueous phase is acidified to pH=5 and extracted with methylene chloride (3×50 mL). The combined organic extracts are washed with water, brine, dried, filtered and evaporated to yield 8-(p-chlorophenylsulfonamido)-4-(2-hydroxyethyl)-octanoic acid as an oil.

The above product (3.55 g) is dissolved in 80 mL methanol and 1.4 mL thionyl chloride is added dropwise. After 2 hours, the reaction is poured into water and extracted with methylene chloride (1×300 mL, 2×100 mL). The combined organic extracts are dried, filtered and evaporated to give an oil which is purified by flash chromatography on silica gel to obtain a yellow oil identified as methyl 8-(p-chlorophenylsulfonamido)-4-(2-hydroxyethyl)octanoate.

A solution of 0.174 g of methyl 8-(p-chlorophenylsulfonamido)-4-(2-hydroxyethyl)octanoate in 2 mL methylene chloride is cooled to 0° C. and 0.1 mL of triethylamine is added followed by 0.042 mL of methanesulfonyl chloride. After 1 hour, the reaction is washed with saturated sodium bicaronate and the organic layer is dried, filtered and evaporated to yield methyl 8-(p-chlorophenylsulfonamido)-4-(2-methanesulfonyloxyethyl)-octanoate as an oil.

EXAMPLE 29

A solution of 0.117 g of methyl 8-(p-chlorophenylsulfonamido)-4-[2-(1-imidazolyl)ethyl]-octanoate in 3 mL methanol is mixed with 0.55 mL 1N sodium hydroxide. The mixture is heated at 50° for 4 hours. The reaction mixture is neutralized with 0.55 mL 1N hydrochloric acid and the solvent is evaporated. The residue is triturated with methylene chloride and the organic layer evaporated to dryness. The yellow oil is triturated with ether to obtain 8-(p-chlorophenylsulfonamido)-4-[2-(1-imidazolyl)ethyl]-octanoic acid as a crystalline solid, NMR (CDCl$_3$): delta 7.82 (d,2H), 7.45 (d,2H), 4.15 (m,2H), 2.35 (t,2H).

EXAMPLE 30

To a solution of 1.2 g of methyl 8-(p-chlorophenylsulfonamido)-4-(2-hydroxyethyl)octanoate in 12 mL methylene chloride is added 1.14 g triphenylphosphine followed by 0.336 g 3-hydroxypyridine. After stirring for 5 minutes, 0.55 mL diethyl azodicarboxylate is added slowly. After 1 hour, solvent is evaporated and the residue subjected to flash chromatography to obtain methyl 8-(p-chlorophenylsulfonamido)-4-[2-(3-pyridyloxy)ethyl]octanoate, m.p. 57-58°.

EXAMPLE 31

To a solution of 0.815 g of methyl 8-(p-chlorophenylsulfonamido)-4-[2-(3-pyridyloxy)ethyl]octanoate in 13 mL dioxane is added 3.5 mL of 1N sodium hydroxide. The solution is stirred at room temperature for 60 hours and then the solvent is evaporated. The residue is dissolved in water, the solution is adjusted to pH=6.5 and extracted with methylene chloride (3×20 mL). The combined organic extracts are dried, filtered and evaporated to yield an oil which is crystallized from ether to obtain 8-(p-chlorophenylsulfonamido)-4-[2-(3-pyridyloxy)ethyl]octanoic acid, m.p. 77-79°.

EXAMPLE 32

To a suspension of 0.545 g of 3-pyridylmethyltriphenylphosphonium chloride in 6 mL tetrahydrofuran is added slowly 1.6 mL of 1.61 M potassium t-butoxide in tetrahydrofuran and the mixture is stirred at room temperature for 1 hour. A solution of 0.454 g of methyl 8-(p-chlorophenylsulfonamido)-4-(formylmethyl)octanoate in 1 mL tetrahydrofuran is added slowly and then stirred for 18 hours at room temperature. The reaction mixture is poured into saturated ammonium chloride and extracted with ethyl acetate (3×15 mL). The combined organic extracts are dried, filtered and evaporated to give a dark residue which is purified by flash chromatography to obtain, as a light amber oil, methyl 8-(p-chlorophenylsulfonamido)-4-[3-(3-pyridyl)-2-propenyl]-octanoate. The product is a mixture of cis and trans isomers, the major component being the cis isomer. The above product is dissolved in 5 mL methylene chloride in a crystallizing dish and the solution is irradiated for 5 hours under UV light. The organic layer is diluted with methylene chloride and washed with aqueous sodium thiosulfate. The organic phase is dried, filtered and evaporated. The residue is purified by preparative thin layer chromatography to obtain a clear oil identified as about a 1:1 mixture of cis and trans isomers.

The starting material is prepared as follows:

A solution of 0.47 mL dimethylsulfoxide in 19 mL methylene chloride is cooled to −70° C. and 0.41 mL oxalyl chloride is added slowly. The solution is stirred at −70° C. for 15 minutes and a solution of 0.38 g of methyl 8-(p-chlorophenylsulfonamido)-4-(2-hydroxyethyl)octanoate in 1 mL methylene chloride is added slowly. The solution is stirred at −60° C. for 15 minutes and 1.9 mL triethylamine is added. The mixture is allowed to warm up to room temperature, washed with saturated sodium bicarbonate solution, and the organic phase is dried, filtered and evaporated to obtain a yellow oil. This oil is taken up in ether and washed with saturated sodium bicarbonate solution. The ether layer is dried, filtered and evaporated to yield methyl 8-(p-chlorophenylsulfonamido)4-(formylmethyl)-octanoate.

EXAMPLE 33

A mixture of 0.097 g of methyl 8-(p-chlorophenylsulfonamido)-4-[3-(3-pyridyl)-2-propenyl]octanoate in 1 mL dioxane and 0.45 mL 1N sodium hydroxide is stirred at room temperature for 18 hours. The mixture is acidified with 0.45 mL of 1N hydrochloric acid and then subjected to evaporation. The residue is triturated with methylene chloride and the organic phase is dried, filtered and evaporated to yield a light amber oil. The oil is dissolved in 1 mL t-butanol and one equivalent of potassium t-butoxide in tetrahydrofuran is added. The mixture is freeze-dried to obtain potassium 8-(p-chlorophenylsulfonamido)-4-[3-(3-pyridyl)-2-propenyl]octanoate as about a 1:1 mixture of cis and trans isomers.

EXAMPLE 34

(a) To a solution of 34 mg of 8-(p-chlorophenylsulfonamido)-4-[3-(3-pyridyl)-2-propenyl]octanoic acid in 2 mL of ethanol is added 5 mg of 10% palladium on carbon. The mixture is hydrogenated at 1 atmosphere pressure of hydrogen at room temperature for 48 hours. Then the mixture is filtered, washed and evaporated to give an oil which is purified by preparative thin layer chromatography using petroleum ether, ethyl acetate, acetic acid (80:18:2) as solvent to yield 8-(p-chlorophenylsulfonamido)-4-[3-(3-pyridyl)propyl]-octanoic acid of Example 5a.

(b) Similarly prepared is 8-(p-chlorophenylsulfonamido)-4-[3-(4-methyl-3-pyridyl)propyl]-octanoic acid, m.p. b 61–71°.

EXAMPLE 35 a) To a solution of 0.34 g methyl 8-amino-2,2-di-methyl-4-[3-(3-pyridyl)propyl]octanoate in 5 mL dry methylene chloride is added a catalytic amount of 4-dimethylaminopyridine followed by 0.2 mL triethylamine and the mixture is cooled to 0° C.; 0.208 g (0.96 mmol) p-chlorobenzenesulfonyl chloride is added, the reaction is allowed to warm to room temperature and stirred for 48 hours. The mixture is diluted with methylene chloride and washed with saturated sodium bicarbonate, water and brine. The organic phase is dried, filtered and evaporated to yield an amber oil which is purified by flash chromatography using 1:1 ethyl acetate,hexane to yield methyl 8-(p-chlorophenylsulfonamido)-2,2-dimethyl-4-[3-(3-pyridyl)-propyl]-octanoate; IR (CH$_2$Cl$_2$): 3381, 1729, 1164 cm$^{-1}$; NMR (CDCl$_3$): delta 3.57 (s,3H), 2.9 (q,2H), 2.53 (t,2H), 1.12 (s,6H).

b) Similarly prepared is methyl 8-(p-chlorophenylsulfonamido)-2-methyl-4-[3-(3-pyridyl)-propyl]-octanoate.

The starting materials are prepared as follows:

To a solution of 8.77 g (47 mmol) of 4-(4-hydroxybutyl)-epsilon-caprolactone (Example 28) in 52 mL dry dimethylformamide is added 6.16 g (90 mmol) of imidazole followed by 11.1 g (71 mmol) of t-butyldimethylsilyl chloride (97% pure) and then the mixture is stirred for 16 hours. The reaction mixture is poured into water and extracted twice with ether. The combined organic extracts are washed twice with water, brine, dried, filtered and concentrated to give an oil which is purified by flash chromatography using 3:2 hexane/ether to yield 4-(4-t-butyldimethylsiloxybutyl)-epsilon-caprolactone as an oil; NMR (CDCl$_3$): delta 4–4.3 (m,2H), 3.6 (t,2H), 0.88 (s,9H).

To a solution of 14.3 mL (0.1 mole) of diisopropylamine in 170 mL dry tetrahydrofuran is added dropwise 37 mL (93 mmol) of a 2.5 M solution of n-butyllithium in hexane. The solution is stirred for 15 minutes and then a solution of 13.86 g (46.1 mmol) of 4-(4-t-butyldimethylsiloxybutyl)-epsilon-caprolactone in 68 mL dry tetrahydrofuran is added slowly. The yellow solution is stirred at room temperature for 0.5 hour and 19 mL (0.3 mole) methyl iodide is added rapidly. The exothermic reaction is controlled by cooling in a water bath. The reaction is stirred for 3 hours and quenched using saturated aqueous ammonium chloride solution. The mixture is extracted with ether and the organic layer is washed with water and brine. The organic phase is dried, filtered, concentrated and purified by chromatography using 3:2 hexane, ether as eluent to yield 2-methyl-4-(4-t-butyldimethylsiloxybutyl)-epsilon-caprolactone; NMR (CDCl$_3$): delta 4-4.4 (m,2H), 3.6 (t,2H), 0.88 (s,9H), 1.2 (d,3H). This is converted to methyl 8-amino-2- methyl-4-[3-(3-pyridyl)-propyl]octanoate in a similar fashion as described below for the 2,2-dimethyl analog.

To a solution of 10 mL (65 mmol) diisopropylamine in 120 mL dry tetrahydrofuran is added dropwise 26 mL of a 2.5 M solution of n-butyllithium in hexane and the mixture is stirred for 15 minutes. To this solution is added slowly a solution of 10.11 g (32 mmol) of 2-methyl-4-(4-t-butyldimethylsiloxybutyl)-epsilon-caprolactone in 48 mL dry tetrahydrofuran. The mixture is stirred at room temperature for 35 minutes and 14.0 mL (0.22 mole) of methyl iodide is added rapidly while the flask is cooled in a water bath.

After stirring for 3½ hours, the reaction is quenched using saturated ammonium chloride solution and extracted with ether. The organic phase is washed with water and brine, dried, filtered and concentrated to give an amber oil which is purified by silica gel chromatography using 3:2 hexane, ether to give impure product. Further purification by a second silica gel chromatography using 4:1 hexane, ether as eluent yields 2,2-dimethyl-4-(4-t-butyldimethylsiloxy-butyl)- epsilon-caprolactone; NMR (CDCl$_3$): delta 4.32 (t,2H), 3.6 (t,2H), 1.3 (d,6H), 0.88 (s,9H).

To a solution of 2.35 g (7.2 mmol) of 2,2-dimethyl-4-4-t-butyldimethylsiloxybutyl)-epsilon-caprolactone in 22 mL methanol is added 0.386 g (7.2 mmol) sodium methoxide and the mixture is stirred for 2.5 hours. The reaction is quenched with saturated aqueous ammonium chloride and extracted twice with methylene chloride. The combined organic extracts are washed with water and brine, dried, filtered and evaporated to yield methyl 2,2-dimethyl-4-(2- hydroxyethyl)-8-(t-butyldimethylsiloxy)-octanoate as an oil; NMR (CDCl$_3$): delta 3.67 (s,3H), 3.55–3.65 (m,4H), 1.18 (s,6H), 0.89 (s,9H).

To a solution of 3.4 mL (48 mmol) dimethyl sulfoxide in 140 mL dry methylene chloride at −78° C. is added dropwise 3.0 mL (35 mmol) oxalyl chloride. The solution is stirred for 15 minutes and a solution of 2.57 g (7.1 mmol) methyl 2,2-dimethyl-4-(2-hydroxyethyl)-8-(t-butyldimethylsiloxy)octanoate in 20 mL dry methylene chloride is added slowly. The solution is stirred at −60° C. for 15 minutes and 15 mL (0.11 mole) triethylamine is added. The reaction is allowed to warm to room temperature and diluted with methylene chloride. The organic layer is washed with saturated aqueous sodium bicarbonate solution, water and brine. The organic phase is dried, filtered and concentrated to dryness. The oil is dissolved in ether and the solution is washed with water. The organic phase is dried, filtered and concentrated to give methyl 2,2-dimethyl-4-formylmethyl-8-(t-butyldimethylsiloxy)-octanoate; NMR (CDCl$_3$) delta 9.8 (t,1H), 3.67 (s,3H), 1.2 (s,6H), 0.89 (s,9H).

To a suspension of 8.8 g (22.6 mmol) 3-pyridyl-methyltriphenylphosphonium chloride in 40 mL dry tetrahydrofuran at 0° C. is added slowly 9.0 mL (22.5 mmol) of 2.5 M n-butyllithium in hexane. After stirring the resulting deep red solution at room temperature for 0.5 hour, a solution of 3.23 g (9 mmol) of methyl 2,2-dimethyl-4-(formylmethyl)-8-(t-butyldimethylsiloxy)octanoate in 10 mL dry tetrahydrofuran is added slowly and then stirred for 16 hours. The reaction is quenched by addition of saturated ammonium chloride solution and then extracted thrice with ether. The combined organic extracts are washed with water and brine, dried, filtered and concentrated. The residue is taken up in ether and the resulting precipitate is removed by filtration. The filtrate is evaporation and the residue is purified by silica gel chromatography using 1:1 hexane, ether to give methyl 2,2-dimethyl-4-[3-(3-pyridyl)-2-propenyl]-8-(t-butyldimethylsiloxy)octanoate; NMR (CDCl$_3$): delta 5.7–6.4 (m,2H), 3.63 and 3.60 (two s,3H), 1.2 and 1.15 (two s,6H).

To a solution of 1.83 g of methyl 2,2-dimethyl-4-[3-(3-pyridyl)-2-propenyl]-8-(t-butyldimethylsiloxy)-octanoate in 50 mL ethanol is added 0.18 g of 10% palladium on carbon. The mixture is hydrogenated at 3 atmospheres pressure in a Parr apparatus for 7.5 hours. The catalyst is filtered off and washed with ethanol. The solvent is evaporated to give methyl 2,2-dimethyl-4-[3-(3-pyridyl)-propyl]-8-(t-butyldimethylsiloxy)-octanoate as an oil; NMR (CDCl$_3$): delta 3.58 (s,3H), 3.55 (t,2H), 2.57 (t,2H), 1.13 (s,6H).

To a solution of 1.85 g (4.2 mmol) of methyl 2,2-dimethyl-4-[3-(3-pyridyl)propyl]-8-(t-butyldyldimethylsiloxy)-octanoate in 2 mL dry tetrahydrofuran is added 4.8 mL (4.8 mmol) of 1M tetra-n-butylammonium fluoride in tetrahydrofuran and the mixture is stirred for 1 hour. The reaction is quenched by addition of saturated ammonium chloride solution and the mixture is extracted with ethyl acetate. The organic phase is washed with water and brine, dried, filtered and concentrated. The residue is purified by silica gel chromatography using 4:1 ethylacetate, hexane as eluent to yield methyl 2,2-dimethyl-4-[3-(3-pyridyl)propyl]-8-hydroxyoctanoate as an oil; NMR (CDCl$_3$): delta 3.59 (s,3H), 3.6 (m,2H), 2.58 (t,2H), 1.21 (s,6H).

To a solution of 1.28 g (4 mmol) of methyl 8-hydroxy-2,2-dimethyl-4-[3-(3-pyridyl)propyl]octanoate in 20 mL methylene chloride at 0° C. is added 0.9 mL (6.5 mmol) triethylamine followed by 0.4 mL (5.2 mmol) methanesulfonyl chloride. After 1 hour, the reaction is diluted with methylene chloride and washed with saturated sodium bicarbonate, water and brine. The organic phase is dried, filtered and evaporated to give methyl 8-methanesulfonyloxy-2,2-dimethyl-4-[3-(3-pyridyl)-propyl]-octanoate as an oil.

The crude ester prepared above is dissolved in 20 mL dry dimethylformamide, 0.61 g (9.4 mmol) sodium azide is added and the mixture is heated at 60° C. for 16 hours. The reaction is cooled, poured into water and extracted thrice with ether. The combined organic extracts are washed with water and brine, dried, filtered and concentrated to give methyl 8-azido-2,2-dimethyl-4-[3-(3-pyridyl)propyl]-octanoate as an oil.

The crude azide (1.29 g) is dissolved in 7 mL dry tetrahydrofuran and 0.82 g (3.1 mmol) triphenylphosphine is added followed by two boiling stones and 0.08 mL (4.4 mmol) water. The solution is stirred for 14 hours. An additional 0.82 g triphenylphosphine and 0.08 mL water are added and the mixture is stirred for another 5 hours. The reaction mixture is concentrated under vacuum and then purified by silica gel chromatography using first ethyl acetate to remove non polar impurities and triphenylphosphine oxide. Then the eluent is changed to 9:1 methanol, triethylamine to obtain methyl 8-amino-2,2-dimethyl-4-(3-[3-pyridyl)propyl] octanoate as an oil; NMR (CDCl$_3$): delta 3.59 (s,3H), 2.67 (t,2H), 2.54 (t,2H), 1.13 (s,6H).

EXAMPLE 36 a) To a solution of 0.357 g (0.72 mmol) methyl 8-(p-chlorophenylsulfonamido)-2,2-dimethyl-4-[3-(3-pyridyl)-octanoate in 30 mL methanol is added 2.4 mL (2.4 mmol) 1N sodium hydroxide and the mixture is refluxed for 24 hours. The solvent is evaporated and the residue taken up in water and washed with ether. The aqueous phase is adjusted to pH=6.0 using 1N hydrochloric acid. The resulting mixture is extracted thrice with methylene chloride and the combined organic extracts are washed with water and brine, dried, filtered and evaporated to dryness. The resulting 8-(p-chlorophenylsulfonamido)-2,2-dimethyl-4-[3-(3-pyridyl)-propyl]octanoic acid (m.p. 114–115°) is dissolved in methanol and treated with 1 equivalent of methanolic sodium hydroxide solution. The solvent is evaporated and the resulting foam is triturated with hexane to get a white solid which is dried under vacuum to yield the sodium salt; NMR (D$_2$O): delta 2.93 (t,2H), 2.63 (t,2H), 1.15 (s,6H).

b) Similarly prepared is sodium 8-(p-chlorophenylsulfonamido)-2-methyl-4-[3-(3-pyridyl)-propyl]-octanoate; NMR (CD$_3$OD): delta 7.8 (d,2H), 7.55 (d,2H), 2.82 (t,2H), 2.6 (t,2H), 2.32 (m,1H), 1.05 (d,3H).

EXAMPLE 37

To a solution of 0.219 g ethyl 8-amino-4-[3-(3-pyridyl)propyl]-3-thia-octanoate in 1.5 mL methylene chloride is added a few crystals of 4-dimethylaminopyridine followed by 60 mcL triethylamine and 0.068 g p-chlorobenzenesulfonyl chloride. The mixture is stirred at room temperature for 18 hours, diluted with ether and washed with saturated aqueous sodium bicarbonate. The ether layer is dried, filtered and evaporated to leave an amber oil which is chromatographed using 3:2 ethyl acetate, hexane to give ethyl 8-(p-chlorophenylsulfonamido)-4-[3-(3-pyridyl)propyl]-3-thia-octanoate as an oil; NMR (CDCl$_3$): delta 8.0 (d,2H), 7.55 (d,2H), 3.15 (s,2H); such being the compound of formula X wherein X represents sulfur, Ar represents p-chlorophenyl, Het represents 3-pyridyl and R$_1$ represents ethoxy.

The starting material is prepared as follows:

To a solution of 8.5 g 5-hexen-1-ol in 100 mL tetrahydrofuran is added 14 mL dihydropyran followed by 0.5 g p-toluenesulfonyl chloride. The mixture is stirred at room temperature for 18 hours and then diluted with ether. The mixture is then washed with saturated aqueous sodium bicarbonate, dried, filtered and evaporated. The resulting oil is chromatographed over silica gel using hexane/ether (18:1) as eluent to give 6-(2-tetrahydropyranyloxy)-hex-1-ene; NMR (CDCl$_3$): delta 5.85 (m,1H), 4.6 (brs,1H).

To a solution of 11.57 g of 6-(2-tetrahydropyranyloxy)-hex-1-ene in 200 mL of methylene chloride is added 10.8 g m-chloroperbenzoic acid and the mixture is stirred at room temperature for 18 hours. The reaction is quenched by the addition of saturated aqueous sodium bicarbonate solution followed by saturated sodium sulfite solution. The organic phase is dried, filtered and evaporated to give a clear oil which is purified by chromatography over silica gel using hexane/ether (4:1) as eluent to obtain 1,2-epoxy-6-(2-tetrahydropyranyloxy)-hexane; IR (CH$_2$CH$_2$): 1450, 1135, 1033 cm$^{-1}$.

To a solution of 9.95 g (50 mmol) 1,2-epoxy-6-(2-tetrahydropyranyloxy)-hexane in 50 mL dimethylsulfoxide is added 5.2 g (51 mmol) of 90% lithium acetylide-ethylenediamine complex and the resulting mixture is stirred for 18 hours at room temperature. The reaction is quenched at 0° C. using 100 mL saturated ammonium chloride and 100 mL brine. It is then extracted thrice with 100 mL ethyl acetate. The combined organic extracts are dried, filtered and evaporated to leave an amber oil which is purified by chromatography over silica gel using hexane/ether (7:3) as eluent to yield 4-hydroxy-8-(2-tetrahydropyranyl-oxy)-1-octyne; IR (CH$_2$CH$_2$): 3584, 3304, 2114 cm$^{-1}$.

A mixture of 5.84 g (25.8 mmol) 4-hydroxy-8-(2-tetrahydropyranyloxy)-1-octyne, 4.7 mL diethylamine, 10 mL (100 mmol) 3-bromopyridine, 0.032 g copper (I) iodide, and 0.187 g bis-triphenylphosphine palladium (II) chloride is stirred at room temperature for 18 hours. The solvent is evaporated and the residue taken up in ether. The ether layer is washed with saturated aqueous sodium bicarbonate, water, brine, dried, filtered and evaporated to get an amber oil which is purified by chromatography using ether as the eluent to give 1-(3-pyridyl)-4-hydroxy-8-(2-tetrahydropyranyloxy)-1-octyne; NMR (CDCl$_3$): delta 4.6 (brs,1H), 2.6 (d,2H).

A mixture of 7.36 g (24 mmol) 1-(3-pyridyl)-4-hydroxy-8-(2-tetrahydropyranyloxy)-1-octyne, 100 mL ethanol and 0.74 g 10% palladium on charcoal is hydrogenated in a Parr apparatus at 3 atmospheres pressure and room temperature for 8 hours. The catalyst is filtered off and washed with ethanol. The combined filtrate is evaporated to give 5-hydroxy-8-(3-pyridyl)-1-(2-tetrahydropyranyloxy)-octane; NMR (CDCl$_3$) delta 4.4 (brs,1H), 2.67 (t,2H).

To a solution of 0.405 g (1.3 mmol) 5-hydroxy-8-(3-pyridyl)-1-(2-tetrahydropyranyloxy)-octane in 8 mL methylene chloride is added a few crystals of 4-dimethylaminopyridine followed by 0.5 mL (3.6 mmol) triethylamine and 0.5 g (2.6 mmol) p-toluenesulfonyl chloride. The reaction is stirred at room temperature for 18 hours and then diluted with ether. The ether layer is washed with saturated aqueous sodium bicarbonate, dried, filtered and evaporated to give an amber oil which is purified by chromatography over silica gel using ether/ethyl acetate (4:1) as eluent to yield 5-tosyloxy-8-(3-pyridyl)-1-(2-tetrahydropyranyloxy)-octane; NMR (CDCl$_3$): delta 7.9 (d,2H), 7.4 (d,2H), 2.45 (s,3H).

To a solution of 0.125 mL (1.1 mmol) ethyl 2-mercapto-acetate in 2.4 mL dimethylformamide is added 0.68 mL (1.1 mmol) of 1.61 M potassium t-butoxide in tetrahydrofuran. The solution is stirred at room temperature for 30 minutes and then a solution of 0.402 g (0.87 mmol) 5-tosyloxy-8-(3-pyridyl)-1-(2-tetrahydropyranyloxy)-octane in 1 mL dimethylformamide is added. The mixture is stirred at room temperature for 18 hours, poured into water and then extracted with ethyl acetate. The organic phase is washed with water, brine, dried, filtered and evaporated to give an orange oil which is purified by preparative thin layer chromatography using ether, hexane (4:1) as the eluent to give ethyl 8-(2-tetrahydropyranyloxy)-4-[3-(3-pyridyl)-propyl]-3-thia-octanoate; IR (CH$_2$Cl$_2$): 1729, 1134 cm$^{-1}$.

To a solution of 0.241 g (0.59 mmol) ethyl 8-(2-tetrahydropyranyloxy)-4-[3-(3-pyridyl)propyl]-3thia-octanoate in 1 ml tetrahydrofuran is added 1 mL of 1N hydrochloric acid. After stirring for 1 hour at room temperature, thin layer chromatography indicates incomplete conversion. Another 0.35 mL of 6N hydrochloric acid is added and the mixture is stirred for 1 hour. The pH of the reaction mixture is then adjusted to 8.0 and the resulting solution is extracted with methylene chloride. The organic layer is washed with brine, dried, filtered and evaporated to give yellow oil which is purified by preparative thin layer chromatography over silica gel using ether/ethyl acetate (4:1) as eluent to give ethyl 8-hydroxy-4-[3-(3-pyridyl)propyl]-3-thia-octanoate; IR (CH$_2$Cl$_2$) 3679, 1730 cm$^{-1}$.

A solution of 0.094 g (0.29 mmol) ethyl 8-hydroxy-4-[3-(3-pyridyl)propyl]-3-thia-octanoate in 1.5 mL methylene chloride is cooled to 0° and then 0.1 mL of triethylamine is added followed by 0.027 mL methanesulfonyl chloride. The reaction is stirred at 0° C. for 1 hour and diluted with ether. The ether layer is washed with saturated sodium bicarbonate, water, brine, then dried, filtered and evaporated to yield ethyl 8-methanesulfonyloxy-4-[3-(3-pyridyl)propyl]-3-thia-octanoate; NMR (CDCl$_3$): delta 3.2 (s,2H), 3.1 (s,3H).

A mixture of 0.12 g (0.3 mmol) ethyl 8-methanesulfonyloxy-4-[3-(3-pyridyl)propyl]-3-thia-octanoate, 1.5 mL dimethylformamide and 0.062 g (0.95 mmol) sodium azide is heated at 60° C. for 18 hours. The mixture is then poured into water and extracted with ether. The organic phase is washed with water, saturated brine, dried, filtered and evaporated to give ethyl 8-azido-4-[3-(3-pyridyl)propyl]-3-thia-octanoate; IR (CH$_2$Cl$_2$) 2099, 1732 cm$^{-1}$.

To a solution of 0.1 g (0.28 mmol) ethyl 8-azido-4-[3-(3-pyridyl)propyl]-3-thia-octanoate in 0.7 mL tetrahydrofuran is added 0.082 g triphenylphosphine followed by 0.01 mL water. The mixture is stirred at room temperature for 52 hours and then evaporated to give ethyl 8-amino-4-[3-(3-pyridyl)-propyl]-3-thia-octanoate, NMR (CDCl$_3$) delta 4.2 (q,2H), 3.2 (s,2H).

EXAMPLE 38

Prepared similarly to procedure described in Example 37 is methyl 8-(p-chlorophenylsulfonamido)-4-[3-(3-pyridyl)-propyl]-3-oxa-octanoate.

The intermediate methyl 8-hydroxy-4-[3-(3-pyridyl)-propyl]-3-oxa-octanoate is prepared as follows:

To a solution of 4.17 g (13.8 mmol) of 5-hydroxy-8-(3-pyridyl)-1-(2-tetrahydropyranyloxy)-octane in 30 mL dry dimethylformamide is added 17 mL (27.6 mmol) of a 1.61 M solution of potassium t-butoxide in tetrahydrofuran and the resulting red solution is stirred for 0.5 hour. Then the mixture is cooled to 10° C. and 4.9 g (30.4 mmol) of sodium bromoacetate is added followed by 40 mL dry dimethylformamide, and the reaction mixture stirred at room temperature for 18 hours. The reaction mixture is diluted with ether and water. The ether layer is separated and the aqueous phase is adjusted to pH=6.5 using 1N aqueous hydrochloric acid. The resulting solution is extracted thrice with ethyl acetate. The aqueous phase is again adjusted to pH=6.5 and extracted again. The combined organic phase is washed with brine, dried, filtered, and concentrated to give 8-hydroxy-4-[3-(3-pyridyl)propyl]-3-oxa-octanoic acid.

The acid obtained above is dissolved in 50 mL methanol and 1 mL thionyl chloride is added dropwise. The reaction is stirred at room temperature for 18 hours and then concentrated to remove methanol. The residue is taken up in 10 mL water and the pH of the solution is adjusted to 7.0 using 1N aqueous sodium hydroxide. The resulting mixture is extracted thrice with ethyl acetate and the organic phase is washed with brine, dried, filtered and evaporated to give methyl 8-hydroxy-4-[3-(3-pyridyl)propyl]-3-oxa-octanoate. The alcohol is then converted to the final product according to methodology described in Example 37.

EXAMPLE 39 a) A mixture of 0.07 g (0.14 mmol) ethyl 8-(p-chlorophenylsulfonamido)-4-[3-(3-pyridyl)propyl]-3-thiaoctanoate, 1 mL dioxane and 0.3 mL of 1N aqueous sodium hydroxide is stirred for 18 hours at room temperature. The solvent is evaporated and the residue taken up in 0.5 mL water and 0.3 mL in hydrochloric acid. The precipitated product is extracted thrice with methylene chloride. The combined organic extracts are dried, filtered and evaporated to give 65 mg of an oil which is crystallized from ether to obtain 8-(p-chlorophenylsulfonamido)-4-[3-(3-pyridyl)propyl]-3-thiaoctanoic acid, m.p. 78–80°.

b) Similarly prepared is 8-(p-chlorophenylsulfonamido)- 4-[3-(3-pyridyl)propyl]-3-oxaoctanoic acid, m.p. 101–104°.

EXAMPLE 40

To a solution of 0.32 g (0.57 mmol) of t-butyl 8-(p-chlorophenylsulfonamido)-4-(3-iodopropyl)octanoate in 3 mL dry dimethylformamide is added 0.116 g (1.7 mmol) imidazole and the mixture is then refluxed with ethyl acetate and washed with water and brine. The organic layer is dried, filtered, concentrated and then subjected to chromatography using ethyl acetate as eluent to yield t-butyl 8-(p-chloro- phenylsulfonamido)-4-[3-(1-imidazolyl)propyl]octanoate; IR (neat): 1718, 1337, 1164 cm$^{-1}$; NMR (CDCl$_3$): delta 7.5 (br,1H), 7.1 (s,1H), 6.9 (s,1H), 4.2 (t,2H).

The starting material is prepared as follows:

A mixture of 2.0 g (12.8 mmol) ethyl 2-oxocyclopentanecarboxylate, 5.71 g (25.6 mmol) 1-(tetrahydropyranyl- oxy)-3-bromopropane, 7.08 g (57.2 mmol) powdered potassium carbonate and 60 mL acetone is heated to 60° C. under nitrogen with stirring for 8 hours. The reaction mixture is cooled to room temperature, filtered and evaporated to give a yellow orange liquid which is purified by flash chromatograhy using 1:9 ethyl acetate, hexane to yield 2-[3-(tetrahydropyranyloxy)propyl]-2-carbethoxycyclopentanone; IR (neat): 1750 cm$^{-1}$ 1724 cm$^{-1}$.

A mixture of 0.5 g (1.67 mmol) 2-[3-(tetrahydropyranyloxy)propyl]-2-carbethoxycyclopentanone and 5 mL ethanol is saturated with ammonia gas at 5° C. in a thick-wall tube. The tube is sealed and heated to 80° C. for 17 hours. The reaction mixture is cooled and then subjected to evaporation. The resulting oil is chromatographed using 4:1 ethylacetate, hexane+1% ammonia to yield 5-carbethoxy-5-[3-(tetrahydropyranloxy)propyl]valeramide; IR (neat: 3413, 3349, 1727, 1668 cm$^{-1}$.

A solution of 1.0 g (3.17 mmol) of 5-carbethoxy-5-[3-(tetrahydropyranyloxy)propyl]-valeramide in 5 mL tetrahydrofuran is added dropwise to a suspension of 0.481 g (12.68 mmol) lithium aluminum hydride in 20 mL dry tetrahydrofuran. The reaction is refluxed for 2½ hours, cooled in an ice-bath and quenched by the addition of 0.5 mL water, 0.5 mL 15% sodium hydroxide followed by 1.5 mL water. The mixture is stirred for 15 minutes and filtered, washed and then subjected to evaporation to give 6-amino-2-[3-(tetrahydropyranyloxy)-propyl]hexan-1-ol.

Treatment of the above amine with p-chlorophenylsulfonyl chloride in the presence of triethylamine at room temperature overnight in methylene chloride/tetrahydrofuran yields, after purification by chromatography using 1:1 ethylacetate and hexane, 6-(p-chlorophenylsulfonamido)-2-[3-(tetrahydropyranyloxy)-propyl]hexan-1-ol; IR (neat): 3679, 3617, 1336, 1164 cm$^{-1}$.

Treatment of the above alcohol with methanesulfonyl chloride and triethylamine in methylene chloride at room temperature yields 6-(p-chlorophenylsulfonamido)-2-[3(tetrahydropyranyloxy)propyl]-1-(methanesulfonyloxy)-hexane, NMR (CDCl$_3$): delta 3.0 (s,3H), 4.0 (d,2H), 5.4 (t,1H).

To 1.17 g of the above mesylate are added 20 mL acetone, 3.37 g (22.5 mmol) sodium iodide and six drops of pyridine, and the mixture is refluxed for 5 hours. The mixture is cooled, taken up in ether and washed with 10% sodium thiosulfate solution, water and brine. The organic layer is dried, filtered and concentrated to give an amber oil which is chromatographed using 1:4 EtOAc, hexane to yield 6-(p-chlorophenylsulfonamido)-2-[3-(tetrahydropyranyloxy)-propyl]-1-iodo-hexane; NMR (CDCl$_3$): delta 3.3 (d,2H).

To a solution of 0.11 mL cyclohexyl-isopropylamine (0.68 mmol) in 1 mL dry tetrahydrofuran at 0° C. is added dropwise 0.23 mL (0.57 mmol) of a 2.5 M solution of n-butyllithium in hexane. The mixture is allowed to stir for 15 minutes at 0° C. The reaction mixture is then cooled to −78° C. and 0.077 mL (0.57 mmol) t-butyl acetate is added and the mixture is stirred at −78° C. for 0.5 hour. Then a solution of 0.12 g (0.22 mmol) of 6-(p-chlorophenylsulfonamido)-2-[3-(tetrahydropyranyloxy)propyl]-1-iodohexane in 0.5 mL hexamethylphosphoramide is added followed by 1 ml dry tetrahydrofuran. The reaction temperature is raised to −23° C. and allowed to warm to 0° C. over a period of 1 hour. The reaction is then quenched by the addition of 5 mL saturated aqueous ammonium chloride solution and extracted with ether. The organic layer is washed with water (3×25 mL) and brine, dried, filtered, and concentrated to give a yellow oil which is chromatographed using 3:7 ethyl acetate, hexane to yield t-butyl 8-(p-chlorophenylsulfonamido)-4-[3-(tetrahydropyranyloxy)propyl]-octanoate; NMR (CDCl$_3$): delta 2.2 (t,2H), 1.6 (s,9H); IR (neat): 1721 cm$^{-1}$.

To a solution of 0.453 g of t-butyl 8-(p-chlorophenylsulfonamido)-4-[3-(tetrahydropyranyloxy)propyl]octanoate in 7 mL tetrahydrofuran is added 5 mL of 1N aqueous hydrochloric acid and the solution is allowed to stir for 18 hours. The reaction mixture is diluted with water and extracted with ethyl acetate to give a yellow oil which is chromatographed on silica gel using ethyl acetate/hexane (1:4) as eluent to yield t-butyl 8-(p-chlorophenylsulfonamido-4-(3-hydroxypropyl)octanoate; NMR (CDCl₃): delta 3.65 (m,2H), 3.0 (q,2H), 2.2 (t,2H).

Analogous to procedure in a previous step above, t-butyl 8-(p-chlorophenylsulfonamido-4-[3-hydroxypropyl]-octanoate is first treated with methanesulfonyl chloride and then with sodium iodide to yield, after purification by chromatography using 1:4 ethyl acetate, hexane as eluent, t-butyl 8-(p-chlorophenylsulfonamido)-4-(3-iodopropyl)-octanoate; IR (CH₂Cl₂): 1722, 1164 cm⁻¹; NMR (CDCl₃): delta 3.2 (t,2H), 3.0 (q,2H), 2.2 (t,2H).

EXAMPLE 41

(a) To a solution of 0.17 g (0.34 mmol) t-butyl 8-(p-chlorophenylsulfonamido)-4-[3-(1-imidazolyl)propyl]octanoate in 5 mL methylene chloride is added 1 mL trifluoroacetic acid and the solution is stirred at room temperature for 1.5 hours. The solvent is evaporated and the residue taken up in 5 mL water. The pH of the solution is adjusted to 6.5 using 1N aqueous sodium hydroxide. Then the aqueous solution is extracted twice with ethyl acetate. The combined organic layer is washed with water and brine, dried, filtered and concentrated to give a pale yellow oil. The product is triturated five times with 2 mL ether and finally dried to yield 8-(p-chlorophenylsulfonamido)-4-[3-(1-imidazolyl)propyl]octanoic acid, m.p. 136–138° C.

Similarly prepared according to Example 40 and the above are:
(b) 8-(beta-naphthylsulfonamido)-4-[3-(1-imidazolyl-propyl]-octanoic acid;
(c) 8-(p-trifluoromethylphenylsulfonamido)-4-[3-(1-imidazolyl)-propyl]-octanoic acid;
(d) 8-(phenylsulfonamido)-4-[3-(1-imidazolyl)-propyl]-octanoic acid;
(e) 8-(3,4-dichlorophenylsulfonamido)-4-[3-(1-imidazolyl)-propyl]-octanoic acid;
(f) 8-(p-methoxyphenylsulfonamido)-4-[3-(1-imidazolyl)-propyl]-octanoic acid;
(g) 8-(p-methylphenylsulfonamido)-4-[3-(1-imidazolyl)-propyl]-octanoic acid;
(h) 8-(p-carboxyphenylsulfonamido)-4-[3-(1-imidazolyl)-propyl]-octanoic acid;
(i) 8-(p-fluorophenylsulfonamido)-4-[3-(1-imidazolyl)-propyl]-octanoic acid.

EXAMPLE 42

According to procedure described in the previous examples, ethyl 7-amino-3-[3-(3-pyridyl)propyl]heptanoate is treated with p-chlorophenylsulfonyl chloride in the presence of triethylamine to yield, after purification by chromatography using 1:1 ethyl acetate and hexane, ethyl 7-(p-chlorophenylsulfonamido)-3-[3-(3-pyridyl)propyl]-heptanoate, NMR (CDCl₃): delta 7.8 (d,2H), 7.5 (d,2H), 6.0 (t,1H), 2.9 (q, 2H).

The starting material is prepared as follows:

A solution of 1.62 mL (22.73 mmol) of dimethylsulfoxide in 60 mL dry methylene chloride is cooled to −78° C. and 1.44 mL (16.53 mmol) oxalyl chloride is added dropwise. The mixture is stirred 0.5 hour at −78° C. and a solution of 1.0 g (3.31 mmol) of 1-(3-pyridyl)-4-hydroxy-8-(2-tetrahydropyranyloxy)octane in 15 mL dry methylene chloride is added and the mixture is stirred for 10 minutes at -78° C. The mixture is warmed to −60° C. and maintained for 15 minutes at that temperature. The reaction is quenched by the addition of 6.9 mL triethylamine. The cold bath is removed and the reaction allowed to warm to room temperature. The reaction mixture is extracted with 150 mL methylene chloride and washed with saturated sodium bicarbonate solution. The organic phase is dried, filtered, concentrated and chromatographed using 3:2 ethyl acetate, hexane to yield 1-(3-pyridyl)-4-oxo-8-(2-tetrahydropyranyloxy)octane; NMR (CDCl₃): delta 2.6 (t,2H), 2.4 (t,4H).

To a solution of 5.74 mL 93.33 mmol) of 0.58 M potassium hexamethyldisilazane in toluene is added dropwise 0.66 mL triethyl phosphonoacetate resulting in a yellow gelatinous mixture. This reaction mixture is stirred at room temperature for 25 minutes, a solution of 0.5 g (1.66 mmol) 1-(3-pyridyl)-4-oxo-8-(2-tetrahydropyranyloxy)-octane in 3 mL toluene is added and the mixture is refluxed for 15 hours. The reaction mixture is cooled to room temperature, quenched with 5 mL saturated aqueous ammonium chloride solution and extracted with ethyl acetate twice. The combined organic phase is washed with water and brine, dried, filtered and concentrated to give a brown oil which is purified by chromatography using 1:1 ethyl acetate, hexane to yield ethyl 3-[3-(3-pyridyl)propyl]-7-(2-tetrahydropyranyloxy)-hept-2-enoate as a mixture of cis and trans isomers; NMR (CDCl₃): delta 5.7 (s,1H), 4.2 (q,2H), 1.3 (t,3H).

A solution of 1.385 g of ethyl 3-[3-(3-pyridyl)-propyl]-7-(2-tetrahydropyranyloxy)-hept-2-enoate in 30 mL ethyl acetate is hydrogenated in a Parr apparatus at 3 atmospheres pressure and room temperature in the presence of 5% Pd/C catalyst for 13 hours to yield ethyl 3-[3-(3-pyridyl)-propyl]-7-(2-tetrahydropyranyloxy)-heptanoate; NMR (CDCl₃): delta 2.2 (ddd,2H).

Treatment with 12 ml 1N aqueous hydrochloric acid in tetrahydrofuran at room temperature for 3 hours yields ethyl 7-hydroxy-3-[3-(3-pyridyl)propyl]heptanoate; IR (neat): 3616, 1725 cm⁻¹. The product is purified by chromatography using ethyl acetate as eluent.

Ethyl 7-hydroxy-3-[3-(3-pyridyl)propyl]heptanoate is converted via azide, using procedures analogous to those in Example 22, to ethyl 7-amino-3-[3-(3-pyridyl)-propyl]-heptanoate; NMR (CDCl₃): delta 3.3 (q,2H).

EXAMPLE 43

Hydrolysis of ethyl 7-(p-chlorophenylsulfonamido)-3[3-(3-pyridyl)propyl]heptanoate in 3 mL methanol with 5.2 mL (5.2 mmol) of 1N sodium hydroxide according to procedure described in the previous examples yields 7-(p-chlorophenylsulfonamido)-3-[3-(3-pyridyl)propyl]heptanoic acid, m.p. 95–97°.

EXAMPLE 44

A mixture of 0.528 g 8-(p-chlorophenylsulfonamido)-4[3-(3-pyridyl)propyl]octanenitrile and 1.04 mL tributyltin azide in 5 mL tetrahydrofuran is heated at 120° C. for 64 hours. The solvent is evaporated and subjected to flash chromatography over silica gel using methylene chloride/hexane/methanol/acetic acid (45:25:5:0.8) as eluent to give an oil which is purified again by preparative thin layer chromatography using methylene chloride, methanol, hexane, acetic acid (45:5:25:0.8) as eluent to yield an oil which is triturated with ether and hexane to give 5-{7-(p-chlorophenylsulfonamido)-3-[3-(3-pyridyl)-propyl]-heptyl}-1H-tetrazole hemihydrate, m.p. 56–81°.

The starting material is prepared as follows:

A mixture of 1.44 g of 8-(p-chlorophenylsulfonamido-4-[3-(3-pyridyl)-propyl]-octanamide and 0.52 mL pyridine in 5.8 mL dioxane is cooled to 0° C. and 0.51 mL trifluoroacetic anhydride is added over a period of 1 hour. The mixture is then stirred at room temperature for 3 hours. The reaction is quenched by the addition of saturated aqueous sodium bicarbonate solution and extracted with methylene chloride (2×20 mL). The combined organic extracts are dried, filtered and evaporated to give 8-(p-chlorophenyl- sulfonamido)-4-[3-(3-pyridyl)propyl]octanenitrile.

EXAMPLE 45

(a) To a solution of 0.144 g (0.44 mmol) methyl 8-amino-4-[m-(3-pyridyl)phenyl]octanoate in 2 mL methylene chloride is added a catalytic amount (0.02 g) 4-dimethylaminopyridine followed by 0.08 mL (0.57 mmol) triethylamine and 0.098 g (0.5 mmol) p-fluorophenylsulfonyl chloride. The mixture is stirred at room temperature for 18 hours, diluted with methylene chloride, washed with saturated sodium bicarbonate solution, water and brine, dried, filtered and evaporated to give a greenish oil which is purified by chromatography using 3:2 ethyl acetate and hexane as eluent to obtain methyl 8-(p-fluorophenylsulfonamido-4-[m-(3-pyridyl)-phenyl]octanoate as an oil; NMR (CDCl$_3$): delta 3.63 (s,3H), 2.9 (q,2H), 8.95 (d,1H), 8.67 (dd,2H).

The starting material is prepared as follows:

A solution of 2.52 g (14 mmol) of ethyl m-hydroxyphenylacetate in 36 mL methylene chloride is cooled to 0° C. and 5.0 g (14 mmol) N-phenyltrifluoromethanesulfonimide (N-phenyltriflimide) followed by 2.1 mL (15 mmol) triethylamine are added. The solution is allowed to stir at room temperature for 16 hours, diluted with methylene chloride, and then washed with 1N sodium hydroxide and half saturated potassium carbonate solution. The organic layer is dried over anhydrous potassium carbonate, filtered and evaporated to yield ethyl m-(trifluoromethanesulfonyloxy)phenylacetate, as an oil; IR (CH$_2$Cl$_2$) 1734, 1421, 1220, 1141 cm$^{-1}$. 3-(Trifluoromethanesulfonyloxy)pyridine is similarly prepared from 3-hydroxypyridine; IR (CH$_2$Cl$_2$): 1428, 1219, 1139 cm$^{-1}$.

To a solution of 2.04 g (6.5 mmol) of ethyl m-(trifluoromethanesulfonyloxy)phenylacetate in 33 mL dioxane is added 1.33 mL (6.5 mmol) hexamethylditin followed by 1.49 g (6.6 mmol) 3-(trifluoromethanesulfonyloxy)-pyridine, 0.827 g (19.5 mmol) lithium chloride and 0.15 g (0.13 mmol) tetrakis-(triphenylphosphine) palladium(0). The mixture is then heated at 90° C. for 62 hours, diluted with ether and washed with 10% ammonium hydroxide followed by water and brine. The organic layer is dried, filtered, evaporated and the residue is purified by flash chromatography using 1:1 ether and hexane as eluent to give ethyl m-(3-pyridyl)phenylacetate; IR (CH$_2$Cl$_2$) 1731 cm$^{-1}$.

To a solution of 0.363 g (1.5 mmol) of ethyl m-(3-pyridyl)phenylacetate in 5.4 mL dry dimethylformamide at 5° C. is added 1.56 mL of a 1M solution of sodium hexamethyldisilazide in tetrahydrofuran. The organic layer is evaporated to dryness and resulting orange colored solution is stirred for 10 minutes and 0.54 mL (4.7 mmol) 1-bromo-4-chlorobutane is added rapidly. The reaction is stirred at 5° C. for 2 hours and then poured into water and extracted thrice with ether. The organic layer is evaporated to dryness and the resulting oil is purified by flash chromatography using 1:1 ether and hexane to obtain ethyl 6-chloro-2-[m-(3-pyridyl)phenyl]hexanoate; IR (CH$_2$Cl$_2$): 1728, 1278, 1184, 1165, 1023 cm$^{-1}$.

To a solution of 0.54 g (1.6 mmol) ethyl 6-chloro-2[m-(3-pyridyl)phenyl]hexanoate in 10 mL methylene chloride at −78° C. is added slowly 2.2 mL (3.4 mmol) of a 1.5 M solution of diisobutylaluminum hydride in hexanes. The reaction is stirred at -78° C. for 5 minutes and 1.6 mL methanol is added followed by 50 mL ether. The mixture is warmed to 0° C. and 1.6 mL brine and 1.11 g finely powdered sodium sulfate are added. The mixture is stirred and then filtered. The filter cake is washed with methylene chloride and combined organic layer is evaporated to give 6-chloro-2-[m-(3-pyridyl)-phenyl]hexanal as an oil; IR (CH$_2$Cl$_2$): 1724, 1682 cm$^{-1}$.

To a solution of 0.55 g (1.9 mmol) of 6-chloro-2-[m-(3-pyridyl)phenyl]hexanal in 10 mL methylene chloride is added 0.66 g (1.9 mmol) of methyl triphenylphosphoranilideneacetate and the mixture is stirred at room temperature for 16 hours. The solvent is evaporated and the residue purified by flash chromatography using 3:7 ethyl acetate and hexane to obtain methyl 8-chloro-4-[m-(3-pyridyl)phenyl]oct-2-enoate; IR (CH$_2$Cl$_2$) 1718, 1280, 896 cm$^{-1}$.

To a mixture of 0.422 g (1.2 mmol) methyl 8-chloro-4[m-(3-pyridyl)phenyl]oct-2-enoate, 0.097 g (0.41 mmol) cobalt (II) chloride and 8 mL methanol at 0° C. is added slowly 0.105 g (2.8 mmol) of sodium borohydride. The resulting black suspension is stirred at 0° C. for 30 minutes and then filtered through activated magnesium silicate (Florisil) and the filter cake is washed several times with methanol. The solvent is evaporated to obtain methyl 8-chloro-4-[m-(3-pyridyl)-phenyl]octanoate; IR (CH$_2$Cl$_2$): 1732 cm$^{-1}$.

Treatment of methyl 8-chloro-4-[m-(3-pyridyl)-phenyl]-octanoate with sodium azide and sodium iodide according to previous examples yields methyl 8-azido-4-[m-(3-pyridyl)phenyl]-octanoate as an oil; IR (CH$_2$Cl$_2$) 2099, 1732 cm$^{-1}$.

Reduction of the azide with triphenylphosphine in tetrahydrofuran according to previous examples yields methyl 8-amino-4-[m-(3-pyridyl)phenyl]octanoate; IR (CH$_2$Cl$_2$): 1732 cm$^{-1}$.

(b) Similarly prepared is methyl 8-(p-chlorophenylsulfonamido)-4-[m-(3-pyridyl)phenyl]octanoate.

(c) Similarly prepared is methyl 8-(p-chlorophenylsulfonamido)-4-[p-(3-pyridyl)phenyl]octanoate.

(d) Similarly prepared is methyl 8-(p-fluorophenylsulfonamido)-4-[p-(3-pyridyl)phenyl]octanoate.

EXAMPLE 46

(a) Similarly to procedure described in previous examples methyl 8-(p-fluorophenylsulfonamido)-4-[m-(3-pyridyl)phenyl] octanoate is hydrolyzed to 8-(p-fluorophenylsulfonamido-4-[m-(3-pyridyl)phenyl]octanoic acid, m.p. 61–63° C.

(b) Similarly prepared is 8-(p-chlorophenylsulfonamido)-4-[m-(3-pyridyl)phenyl]octanoic acid, m.p. 157–158° C.

(c) Similarly prepared is 8-(p-chlorophenylsulfonamido)-4-[p-(3-pyridyl)phenyl]octanoic acid; NMR (CDCl$_3$) delta 7.76 (d, 2H), 7.2 (d, 2H), 2.2 (t, 2H), 2.6 (m, 1H).

(d) Similarly prepared is 8-(p-fluorophenylsulfonamido)-4-[p-(3-pyridyl)phenyl]-octanoic acid.

EXAMPLE 47

To a solution of 2200 g of crude ethyl 8-amino-4-[3-(3-pyridyl)-propyl]-octanoate in 28.8 L of dichloromethane is added 1377 g of triethylamine. The solution is cooled to 0° and a solution of 1435 g of p-chlorophenylsulfonyl chloride in 14.3 L of dichloromethane is added over a period of 45 minutes maintaining the temperature below 5°. The reaction is allowed to slowly warm up to room temperature overnight. The reaction mixture is washed 3 times with 15 L of sodium bicarbonate and then with water, dried over sodium sulfate and evaporated to dryness to yield ethyl 8-(p-chlorophenylsulfonamido)-4-[3-(3-pyridyl)-propyl]-octanoate as an oil.

The starting material is prepared as follows:

Thionyl chloride (1.125 L, 1.835 kg, 15.42 mol) is cooled to 0° C., and dimethylformamide (1.199 L, 1.132 kg, 15.50 mol) is added dropwise over a period of 2 hours keeping the temperature below 10° C. After the addition is complete the reaction is allowed to come to room temperature over 2 hours. To this is then added 5-carbomethoxy-oct-7-enoic acid amide (see example 22c, 2.671 kg, 13.42 mol) neat over a period of 3 hours. The reaction is allowed to stir at room temperature for 18 hours and is combined with material from a similar run and then diluted with ethyl ether (35 L). The solution is cooled to 0° C. and is admixed with 8 kg of ice and 12 L of water. The mixture is stirred for 30 minutes and is then basified with ammonium hydroxide (12 L, 2.5 M). The layers are separated and the organic phase is washed with water (12 L) and brine (12 L) and dried over anhydrous sodium sulfate (7.5 kg). This is then filtered and evaporated to yield a crude oil which is redissolved in ethyl ether (24 L) and this solution is stirred over 7 kg of silica gel for several hours. After filtration and evaporation there is obtained partially purified material which is then distilled to obtain 5-carbomethoxy-oct-7-enenitrile, b.p. 118–120° /0.15 mm Hg.

Methanol (4136 mL) is added dropwise over about 3 hours to a mixture of 2054 g of 5-carbomethoxy-oct-7-enenitrile, 1286 g of sodium borohydride and 20.5 L of 1,2-dimethoxyethane heated at 75°. The reaction mixture is heated at 95° for 3½ hours, stirred at room temperature overnight, and cooled to 8° C. in an ice bath. Water (21.0 L) is added slowly, the mixture is again stirred for 1½ hours at room temperature, and then extracted with ethyl acetate (2×20 L). The combined extract is washed with brine, dried over sodium sulfate and evaporated to dryness at 65–70°/3 mm Hg. The residue is distilled to yield 6-hydroxy-5-(2-propenyl)-hexanenitrile, b.p. 113–116°/0.8 mm Hg.

To a solution of 2679 g of 6-hydroxy-5-(2-propenyl)-hexanenitrile in 25 L of methylene chloride is added 2681 mL of triethylamine. The mixture is cooled to −10° in an ice salt bath and a solution of 2103 g of methanesulfonyl chloride in 2 L of methylene chloride is added dropwise over 3 hours keeping the temperature at −5°. After addition is complete, the mixture is stirred for 3 hours in an ice salt bath and then overnight at 10°. The mixture is washed with water, saturated sodium bicarbonate solution, water and then brine, dried over sodium sulfate, evaporated to dryness, and dried at 45°/3 mm Hg to yield 6-methanesulfonyloxy-5-(2-propenyl)-hexanenitrile.

A solution of 5410 g of diethyl malonate in 2000 ml of tetrahydrofuran is added to a mixture of 1351 g of 60% sodium hydride in mineral oil in 36 L of tetrahydrofuran over a period of 4 hours, keeping the temperature below 26°, and the mixture is stirred for ½ hour. A solution of 3705 g of 6-methanesulfonyloxy-5-(2-propenyl)-hexanenitrile in 200 ml tetrahydrofuran is added rapidly and the mixture is heated under reflux for 24 hours and allowed to cool overnight. The mixture is neutralized to pH 7 with glacial acetic acid (about 1 L) and evaporated to dryness. A solution of the residue in 30 L of ether is washed consecutively with water, saturated sodium bicarbonate solution, water and brine, and evaporated to dryness. The mineral oil is separated in a separatory funnel and the remaining product is washed three times with heptane, concentrated at 80°/0.01 mm Hg, and distilled at 150° to remove diethyl malonate and obtain crude diethyl [5-cyano-2-(2-propenyl)-pentyl]-malonate.

The above malonate ester (2169 g) is added to a solution of 622.9 g of lithium chloride in a mixture of 10,845 mL dimethylformamide and 1085 mL of water. The mixture is heated at reflux for 27 hours and allowed to cool to room temperature overnight. The solution is poured into 22 L of ice/water, extracted with diethyl ether, the extract is then washed with saturated sodium bicarbonate, water and brine, dried over sodium sulfate and evaporated to dryness. The residue is distilled to yield ethyl 4-(3-cyanopropyl)-6-heptenoate, b.p. 136–138/0.2 mm Hg.

A mixture of 1300 g of ethyl 4-(3-cyanopropyl)-6-heptenoate, 6397 ml of acetonitrile, 3190 mL of triethylamine and 920.9 g of 3-bromopyridine is degassed and then heated to reflux. Palladium II acetate catalyst (13 g) and 36.42 g of tri-o-tolylphosphine are added and the mixture is heated under reflux overnight. Additional catalyst (13 g) is added and the mixture is again heated under reflux for 7 hours. Further catalyst (6.5 g) is again added and the reaction is again heated under reflux overnight. The reaction mixture is cooled, diluted with 6 L of methylene chloride, and evaporated to dryness. The residue is partitioned between ether and water. The ether layer is separated and the aqueous layer is extracted two more times with ether. The combined ether extracts are extracted with 2×8 L of 1 N hydrochloric acid. The acid extract is cooled and made basic with 1200 ml of conc. ammonium hydroxide to pH 10, and extracted with ether (3×8 L). The ether extract is dried over sodium sulfate and evaporated to dryness to yield ethyl 4-(3-cyanopropyl)-7-(3-pyridyl)-6-heptenoate.

A solution of 125 g of ethyl 4-(3-cyanopropyl)-7-(3-pyridyl)-6-heptenoate in 825 ml of 9.53% ethanolic ammonia is added to a slurry of 62.5 g of 5% rhodium on carbon (50% water wet) in 300 ml of 9.53% ethanolic ammonia. The mixture is hydrogenated at about 3 atmospheres pressure (50 psi) until theoretical uptake of hydrogen (4 moles) for saturation of the nitrile and double bond is obtained (about 12 hours). The catalyst is then filtered off, washed with methylene chloride and ethanol, and the filtrate is evaporated to dryness to yield a residue which is redissolved in toluene. Evaporation to dryness yields ethyl 8-amino-4-[3-(3-pyridyl)-propyl]-octanoate.

EXAMPLE 48

A solution of 130.15 g of sodium methoxide in 2.4 L methanol is added at room temperature to a solution of 5469 g of ethyl 8-(p-chlorophenylsulfonamido)-4-[3-(3-pyridyl)-propyl]-octanoate in 52.3 L of methanol. The mixture is stirred for 40 hours under nitrogen. Glacial acetic acid (145.5 g) is added and the reaction mixture is evaporated to dryness at 60° and 3 mm Hg. The residue is dissolved in 40 L of ethyl acetate, the solution is washed with dilute sodium bicarbonate solution and then with 5% sodium bisulfite, dried over sodium sulfate, treated with charcoal and evaporated to dryness to yield crude methyl 8-(p-chloro-phenylsulfonamido)-4-[3-(3-pyridyl)-propyl]-octanoate.

EXAMPLE 49

A mixture of 3046 g of methyl 8-(p-chlorophenylsulfonamido)-4-[3-(3-pyridyl)-propyl]octanoate, 10 L of acetonitrile and 6701 mL of 2M lithium hydroxide is stirred at room temperature overnight, and then diluted with 20 L of water. Acetic acid (1 L) is added to adjust pH to 5.5 and additional water (12 L) is added. The precipitated product is collected and resuspended in 50 L of water. The suspension is stirred, the precipitate is collected, washed with water and dried at 60°/3 mm Hg for 48 hours. The product is recrystallized twice from ethyl acetate and once from acetonitrile to yield 8-(p-chlorophenylsulfonamido)4-[3-(3-pyridyl)-propyl]-octanoic acid, m.p. 116.5–118°.

EXAMPLE 50 a) Ethyl 8-amino-5-(3-pyridyloxy)-octanoate is condensed with p-chlorophenylsulfonyl chloride according to methodology previously described to yield ethyl 8-(p-chlorophenylsulfonamido)-5-(3-pyridyloxy)-octanoate which is purified by chromatography on silica gel using 7:3 ethyl acetate, hexane as eluent; 1H NMR (CDCl$_3$): delta 8.26 (br,1H), 8.20 (br,4H), 5.23 (t,1H), 4.28 (m,1H), 4.08 (q,2H).

The starting material is prepared as follows:

To a solution of potassium hexamethyldisilazide (66 mL, 60 mmol) in dry tetrahydrofuran (140 mL) at −70° C. is added slowly 5-oxohexanoic acid (36 mL, 30 mmol). The resulting yellow suspension is stirred at −70° C. for 1 hour and bromoacetonitrile (2.2 mL, 32 mmol) is added slowly. The reaction mixture is stirred at −70° C. for 1 hour and then at room temperature for 0.5 hour. The reaction is quenched by addition of 1N aqueous hydrochloric acid (100 mL). The aqueous layer is extracted twice with ether. Combined organic layer is dried, filtered and evaporated to obtain a dark oil which is purified by silica gel chromatography using 9:1 ether:-hexane with 1% acetic acid as eluent to give 7-cyano-5-oxoheptanoic acid as an oil.

The above acid is dissolved in 20 mL methylene chloride at 0° C. and an excess of a solution of diazomethane in ether is added and stirred for 0.25 hour. Excess diazomethane is destroyed by adding a few drops of acetic acid and the organic layer is washed with saturated aqueous sodium bicarbonate solution. The organic layer is dried, filtered and subjected to evaporation to yield methyl 7-cyano-5-oxoheptanoate as an oil; 1H NMR (CDCl$_3$) delta 3.63 (s,3H), 2.78 (t,2H), 2.55 (m,4H), 2.33 (t,2H), 1.91 (q,2H).

To a solution of methyl 7-cyano-5-oxoheptanoate (1.32 g, 7.2 mmol) in 30 mL ethanol at 0° C. is added sodium borohydride (0.28 g, 7.3 mmol) in small portions. The solution is allowed to warm to room temperature and stirred for 1 hour. The reaction is quenched using saturated ammonium chloride and extracted with ethyl acetate. The combined organic extract is washed with brine, dried, filtered and subjected to rotary evaporation to get an oil which is identified as ethyl 7-cyano-5-hydroxyheptanoate; 1H NMR (CDCl$_3$): delta 4.1 (q,2H), 3.67 (m,1H), 2.49 (t,2H), 2.33 (t,2H), 1.4–1.9 (m,6H), 1.22 (t,3H)

To a mixture of triphenylphosphine (2.42 g, 9.2 mmol) and 3-hydroxypyridine (0.7 g, 7.3 mmol) in methylene chloride (20 mL) is added the ethyl 7-cyano-5-hydroxyheptanoate obtained above. The reaction mixture is stirred for 5 minutes and then diethyl azodicarboxylate (1.0 mL, 6.3 mmol) is added dropwise. The reaction mixture is stirred overnight and the solvent is evaporated. The residue is chromatographed on silica gel using ether as eluent to obtain an amber oil. The oil is dissolved in 10 mL ether, cooled to 0° C. and the precipitated triphenylphosphine oxide is filtered off. The filtrate is evaporated to give crude ethyl 7-cyano-5-(3-pyridyloxy)-heptanoate, IR (CH$_2$Cl$_2$): 2239, 1729, 1576, 1229, 1167, 1120 cm$^{-1}$.

A solution of crude ethyl 7-cyano-5-[3-pyridyloxy)-heptanoate (1.74 g) in 50 mL of methanol saturated with ammonia is subjected to hydrogenation for 5 hours at 3 atmospheres pressure of hydrogen using Raney Nickel (1.0 ml aqueous suspension) as the catalyst. The catalyst is filtered off and washed with methanol. The filtrate is evaporated and the residue filtered through a plug of silica gel using ether as eluent to remove remaining triphenylphosphine oxide. The compound is eluted from the silica gel using methanol:triethylamine (95:5). The solvent is evaporated to yield ethyl 8-amino-5-(3-pyridyloxy)-octanoate; 1H NMR (CDCl$_3$): delta 8.28 (br,1H), 8.19 (br,1H), 4.39 (m,1H), 4.08 (q,2H).

b) Ethyl 8-(p-chlorophenylsulfonamido)-5-(3-pyridyloxy)-octanoate is hydrolyzed with 1N aqueous sodium hydroxide and dioxane and the product is purified using preparative thin layer chromatography on silica gel using 4:1 ethyl acetate/hexane/1% acetic acid as eluent to give 8-(p-chlorophenylsulfonamido)-5-(3-pyridyloxy)-octanoic acid; 1H NMR (CDCl$_3$): delta 8.16 (br s,1H), 8.08 (d,1H), 4.39 (m,1H), 2.86 (t,2H).

EXAMPLE 51

A solution of 2.9 g (5 mmol) of ethyl 8-[N-(p-chlorophenylsulfonyl)-N-(t-butoxycarbonyl)amino]-4-[2-(3-pyridyl- oxy)-ethyl]octanoate in 30 ml trifluoroacetic acid is stirred at room temperature. After 18 hours the reaction mixture is evaporated to dryness. The residue is dissolved in methylene chloride and the solution is washed with saturated NaHCO$_3$ solution, dried and evaporated. The residue is chromatographed on silica gel using 1:1 ethyl acetate/methylene chloride as eluent to yield ethyl 8-(p-chlorophenylsulfonamido)-4-[2-(3-pyridyloxy)ethyl]octanoate.

The starting material is prepared as follows:

4-(4-Hydroxybutyl)-epsilon-caprolactone (see example 28) is, according to methodology described herein, first converted to 4-(4-azidobutyl)-epsilon-caprolactone which is then hydrogenated in ethyl acetate using 5% palladium on carbon catalyst to the amine, which is in turn converted to 4-[4-(p-chlorophenylsulfonamido)-butyl]-epsilon-caprolactone, m.p. 90–93°.

To a solution of 3.60 g (10 mmol) of the lactone in 36.0 ml methylene chloride at 0° C. under an inert atmosphere is added 4.40 g (22 mmol) of iodotrimethylsilane dropwise. After 20 hours at room temperature the reaction is recooled to 0° C. and 2.52 g (55 mmol) ethanol (anhydrous) is added dropwise, over 15 minutes. After 24 hours at room temperature, the reaction mixture is washed with cold 10% Na$_2$SO$_3$ solution, dried and evaporated to yield ethyl 8-(p-chlorophenylsulfonamido)-4-(2-iodoethyl)octanoate.

To a solution of 2.6 g (5 mmol) of ethyl 8-(p-chlorophenylsulfonamido)-4-(2-iodoethyl)octanoate in 30 ml tetrahydrofuran is added 1.63 g (7.5 mmol) di-t-butyl dicarbonate and a catalytic amount of 4-dimethylaminopyridine. After 18 hours at room temperature, the solvent is evaporated. The residue is dissolved in ethyl acetate and the solution is washed with saturated sodium bicarbonate solution and brine, dried and evaporated. The residue is chromatographed on silica gel using 1:40 ethyl ether/methylene chloride as eluent to yield ethyl 8-[N-(p-chlorophenylsulfonyl)-N-(t-butoxycarbonyl)amino]-4-(2-iodoethyl)octanoate.

To a solution of 3.1 g (5 mmol) of ethyl 8-[N-(p-chlorophenylsulfonyl)-N-(t-butoxycarbonyl)amino]-4-(2-iodoethyl)octanoate in 10 ml dimethylformamide at 0° C. under an inert atmosphere is added a solution of 0.62 g (6.5 mmol) 3-hydroxypyridine and 0.73 g potassium-t-butoxide in 20 ml dimethylformamide, dropwise. After 24 hours at room temperature the reaction is evaporated to dryness. The residue is dissolved in ethyl acetate and the solution is washed with cold 5% $Na_2CO_3$ solution and brine, dried and evaporated to yield ethyl 8-[N-(p-chlorophenylsulfonyl)-N-(t-butoxycarbonyl)-amino]-4-[2-(3-pyridyloxy)-ethyl]-octanoate.

EXAMPLE 52

To a solution of 1.3 g (2.7 mmol) of ethyl 8-(p-chlorophenylsulfonamido)-4-[2-(3-pyridyloxy)ethyl]octanoate in 8.1 ml acetonitrile is added 2.7 ml (5.4 mmol) 2 M LiOH solution in water. After 18 hours at room temperature, the reaction mixture is diluted with 9.5 ml water and filtered to remove a small amount of insoluble solid. The filtrate is acidified with 0.36 g (5.94 mmol) acetic acid and stirred in an ice bath. After 2 hours the solid is filtered, washed with water and dried. Recrystallization from acetonitrile gives pure compound of example 31, namely 8-(p-chlorophenyl-sulfonamido)-4-[2-(3-pyridyloxy)ethyl]octanoic acid, m.p. 86–88°; further recrystallization gives m.p. 89–91°. Compound forms potassium salt as hydrate (containing 1.5 moles water).

EXAMPLE 53

Preparation of 1,000 capsules each containing 50 mg of the active ingredient:

Formula

| | |
|---|---|
| 8-(p-Chlorophenylsulfonamido)-4-[3-(3-pyridyl)-propyl]-octanoic acid | 50.0 g |
| Lactose | 167.0 g |
| Modified starch | 80.0 g |
| Magnesium stearate | 3.0 g |

Procedure

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

Analogously, capsules can be prepared containing the other compounds disclosed and exemplified herein, e.g. 8-(p-chlorophenylsulfonamido)-4-[2-(3-pyridyloxy)-ethyl]octanoic acid.

EXAMPLE 54

Preparation of an injectable formulation containing 10 mg of the active ingredient per 5 ml of solution:

Formula

| | |
|---|---|
| Sodium 8-(p-chlorophenylsulfonamido)-4-[3-(3-pyridyl)propyl]-octanoate | 10.0 g |
| Propylparaben | 0.5 g |
| Water for injection q.s. | 5000.0 ml |

The active ingredient and preservative are dissolved in 3500 ml of water for injection and the solution is diluted to 5000 ml. The solution is filtered through a sterile filter and filled into injection vials under sterile conditions, each vial containing 5 ml of the solution.

Analogously, an injectable formulation can be prepared containing the other compounds disclosed and exemplified herein, e.g. 8-(p-chlorophenylsulfonamido)-4-[2-(3-pyridyloxy)-ethyl]octanoic acid.

What is claimed is:

1. A compound of the formula

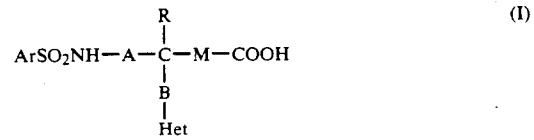

(I)

wherein A represents lower alkylene; B represents oxygen, sulfur, lower alkylene, lower alkylene interrupted by oxygen, sulfur, sulfinyl or sulfonyl, (oxy-, sulfinyl-, sulfonyl- or thio)-lower alkylene, lower alkenylene, phenylene or a direct bond; M represents lower alkylene, lower alkylene interrupted by oxygen, sulfur, sulfinyl or sulfonyl, (oxy-, sulfinyl, sulfonyl- or thio)-lower alkylene, lower alkenylene or a direct bond; or one of A, B and M represents hydrogen unless A, B or M represents lower alkylidenylene in which case R represents the second bond to the adjacent alkylidenylene unsaturated carbon atom; Het represents 3-pyridyl, or 3-pyridyl substituted by lower alkyl; Ar represents carbocyclic aryl; a pharmaceuitically acceptable ester or amide derivative thereof wherein carboxy is esterified in form of a pharmaceutically acceptable ester or carboxy is derivatized in form of a pharmaceutically acceptable amide; the N-oxide thereof; or a pharmaceutically acceptable salt thereof; or a compound of the formula

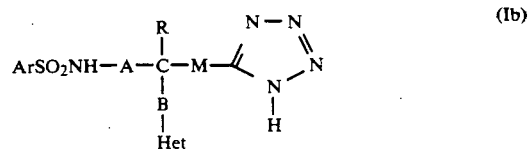

(Ib)

wherein Ar, A, B, M, R and Het have meaning as defined above; the N-oxide of a said compound; or a pharmaceutically acceptable salt thereof.

2. A compound according to claim 1 of the formula

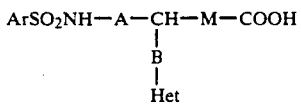

$$\text{ArSO}_2\text{NH}-\text{A}-\underset{\underset{\text{Het}}{|}}{\overset{\overset{\text{B}}{|}}{\text{CH}}}-\text{M}-\text{COOH} \quad \text{(Ia)}$$

wherein A represents lower alkylene; B represents oxygen, sulfur, (oxy-sulfinyl-, sulfonyl- or thio)-lower alkylene, lower alkylene, lower alkenylene, phenylene or a direct bond; M represents lower alkylene, lower alkylene interrupted by oxygen, sulfur sulfinyl or sulfonyl, (oxy-, sulfinyl-, sulfonyl- or thio)-lowr alkylene, lower alkenylene or a direct bond; Het represents 3-pyridyl or 3-pyridyl substituted by lower alkyl; Ar represents carbocyclic aryl; a pharmaceutically acceptable ester or amide derivative thereof; the N-oxide thereof; or a pharmaceutically acceptable salt thereof.

3. A compound according to claim 2 of the formula

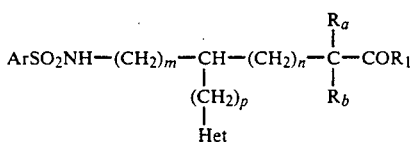

$$\text{ArSO}_2\text{NH}-(\text{CH}_2)_m-\underset{\underset{\underset{\text{Het}}{|}}{(\text{CH}_2)_p}}{|}{\text{CH}}-(\text{CH}_2)_n-\underset{\underset{\text{R}_b}{|}}{\overset{\overset{\text{R}_a}{|}}{\text{C}}}-\text{COR}_1 \quad \text{(II)}$$

wherein Ar represents carbocyclic aryl; Het represents 3-pyridyl or 3-pyridyl substituted by lower alkyl; m represents an integer from 1 to 5 inclusive, n represents zero or an integer from 1 to 4 inclusive; p represents zero or an integer from 1 to 5 inclusive; $\text{COR}_1$ represents carboxy or carboxy derivatized in the form of a pharmaceutically acceptable ester or amide; $R_a$ and $R_b$ independently represent hydrogen or lower alkyl; the N-oxide thereof; or a pharmaceutically acceptable salt thereof.

4. A compound according to claim 3 of formula II wherein $R_a$, $R_b$, Ar and Het have meaning as defined in said claim; m represents the integer 2, 3 or 4; n represents the integer 1, 2 or 3; p represents the integer 1, 2 or 3; $\text{COR}_1$ represents carboxy or carboxy derivatized in the form of a phamaceutically acceptable ester or amide; or a pharmaceutically acceptable salt thereof.

5. A compound according to claim 3 wherein m represents 4, n represents 1 and p represents 3.

6. A compound according to claim 3 wherein m represents 2, n represents 3 and p represents 1.

7. A compound according to claim 3 wherein m represents 3, n represents 2 and p represents 2.

8. A compound according to claim 2 of the formula

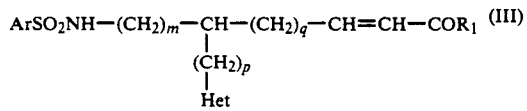

$$\text{ArSO}_2\text{NH}-(\text{CH}_2)_m-\underset{\underset{\underset{\text{Het}}{|}}{(\text{CH}_2)_p}}{|}{\text{CH}}-(\text{CH}_2)_q-\text{CH}=\text{CH}-\text{COR}_1 \quad \text{(III)}$$

wherein Ar represents carbocyclic aryl; Het represents 3-pyridyl or 3-pyridyl substituted by lower alkyl; m represents an integer from 1 to 5 inclusive; q represents zero or an integer from 1 to 3 inclusive; p represents zero or an integer from 1 to 5 inclusive; $\text{COR}_1$ represents carboxy or carboxy derivatized in the form of a pharmaceutically acceptable ester or amide; the N-oxide thereof; or a pharmaceutically acceptable salt thereof.

9. A compound according to claim 8 of formula III wherein m represents the integer 2, 3 or 4; q represents zero or the integer 1; p represents the integer 1, 2 or 3; Ar, Het, $R_a$ and $R_b$ have meaning as defined above; $\text{COR}_1$ represents carboxy or carboxy derivatized in the form of a pharmaceutically acceptable ester or amide; or a pharmaceutically acceptable salt thereof.

10. A compound according to claim 2 of the formula IIIa

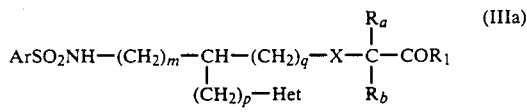

$$\text{ArSO}_2\text{NH}-(\text{CH}_2)_m-\underset{\underset{(\text{CH}_2)_p-\text{Het}}{|}}{\text{CH}}-(\text{CH}_2)_q-\text{X}-\underset{\underset{\text{R}_b}{|}}{\overset{\overset{\text{R}_a}{|}}{\text{C}}}-\text{COR}_1 \quad \text{(IIIa)}$$

wherein Ar represents carbocyclic aryl; Het represents 3-pyridyl or 3-pyridyl substituted by lower alkyl; X represents oxygen or sulfur; m represents an integer from 1 to 5; represents zero or an integer from 1 to 3; p represents zero or an integer from 1 to 5; $\text{COR}_1$ represents carboxy or carboxy derivatized in the form of a pharmaceutically acceptable ester $R_a$ and $R_b$ represent independently hydrogen or lower alkyl the N-oxide thereof; or a pharmaceutically acceptable salt thereof.

11. A compound according to claim 10 of formula IIIa wherein m represents the integer 2, 3 or 4; q represents zero or the integer 1; p represents the integer 1, 2 or 3; Ar, Het, X, $R_a$ and $R_b$ have meaning as defined above; $\text{COR}_1$ represents carboxy or carboxy derivatized in the form of a pharmaceutically acceptable ester or amide; or a pharmaceutically acceptable salt thereof.

12. A compound according to claim 2 of the formula

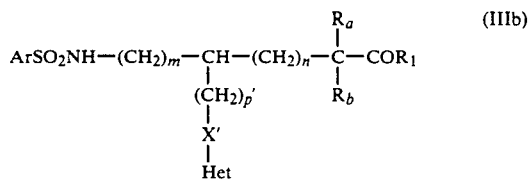

$$\text{ArSO}_2\text{NH}-(\text{CH}_2)_m-\underset{\underset{\underset{\underset{\text{Het}}{|}}{\text{X}'}}{|}}{\text{CH}}-(\text{CH}_2)_n-\underset{\underset{\text{R}_b}{|}}{\overset{\overset{\text{R}_a}{|}}{\text{C}}}-\text{COR}_1 \quad \text{(IIIb)}$$

wherein Ar represents carbocyclic aryl; Het represents 3-pyridyl or 3-pyridyl substituted by lower alkyl; X' represents oxygen or sulfur; m represents an integer from 1 to 5; n represents zero or an integer from 1 to 4; p' represents zero or an integer from 1 to 4; $\text{COR}_1$ represents carboxy or carboxy derivatized in the form of a pharmaceutically acceptable ester or amide; $R_a$ and $R_b$ represent independently hydrogen or lower alkyl; the N-oxide thereof; or a pharmaceutically acceptable salt thereof.

13. A compound according to claim 12 of formula IIIb wherein m represents the integer 2, 3 or 4; n represents the integer 1, 2 or 3; p' represents zero or the integer 1, 2 or 3; Ar, Het, X', $R_a$ and $R_b$ have meaning as defined in said claim; $\text{COR}_1$ represents carboxy or carboxy derivatized in the form of a pharmaceutically acceptable ester or amide; or a pharmaceutically acceptable salt thereof.

14. A compound according to claim 12 wherein m represents 4, n represents 1 and p' represents 2.

15. A compound according to claim 3 of the formula

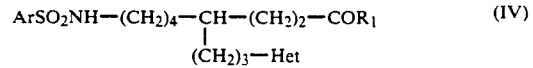

$$\text{ArSO}_2\text{NH}-(\text{CH}_2)_4-\underset{\underset{(\text{CH}_2)_3-\text{Het}}{|}}{\text{CH}}-(\text{CH}_2)_2-\text{COR}_1 \quad \text{(IV)}$$

wherein Ar represents carbocyclic aryl COR₁ represents carboxy or carboxy derivatized in the form of a pharmaceutically acceptable ester or amide; Het represents 3-pyridyl or 3-pyridyl substituted by lower alkyl, or the N-oxide thereof; or a pharmaceutically acceptable salt thereof.

16. A compound according to claim 15 of formula IV wherein Ar represents 1- or 2-naphthyl, phenyl or phenyl substituted by one or two substituents selected from halogen, trifluoromethyl, hydroxy, lower alkyl-(thio, sulfinyl or sulfonyl), lower alkoxy, lower alkyl, nitro, azido, amino, cyano, carboxy and lower alkoxycarbonyl; Het represents 3-pyridyl or 3-pyridyl substituted by lower alkyl, or the N-oxide thereof; COR₁ represents carboxy, carboxy esterified in the form of a pharmaceutically acceptable ester, or COR₁ represents carbamoyl; or a pharmaceutically acceptable salt thereof.

17. A compound according to claim 15 of formula IV wherein Ar represents 2-naphthyl, phenyl or phenyl substituted by lower alkyl, halogen, cyano or trifluoromethyl; Het represents 3-pyridyl; R₁ represents hydroxy, lower alkoxy or amino; or a pharmaceutically acceptable salt thereof.

18. A compound according to claim 15 of formula IV wherein Ar represents phenyl, chlorophenyl, fluorophenyl, tolyl or trifluoromethylphenyl; Het represents 3-pyridyl; R₁ represents hydroxy or lower alkoxy; or a pharmaceutically acceptable salt thereof.

19. A compound according to claim 10 of the formula

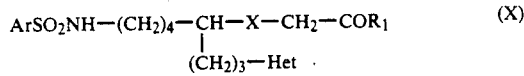

wherein Ar represents carbocyclic aryl; COR₁ represents carbocy or carboxy derivatized in the form of a pharmaceutically acceptable ester or amide; Het represents 3-pyridyl or 3-pyridyl substituted by lower alkyl, or the N-oxide thereof; X represents oxygen or sulfur; or a pharamceutically acceptable salt thereof.

20. A compound according to claim 19 wherein Ar represents 1- or 2-naphthyl, phenyl or phenyl substituted by one or two substituents selected from halogen, trifluoromethyl, hydroxy, lower alkyl-(thio, sulfinyl or sulfonyl), lower alkoxy, lower alkyl, nitro, azido, amino, cyano, carboxy and lower alkoxycarbonyl; Het represents 3-pyridyl or 3-pyridyl-N-oxide; X represents oxygen or sulfur; COR₁ represents carboxy, carboxy esterified in the form of a pharmaceutically acceptable ester, or carbamoyl; or a pharmaceutically acceptable salt thereof.

21. A compound according to claim 19 wherein Ar represents 2-naphthyl, phenyl or phenyl substituted by lower alkyl, halogen, cyano or trifluoromethyl; Het represents 3-pyridyl; X represents oxygen or sulfur; R₁ represents hydroxy, lower alkoxy or amino; or a pharmaceutically acceptable salt thereof.

22. A compound according to claim 19 wherein Ar represents phenyl, chlorophenyl, fluorophenyl, tolyl or trifluoromethylphenyl; Het represents 3-pyridyl; R₁ represents hydroxy or lower alkoxy; X represents oxygen or sulfur; or a pharmaceutically acceptable salt thereof.

23. A compound according to claim 22 wherein X represents oxygen.

24. A compound according to claim 22 wherein X represents sulfur.

25. A compound according to claim 12 of the formula

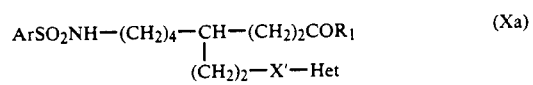

wherein Ar represents carbocyclic aryl; COR₁ represents carboxy or carboxy derivatized in the form of a pharmaceutically acceptable ester or amide; Het represents 3-pyridyl or 3-pyridyl substituted by lower alkyl, or the N-oxide thereof; X' represents oxygen or sulfur; or a pharmaceutically acceptable salt thereof.

26. A compound according to claim 25 wherein Ar represents 1- or 2-naphthyl, phenyl or phenyl substituted by one or two substituents selected from halogen, trifluoromethyl, hydroxy, lower alkyl-(thio, sulfinyl or sulfonyl), lower alkoxy, lower alkyl, nitro, azido, amino, cyano, carboxy and lower alkoxycarbonyl; Het represents 3-pyridyl or 3-pyridyl-N-oxide; X' represents oxygen or sulfur; COR₁ represents carboxy, carboxy esterified in the form of a pharmaceutically acceptable ester, or carbamoyl; or a pharmaceutically acceptable salt thereof.

27. A compound according to claim 25 wherein Ar represents 2-naphthyl, phenyl or phenyl substituted by lower alkyl, halogen, cyano or trifluoromethyl; Het represents 3-pyridyl; X' represents oxygen or sulfur; R₁ represents hydroxy, lower alkoxy or amino; or a pharmaceutically acceptable salt thereof.

28. A compound according to claim 25 wherein Ar represents phenyl, chlorophenyl, fluorophenyl, tolyl or trifluoromethylphenyl; Het represents 3-pyridyl; R₁ represents hydroxy or lower alkoxy; X' represents oxygen or sulfur; or a pharmaceutically acceptable salt thereof.

29. A compound according to claim 28 wherein X' represents oxygen.

30. A compound according to claim 28 wherein X' represents sulfur.

31. A compound according to claim 2 of the formula

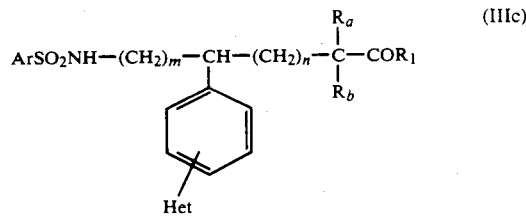

wherein Ar represents carbocyclic aryl; Het represents 3-pyridyl or 3-pyridyl substituted by lower alkyl; m represents an integer from 1 to 5; n represents zero or an integer from 1 to 4; COR₁ represents carboxy or carboxy derivatized in the form of a pharmaceutically acceptable ester or amide; R_a and R_b represent independently hydrogen or lower alkyl; or a pharmaceutically acceptable salt thereof.

32. A compound according to claim 31 wherein m represents the integer 2, 3 or 4; and n represents the integer 1, 2 or 3.

33. A compound according to claim 31 wherein m represents 4; n represents 1; Ar represents 2-naphthyl, phenyl or phenyl substituted by lower alkyl, halogen, cyano, or trifluoromethyl; Het represents 3-pyridyl; $COR_1$ represents carboxy, lower alkoxycarbonyl or carbamoyl; $R_a$ and $R_b$ represent hydrogen; or a pharmaceutically acceptable salt thereof.

34. A compound according to claim 1 of formula I wherein one of A, B and M represents lower alkylidenylene and the other two represent lower alkylene; Ar represents carbocyclic aryl; Het represents 3-pyridyl or 3-pyridyl substituted by lower alkyl; R represents the second bond to the adjacent alkylidenylene unsaturated carbon atom; a pharmaceutically acceptable ester or amide derivative thereof; or a pharmaceutically acceptable salt thereof.

35. A compound according to claim 1 of the formula

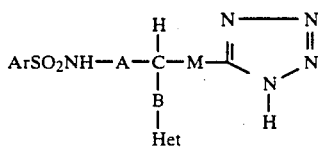

wherein A represents alkylene; B represents oxygen, sulfur, (oxy-, sulfinyl-, sulfonyl- or thio)-lower alkylene, lower alkylene, lower alkenylene, phenylene or a direct bond; M represents lower alkylene, lower alkylene interrupted by oxygen, sulfur, sulfinyl or sulfonyl, (oxy-, sulfinyl-, sulfonyl- or thio)-lower alkylene, lower alkenylene or a direct bond; Het represents 3-pyridyl or 3-pyridyl substituted by lower alkyl Ar represents carbocyclic aryl; the N-oxide thereof; or a pharmaceutically acceptable salt thereof.

36. A compound according to claim 35 of the formula

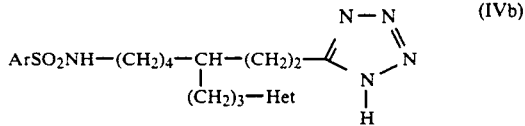

wherein Ar represents 1- or 2-naphthyl, phenyl or phenyl substituted by one or two substituents selected from halogen, trifluoromethyl, hydroxy, lower alkyl-(thio, sulfinyl or sulfonyl), lower alkoxy, lower alkyl, nitro, azido, amino, cyano, carboxy and lower alkoxycarbonyl, Het represents 3-pyridyl or 3-pyridyl substituted by lower alkyl, or the N-oxide thereof; or a pharmaceutically acceptable salt thereof.

37. A compound according to claim 36 wherein Ar represents 2-naphthyl, phenyl or phenyl substituted by lower alkyl, halogen, cyano or trifluoromethyl; Het represents 3-pyridyl; or a pharmaceutically acceptable salt thereof.

38. A compound according to claim 36 wherein Ar represents phenyl, chlorophenyl, fluorophenyl, tolyl or trifluoromethylphenyl; Het represents 3-pyridyl; or a pharmaceutically acceptable salt thereof.

39. A compound according to claim 15 being 8-(p-chlorophenylsulfonamido)-4-[3-(3-pyridyl)-propyl]-octanoic acid or a pharmaceutically acceptable salt thereof.

40. A compound according to claim 15 being 8-(p-fluorophenylsulfonamido)-4-[3-(3-pyridyl)-propyl]-octanoic acid or a pharmaceutically acceptable salt thereof.

41. A compound according to claim 8 being 8-(p-chlorophenylsulfonamido)-4-[3-(3-pyridyl)propyl]-oct-2-enoic acid or a pharmaceutically acceptable salt thereof.

42. A compound according to claim 12 being 8-(p-chlorophenylsulfonamido)-4-[2-(3-pyridyloxy)ethyl]octanoic acid or a pharmaceutically acceptable salt thereof.

43. A compound according to claim 3 being 8-(p-chlorophenylsulfonamido)-2-methyl-4-[3-(3-pyridyl)-propyl]octanoic acid or a pharmaceutically acceptable salt thereof.

44. A compound according to claim 19 being 8-(p-chlorophenylsulfonamido)-4-[3-(3-pyridyl)-propyl]-3-thiaoctanoic acid or a pharmaceutically acceptable salt thereof.

45. A compound according to claim 36 being 5-{7-(p-chlorophenylsulfonamido)-3-[3-(3-pyridyl)-propyl]-heptyl}-1H-tetrazole or a pharmaceutically acceptable salt thereof.

46. A pharmaceutical composition suitable for administration to mammals for the treatment or prevention of conditions or syndromes responsive to suppression of thromboxane activity comprising an effective thromboxane activity suppressing amount of a compound according to claim 1 in combination with one or more pharmaceutically acceptable carriers.

47. A method of suppressing thromboxane activity in mammals which comprises administering to a mammal in need thereof an effective thromboxane suppressing amount of a compound according to claim 1.

48. A method of inhibiting thromboxane synthesis in mammals which comprises administering to a mammal in need thereof an effective thromboxane synthetase inhibiting amount of a compound according to claim 1.

49. A method of blocking thromboxane receptor activity in mammals which comprises administering to a mammal in need thereof an effective thromboxane receptor blocking amount of a compound according to claim 1.

50. A method of inhibiting platelet aggregation in mammals which comprises administering to a mammal in need thereof an effective platelet aggregation inhibiting amount of a compound according to claim 1.

51. A method of treating or preventing thromboxane dependent conditions or syndromes in mammals which comprises administering to a mammal in need thereof an effective thromboxane activity suppressing amount of a compound according to claim 1.

52. A method according to claim 51 of treating or preventing occlusive vascular conditions.

53. A method according to claim 52 of treating or preventing peripheral vascular disorders, thrombosis, atherosclerosis, cerebral infarctions, myocardial infarctions, or coronary reocclusion after angioplasty, after coronary bypass surgery or after thrombolytic therapy.

54. A method according to claim 51 of preventing or treating myocardial infarctions, cerebral infarctions, angina, hypertension, renal disorders, peripheral vascular disorders, allograft rejection, pulmonary disorders, or vascular reocclusion after thrombolytic therapy, after angioplasty, or after coronary bypass surgery.

55. A method according to claim 52 of preventing coronary occlusion.

56. A method according to claim 52 of preventing coronary reocclusion from occurring after thrombolytic therapy, angioplasty or bypass surgery.

57. A method according to claim 51 of alleviating cyclosporin-induced nephrotoxicity.

58. A method of enhancing the cardiovascular effect of a thrombolytic agent, an angiotensin converting enzyme inhibitor, calcium channel blocker, anticoagulant or a serotonin-2 receptor antagonist, which comprises administering to a mammal in need thereof an effective thromboxane activity suppressing amount of a compound according to claim 1.

59. A method of enhancing the effect of thrombolytic agents in mammals which comprises administering to a mammal in need thereof an effective thromboxane activity suppressing amount of a compound according to claim 1.

60. A pharmaceutical formulation suitable for administration to a mammal comprising an effective thromboxane activity suppressing amount of a compound according to claim 1, in combination with another therapeutic agent selected from a thrombolytic agent, an angiotensin converting enzyme inhibitor, a calcium channel blocker, an anticoagulant, a serotonin-2-antagonist, or an immunosuppressive agent at an effective therapeutic dose, and one or more pharmaceutically acceptable carriers.

* * * * *

UNITED STATES PATENT AND TRADEMARK OFFICE
CERTIFICATE OF CORRECTION

PATENT NO. : 5,025,025
DATED : June 18, 1991
INVENTOR(S) : Bhagwat et al

It is certified that error appears in the above-indentified patent and that said Letters Patent is hereby corrected as shown below:

Column 68, line 43, claim 1, should read:

-- A, B and M represents lower alkylidenylene and the other two independently represent lower alkylen; R represents hydrogen unless A, B or M --

Column 69, line 12, claim 2, should read:
--(oxy-, sulfinyl-, sulfonyl- or thio)- lower alkylene, lower --

Column 69, line 42, claim 4, should read:

-- in the form of a pharmaceutically acceptable ester or --.

UNITED STATES PATENT AND TRADEMARK OFFICE
CERTIFICATE OF CORRECTION

PATENT NO. : 5,025,025
DATED : June 18, 1991
INVENTOR(S) : Bhagwat et al

It is certified that error appears in the above-indentified patent and that said Letters Patent is hereby corrected as shown below:

Column 70

Claim 10, line 17 should read:

-- from 1 to 5; n represents zero or an integer from 1 to 3; p --

Column 71,
Claim 19, line 38 should read:

-- sents carboxy or carboxy derivatized in the form of a --

Column 73,
Claim 35, line 26 should read:

-- wherein A represents lower alkylene; B represents oxygen, --

Signed and Sealed this

Twenty-fourth Day of August, 1993

Attest:

BRUCE LEHMAN

Attesting Officer

Commissioner of Patents and Trademarks